United States Patent
Liu

(10) Patent No.: US 9,340,616 B2
(45) Date of Patent: May 17, 2016

(54) METHODS AND COMPOSITIONS FOR HEPTAMERIC TARGETING LIGANDS

(71) Applicant: The University of North Carolina at Chapel Hill, Chapel Hill, NC (US)

(72) Inventor: Rihe Liu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/088,243

(22) Filed: Nov. 22, 2013

(65) Prior Publication Data

US 2014/0086835 A1 Mar. 27, 2014

Related U.S. Application Data

(63) Continuation-in-part of application No. PCT/US2012/039195, filed on May 23, 2012.

(60) Provisional application No. 61/488,906, filed on May 23, 2011.

(51) Int. Cl.

| | |
|---|---|
| C07K 16/26 | (2006.01) |
| A61K 49/00 | (2006.01) |
| C07K 14/195 | (2006.01) |
| C07K 16/28 | (2006.01) |
| G01N 33/574 | (2006.01) |
| C07K 14/47 | (2006.01) |
| C07K 14/485 | (2006.01) |

(52) U.S. Cl.
CPC ......... *C07K 16/2863* (2013.01); *A61K 49/0056* (2013.01); *C07K 14/195* (2013.01); *C07K 14/47* (2013.01); *C07K 14/485* (2013.01); *G01N 33/57492* (2013.01); *C07K 2319/735* (2013.01)

(58) Field of Classification Search
None
See application file for complete search history.

(56) References Cited

U.S. PATENT DOCUMENTS

2006/0292174 A1 12/2006 de los Rios et al.
2011/0085939 A1 4/2011 Salemme et al.

OTHER PUBLICATIONS

Arai et al. (Conformations of Variably Linked Chimeric Proteins Evaluated by Synchroton X-ray Small-Angle Scattering; Proteins: Structure, Function and Bioinformatices 57: 829-838 (2004).*
Lofblom et al. (Affibody molecules: Engineered proteins for therapeutic, diagnostic and biotechnological applications, FEBS Letters 584(2010) 2670-2680).*
Duan et al. "Fibronectin Type III Domain Based Monobody with High Avidity" *Biochemistry* 46:12656-12664 (2007).
Kim et al. "Heptameric Targeting Ligands against EGFR and HER2 with High Stability and Avidity" *PLOS ONE* 7(8):e43077 (13 pages) (2012).
Stark et al. "Arrangement of RNA and proteins in the spliceosomal U1 small nuclear ribonucleoprotein particle" *Nature* 409:539-542 (2001).
Terskikh et al. "'Peptabody': A new type of high avidity binding protein" *Proceedings of the National Academy of Sciences* 94:1663-1668 (1997).
Toro et al. "RNA binding in an Sm core domain: X-ray structure and functional analysis of an archaeal Sm protein complex" *The EMBO Journal* 20(9):2293-2303 (2001).
Toro et al. "Archaeal Sm Proteins form Heptameric and Hexameric Complexes: Crystal Structures of the Sm1 and Sm2 Proteins from the Hyperthermophile *Archaeoglobus fulgidus*" *Journal of Molecular Biology* 320(1):129-142 (2002).
Zhang et al. "Pentamerization of single-domain antibodies from phage libraries: a novel strategy for the rapid generation of high-avidity antibody reagents" *Journal of Molecular Biology* 335(1):49-56 (2004).
International Preliminary Report on Patentability Corresponding to International Application No. PCT/US2012/039195; Date of Mailing: Dec. 5, 2013; 8 Pages.
International Search Report and Written Opinion Corresponding to International Application No. PCT/US12012/039795; Date of Mailing: Sep. 12, 2012; 15 Pages.

* cited by examiner

*Primary Examiner* — James H Alstrum Acevedo
*Assistant Examiner* — Tara Martinez
(74) *Attorney, Agent, or Firm* — Myers Bigel & Sibley, P.A.

(57) ABSTRACT

The present invention provides a self assembly molecule having an affinity for one or more target molecules, for use in formation of a heptameric complex, comprising: a) a monomer comprising a multimerization domain of Archaeal Sm1 (AF-Sm1) protein or SM-like ribonucleoprotein from other organisms, able to interact with other molecules of the same monomer comprising a multimerization domain of AF-Sm1 protein or SM-like ribonucleoprotein to self-assemble into a heptamer; and b) a target binding domain or peptide attached directly or via a linker to the monomer of (a). Also provided are heptamers comprising these self assembly molecules and methods for their use in therapy, imaging and diagnostics.

22 Claims, 31 Drawing Sheets

A

B

C

GPQPQPKPQPK PEPEPQPQGG (SEQ ID NO:34)

Heptameric domain
MPPRPLDVLN RSLKSPVIVR LKGGREFRGT LDGYDIHMNL VLLDAEEIQN
GEVVRKVGSV VIRGDTVVFV SPAPGGE (SEQ ID NO:1)

Truncated heptameric domain
MPPRPLDVLN RSLKSPVIVR LKGGREFRGT LDGYDIHMNL VLLDAEEIQN GE
(SEQ ID NO:35)

A

B

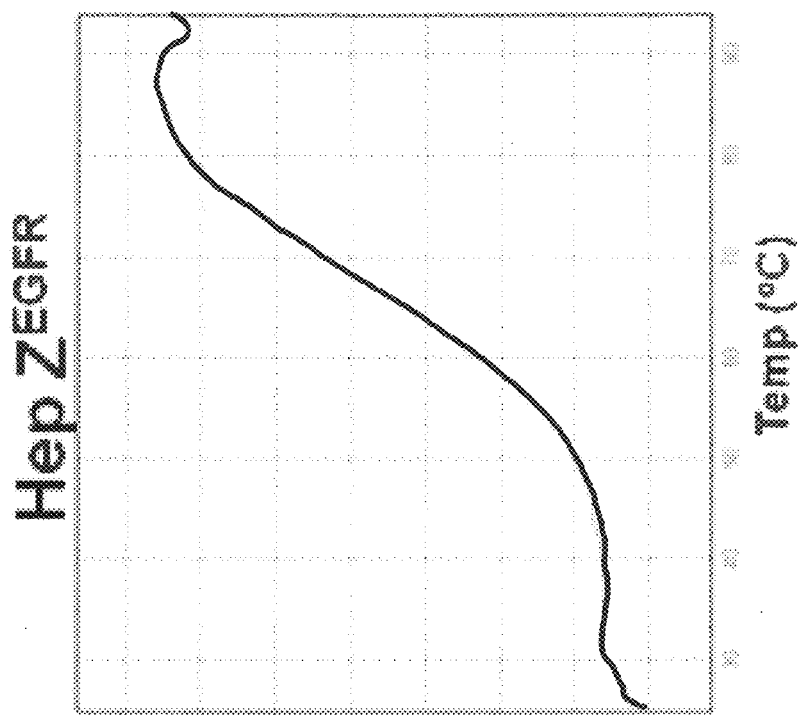
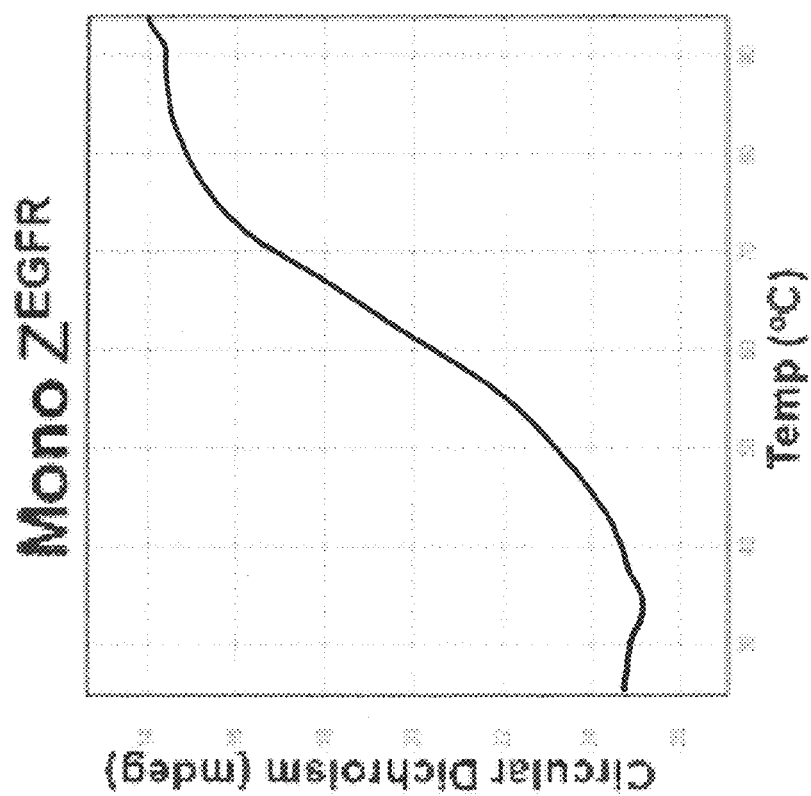

US 9,340,616 B2

METHODS AND COMPOSITIONS FOR HEPTAMERIC TARGETING LIGANDS

STATEMENT OF PRIORITY

This application is a continuation-in-part application of International Application Serial No. PCT/US2012/039195, filed May 23, 2012, which claims the benefit, under 35 U.S.C. §119(e), of U.S. Provisional Application Ser. No. 61/488,906, filed May 23, 2011, the entire contents of each of which are incorporated by reference herein.

STATEMENT OF GOVERNMENT SUPPORT

This invention was made with government support under Grant Nos. U54 CA119343 and U54 CA151652 awarded by the National Institutes of Health. The government has certain rights in this invention.

STATEMENT REGARDING ELECTRONIC FILING OF A SEQUENCE LISTING

A Sequence Listing in ASCII text format, submitted under 37 C.F.R. §1.821, entitled 5470-598TS_ST25.txt, 15,994 bytes in size, generated on Nov. 21, 2013 and filed via EFS-Web, is provided in lieu of a paper copy. This Sequence Listing is hereby incorporated by reference into the specification for its disclosures.

FIELD OF THE INVENTION

The present invention is directed to heptameric targeting ligands that bind to cell surface molecules with high affinity and specificity, for use as therapeutic agents, imaging and/or diagnostic agents and/or as agents to deliver therapeutic agents to target cells.

BACKGROUND OF THE INVENTION

Molecules that tightly and specifically bind to the biological targets are of great importance in a wide variety of biochemical, biological and biomedical applications. One of the major challenges in developing a targeting ligand is to improve its target-binding strength. Although such properties can be improved through extensive affinity maturation and engineering, the process is a slow, tedious, and often limited process. An important parameter for satisfactory in vivo targeting is the valency of the targeting ligand, which is defined as the number of antigen-binding sites. Evidence suggests that multivalency is useful for favorable biodistribution and pharmacokinetics in therapeutic and imaging applications. For example, it has been demonstrated that monovalent binding is often not enough to achieve desired cancer targeting, and most monovalent targeting ligands, even those with very high binding affinities, tend to have fast dissociation rates and provide only modest retention time on the target antigen in an in vivo non-equilibrium environment[1]. One of the most effective approaches used in nature to achieve strong binding between an antigen and its antibody is through multivalent interactions. Significantly, multivalency is an important intrinsic characteristic of natural antibodies in mammals. Although antibodies in camelidae and shark contain only heavy chains, they could acquire divalency through homodimerization. Some of the five naturally occurring antibody classes may form additionally dimer (IgA) or pentamer (IgM) complexes with tetravalency or decavalency, respectively. Naturally occurring IgM antibodies, for example, bind to antigens very tightly and efficiently, although the antigen-binding affinity of its monomeric form is relatively weak. This functional affinity or avidity of multiple antibody-antigen interactions when more than one interaction takes place between two molecules can be orders of magnitude higher than the intrinsic affinity of a single antibody-antigen interaction[2]. Multivalent targeting ligands have several major advantages over monovalent ligands in interaction with many cancer biomarkers that are present on cell surface. First, the target-binding strength of the multivalent ligands could be significantly improved. In principle, the resulting binding strength (avidity) can reach the product of original binding constants (affinities)[3]. Second, the multimerization process is often simultaneously accompanied with an increase of the molecular weight by several folds. This is particularly phenomenal for target-binding peptides or small domain-based antibody mimics. For example, the pentamerization of a 20 kDa targeting ligand results in a complex with 100 kDa, which is presumably less efficiently taken up and cleared by kidney[4].

During the past 15 years, several techniques in multivalency engineering of antibodies have been developed, including domain-swapping, linear fusion, chemical linking, self-association, and heterodimerization[1]. Compared to most of these methods that are limited to targeting ligands based on natural antibodies or their fragments, the self-association is a very general approach. Some multimerization domains have been successfully applied to generate multivalent antibody fragments, including TNF-alpha for the formation of homotrimers, the amphipathic helix of GCN4, the multimerization peptide of p53 and the core domain of streptavidin for the formation of tetramers, and the coiled-coil assembly domain of cartilage oligomeric matrix protein (COMP) and the B-subunit of bacterial verotoxin for the formation of pentamers[5-12]. Despite numerous advantages of using multivalent targeting ligands, successful and efficient conversion of a monovalent ligand into its multivalent form is challenging and requires a combination of unique features on the target-binding and the multimerization moieties. Due to the tendency of aggregation and steric hindrance, few multimerization domains are suitable for efficient multimerization. First, the scaffold should be small and soluble enough with a high expression level in bacteria. Second, the self-assembly of the monomeric domain into a multimeric structure with desired valency should be very efficient with high association constants and low aggregation tendency. The resulting complex should have a well defined parallel multimeric structure with high stability that allows for the introduction of a target-binding moiety and hinge region to achieve desired multivalency without disrupting the overall structure. This is particularly challenging when the complex is significantly diluted in the bloodstream under in vivo conditions. To circumvent these problems, new multimerization domains need to be identified for the generation of targeting ligands with higher avidity.

The present invention overcomes previous shortcomings in the art by providing heptameric targeting ligands that bind to cell surface molecules with high affinity and specificity, for use as therapeutic agents, imaging and/or diagnostic agents and/or as agents to deliver therapeutic agents to target cells.

SUMMARY OF THE INVENTION

In one embodiment, the present invention provides a self assembly molecule having an affinity for one or more target molecules, for use in formation of a heptameric complex, comprising: a) a monomer comprising a multimerization domain of Archaeal Sm1 (AF-Sm1) protein or SM-like ribonucleoprotein, able to interact with other molecules of the same monomer comprising a multimerization domain of AF-Sm1 protein or SM-like ribonucleoprotein to self-assemble into a heptamer; and b) a target binding domain or peptide attached directly or via a linker to the monomer of (a). Also provided herein is a heptamer comprising, consisting essentially of or consisting of seven of the above-described self assembly molecules of this invention.

In a further embodiment, the present invention provides a method of producing a heptamer having a binding strength for a target molecule that is increased from about 100 fold to about 10,000 fold as compared with a monomer control, comprising: a) combining a plurality of the self assembly molecules of this invention under conditions whereby the molecules self assemble into heptamers; and b) optionally isolating the heptamers, thereby producing the heptamer. Additionally provided is a heptamer produced by the method described herein.

In an additional embodiment, the present invention provides a method of treating cancer in a subject in need thereof, comprising administering to the subject an effective amount of a heptamer of this invention and/or a nucleic acid molecule of this invention, and/or a vector of this invention and/or a cell of this invention, wherein the target binding domain or peptide is specific for a target molecule on a cancer cell in the subject and the heptamer binds the target molecule on cancer cells in the subject, thereby treating cancer in the subject.

In yet another embodiment of this invention, a method is provided herein of detecting and/or localizing cancer cells in a subject, comprising administering to the subject an effective amount of a heptamer of this invention and/or a nucleic acid molecule of this invention, and/or the vector of this invention and/or a cell of this invention, wherein the targeting domain or peptide is specific for a target molecule on the surface of cancer cells in the subject and the heptamer further comprises an imaging molecule and/or detectable molecule, whereby the heptamer binds the target molecule on the surface of cancer cells in the subject and the imaging molecule is visualized and/or the detectable molecule is detected at its binding location in the subject, thereby detecting and/or localizing cancer cells in the subject.

Also provided herein is method of diagnosing cancer in a subject, comprising administering to the subject an effective amount of a heptamer of this invention and/or a nucleic acid molecule of this invention, and/or a vector of this invention and/or a cell of this invention, wherein the targeting domain or peptide is specific for a target molecule on the surface of cancer cells in the subject and the heptamer further comprises an imaging molecule and/or detectable molecule, whereby the heptamer binds the target molecule on the surface of cancer cells in the subject and the imaging molecule is visualized and/or the detectable molecule is detected on cancer cells in the subject, thereby diagnosing cancer in the subject.

A kit is also provided herein, comprising a heptamer of this invention and/or a nucleic acid molecule of this invention and/or a vector of this invention and/or a cell of this invention and instructions for their use in the treatment of cancer in a subject and/or detection and/or localization of cancer cells and/or other diseased cells in a subject and/or diagnosis of cancer and/or other disorders in a subject.

Further provided herein is a composition comprising a heptamer of this invention, a nucleic acid molecule of this invention, a vector of this invention and/or a cell of this invention, in any combination, in a pharmaceutically acceptable carrier.

In additional embodiments, the present invention provides a method of producing a heptamer comprising a siRNA molecule, a shRNA molecule and/or a miRNA molecule, comprising: a) combining a plurality of the self assembly molecules of this invention with the siRNA molecule, shRNA molecule and/or miRNA molecule, wherein the siRNA molecule, shRNA molecule and/or miRNA molecule comprises an $(rU)_n$-containing sequence or U-rich sequence at the 5' or 3' end of the siRNA molecule, shRNA molecule and/or miRNA molecule, wherein n is from about 4 to about 20, under conditions whereby the molecules self assemble into a heptamer comprising said siRNA molecule, shRNA molecule and/or miRNA molecule; and b) optionally isolating the heptamers, thereby producing the heptamer comprising the siRNA molecule, shRNA molecule and/or miRNA molecule. Also provided herein is a heptamer comprising an siRNA molecule, shRNA molecule and/or miRNA molecule of this invention, for example, as produced by this method.

The present invention further provides a method of producing a heptamer comprising an $oligo(dT)_n$-containing or dT-rich duplex or hairpin DNA molecule and an intercalating moiety-containing molecule, comprising: a) combining a plurality of the self assembly molecules of this invention with an $oligo(dT)_n$-containing or dT-rich DNA molecule, wherein n is from about 4 to about 20, and wherein said DNA molecule comprises an intercalating moiety-containing molecule at the 5' or 3' end of said DNA molecule, under conditions whereby the molecules self assemble into a heptamer; and b) optionally isolating the heptamers, thereby producing the heptamer comprising the oligo(dT)-containing or dT-rich duplex or hairpin DNA molecule and an intercalating moiety-containing molecule. Also provided herein is a heptamer comprising an oligo(dT)n-containing or dT rich duplex or hairpin DNA molecule and an intercalating moiety-containing molecule of this invention, for example, as produced by this method.

Additionally provided herein is method of treating cancer in a subject in need thereof, comprising administering to the subject an effective amount of a heptamer of this invention comprising an $oligo(dT)_n$-containing or dT rich duplex or hairpin DNA molecule and an intercalating moiety-containing molecule of this invention, wherein the target binding domain or peptide is specific for a target molecule on a cancer cell in the subject and the heptamer binds the target molecule on cancer cells in the subject, thereby treating cancer in the subject.

Further provided herein is a method of treating cancer in a subject in need thereof, comprising administering to the subject an effective amount of a heptamer of this invention comprising a siRNA molecule, shRNA molecule and/or miRNA molecule of this invention, wherein the target binding domain or peptide is specific for a target molecule on a cancer cell in the subject and the heptamer binds the target molecule on cancer cells in the subject, thereby treating cancer in the subject.

BRIEF DESCRIPTION OF THE DRAWINGS

FIGS. 14A-C. Heat stability assessment of the monomer and the heptamer by circular dichroism analysis. (A) Monomeric and heptameric $Z^{EGFR}$, (B) monomeric and heptameric $Z^{HER2}$ targeting ligands, and (C) heptameric core itself were prepared in a 10 mM phosphate buffer, pH 7.4. Temperature was increased from 25° C. to 94° C. Spectra were recorded at various temperatures. The ellipticity at 220 nm was used for the analysis.

DETAILED DESCRIPTION OF THE INVENTION

Figure 1:
FIGS. 1A-C. Schematic diagram and amino acid sequences of monomeric and heptameric molecules. A) Self-assembled heptameric molecules comprising target binding domains or peptide, linker, and followed by heptameric domain. His tag was introduced into the C-terminal of each molecule. B) Monomeric molecules were constructed without multimeric domain except truncated heptameric domain was used for PSMA binding monomer. C) Exemplary sequences.
Figure 1:
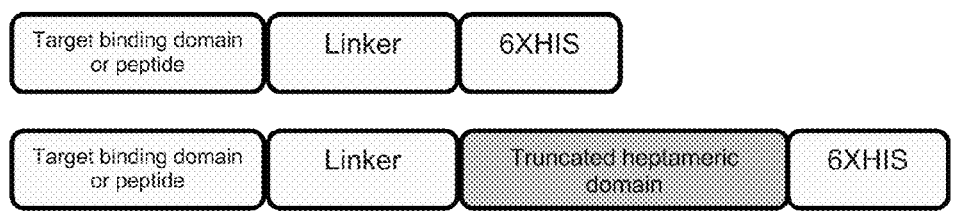

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to include variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising,".

The present invention is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The present invention is based on the unexpected discovery of a heptameric targeting ligand that binds a target molecule with high affinity and specificity, for use as a therapeutic agent, imaging and/or diagnostic agent and/or as an agent to deliver therapeutic agents to target cells. Such heptameric targeting ligands or heptamers can be used simultaneously as a therapeutic agent and an imaging and/or diagnostic agent, thus establishing their utility as a theranostic.

Thus, in one embodiment, the present invention provides a self assembly molecule having an affinity for one or more target molecules, for use in formation of a heptameric complex, comprising: a) a monomer comprising a multimerization domain of Archaeal Sm1 (AF-Sm1) protein or SM-like ribonucleoprotein from other organisms (see, e.g., refs 15, 16), able to interact with other molecules of the same monomer comprising a multimerization domain of AF-Sm1 protein or SM-like ribonucleoprotein to self-assemble into a heptamer; and b) a targeting binding domain or peptide fused directly or via a linker to the monomer of (a).

In some embodiments, the multimerization domain of the monomer can comprise, consist essentially of or consist of an amino acid sequence in the range of about 50-80 (e.g., 50, 55, 56, 57, 58, 59, 60, 61, 62, 63, 64, 65, 66, 67, 68, 69, 70, 71, 72, 73, 74, 75, 76, 77, 78, 79, 80, 81 or 82) residues of an Archaeal Sm1 (AF-Sm1) protein or SM-like ribonucleoprotein, non-limiting examples of which include: a) at least about 50 residues of the amino acid sequence of SEQ ID NO:1 (MPPRPLDVLN RSLKSPVIVR LKGGREFRGT LDGYDIHMNL VLLDAEEIQN GEVVRKVGSV VIRGDTVVFV SPAPGGE; from *Archaeoglobus fulgidus*); b) at least about 50 residues of the amino acid sequence of SEQ ID NO:2 (MARPLDVLNK ALKTPVLVRL KGGREFRGTL DGYDIHMNLV LVDAEEIQNG EVVRKLGSVV IRGDTVVFVS PSQ; from *Ferroglobus placidus*); c) at least about 50 residues of the amino acid sequence of SEQ ID NO:3 (MAKRPLDVLN KALQTPVLVR LKGGREFRGI LNGYDIHMNI VLENAEEIQN GEVVRKLGSV VIRGDTVVFV SPSE; from *Archaeoglobus profundus*); d) at least about 50 residues of the amino acid sequence of SEQ ID NO:4 (MANRPLDVLN KALQTPVLVR LKGGREFRGI LNGYDIHMNL VLQNAEEIQG GEVIRKLGSV VIRGDTVVFV SPSP; from *Archaeoglobus veneficus*); e) at least about 50 residues of the amino acid sequence of SEQ ID NO:5 (MGNRPLDILN NALNTAVIVR LKGAREFRGT LQGYDVHMNL VLDEAEEIKE GEIIRKIGSV VVRGDNVVYV SP; from *Methanohalophilus mahii*); f) at least about 50 residues of the amino acid sequence of SEQ ID NO:6 (MANRPLDILN NALNTPVIVR LKGAREFRGE LQGYDVHMNL VLDNAEELKD GEIVRKLGSV VIRGDNVVYL SP; from *Methanosalsum zhilinae*); g) at least about 50 residues of the amino acid sequence of SEQ ID NO:7 (RPLDAL GNSLNSPVII KLKGDREFRG VLKSFDLHMN LVLNDAEELE DGEVTRRLGT VLIRGDNIVY ISP; from *Methanobacterium thermoautotrophicum*); and h) at least about 50 residues of the amino acid sequence of SEQ ID NO:8 (RPLDALGN SLNSPVIIKL KGDREFRGVL KSFDLHMNLV LNDAEELEDG EVTRRLGTVL IRGDNIVYIS; from *Methanobacterium*).

The multimerization domain of this invention can also be obtained or derived from any Sm or Lsm family small nuclear ribonucleoprotein, as are known in the art, which can be, for example, from *Archaeoglobus, Ferroglobus, Archaeoglobus, Methanohalophilus, Methanosalsum, Methanothermus, Methanocella, Methanohalobium, Methanosarcina, Methanococcoides, Methanosaeta, Methanothermobacter, Methanobrevibacter* or *Methanobacterium*.

In some embodiments of the self assembly molecule of this invention, the target binding domain or peptide of can be attached (e.g., fused) via a linker to the monomer. Nonlimiting examples of a linker of this invention include: a) a linker comprising the amino acid sequence of SEQ ID NO:4 (GPQPQPKPQPK); b) a linker comprising, consisting essentially of or consisting of the amino acid sequence of SEQ ID NO:5 ((GGGGS)$_n$, wherein n can be any number such as 1, 2, 3, 4, 5, 6, 7, 8, 9, 10, etc.; e.g., (GGGGS)$_3$); c) a linker comprising the amino acid sequence of SEQ ID NO:6 (TPPTPSPSTPPTPSP; human IgA1 heavy chain); d) a linker comprising the amino acid sequence of SEQ ID NO:7 (EFPKPSTPPGSSGGAP; murine IgG3-hinge region); e) a linker comprising the amino acid sequence of SEQ ID NO:8 (PQPQPQPKPQPKPEPE; camel IgG); f) a linker comprising the amino acid sequence of SEQ ID NO:9 ((GGGS)$_n$, wherein n can be 1, 2, 3, 4, 5, 6, 7, 8, 9, 10, etc.); g) a linker comprising the amino acid sequence of SEQ ID NO:10 ((GSGSGS)$_n$, wherein n can be 1, 2, 3, 4, 5, 6, 7, 8, 9, 10, etc.); h) a linker comprising of the amino acid sequence of SEQ ID NO:11 ((TPPTPSP)$_n$, wherein n can be any number such as 1, 2, 3, 4, 5, 6, 7, 8, 9, 10, etc.); i) a linker comprising the amino acid sequence of SEQ ID NO:12 ((PQPQPK)$_n$, wherein n can be any number such as 1, 2, 3, 4, 5, 6, 7, 8, 9, 10, etc.); j) a linker comprising the amino acid sequence of SEQ ID NO:13 ((PQPQPE)$_n$, wherein n can be any number such as 1, 2, 3, 4, 5, 6, 7, 8, 9, 10, etc.); k) a linker comprising the amino acid sequence of SEQ ID NO:14 (PEPEPQPQGG); and l) any combination of (a)-(k) above.

The linker peptide of this invention can also be a peptide of about 5 to about 50 amino acids (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49, or 50) having an amino acid composition that provides for the functional feature of having the appropriate length and flexibility to facilitate the positioning of the target binding domains or peptides of the heptameric targeting ligand for binding at their respective sites on the target molecule(s) on the cell surface In some embodiments of this invention, the target molecule to which the heptamer of this invention binds can comprise, consist essentially of or consist of the extracellular domain of a cell surface receptor such as, for example, a member of the epidermal growth factor receptor family (e.g., EGFR, HER1, HER2, HER3, HER4, etc., as are well known in the art), c-MET, vascular endothelial growth factor receptor (e.g., VEGFR1, VEGFR2, VEGFR3), insulin receptor, insulin-like growth factor receptor (IGFR), prostate specific membrane antigen (PSMA), mesothelin, hepsin, an integrin, mucin (e.g., MUC16), a cell surface cluster of differentiation (CD) molecule (nonlimiting examples of which include CD20, CD22, CD30, CD33, CD44, CD56, etc.), and any combination thereof.

In further embodiments of this invention, the target binding domain or peptide of the heptamer of this invention can comprise, consist essentially of or consist of an antibody fragment, a single domain antibody fragment, a single chain polypeptide of a $V_H$ or $V_L$ domain of an antibody, a peptide or protein derived from a binding and/or framework region of an antibody, a single domain antibody mimic based on non-immunoglobulin scaffolds (such as Z domains, FN3 domains, DARPINs, etc.), an epidermal growth factor receptor (EGFR)-binding, a HER2-binding, a HER3-binding, a PSMA-binding, an $\alpha_v\beta_3$-binding Z domain or FN3 domain or DARPIN, a short target-binding peptide containing natural and/or unnatural amino acids, a molecule or binding portion thereof which specifically binds to the extracellular domain of a cell surface receptor, and any combination thereof. Nonlimiting examples of a target binding domain or peptide of this invention include:

EGFR-binding Z domain:
VDNKFNKEMWAAWEEIRNLPNLNGWQMTAFIASLVDDPSQSANLLAEAKK

LNDAQAPK
(Friedman et al, Journal of Molecular Biology 376: 1388-1402 (2008))

HER2-binding Z domain:
VDNKFNKEMRNAYWEIALLPNLNNQQKRAFIRSLYDDPSQSANLLAEAKK

LNDAQAPK
(Orlova et al. Cancer Research 66(8): 4339-4348 (2006))

PSMA-binding peptide:
QKHHNYL (Lupold and Rodriguez Molecular Cancer Therapeutics 3(5): 597-603 (2004))

PSMA-binding FN3 domain:
MGVSDVPRDLEVVAATPTSLLISWDAPAVTVRYYRITYGETGGNSPVQEF

TVPGSKSTATISGLKPGVDYTITVYAVTQKHHNYLPISINYRTEIDKPSQ

GRP78-binding peptide:
WIFPWIQLGGS
(Arap et al. Cancer Cell 6(3): 275-84 (2004))

EGFR-binding peptide:
YHWYGYTPQNVI
(Li et al, FASEB Journal 19(14): 1978-1985 (2005))

-continued
Plectin-1 -binding peptide:
KTLLPTPGGS
(Kelly et al. PLoS Medicine 5(4): e85 2008))

HER3-binding Z domain:
VDNKFNKERYSAYYEIWQLPNLNVRQKAAFIGSLQDDPSQSANLLAEAKK

LNDAQAPK
(Kronqvist et al. Protein Engineering, Design and Selection 24(4): 385-396 (2011))

$\alpha_v\beta_3$-binding FN3 domain:
MGVSDVPRDLEVVAATPTSLLISWDAPAVTVRYYRITYGETGGNSPVQEF TVPGSKSTATISGLKPGVDYTITVYAVTPRGDWNEGSKPISINYRT
(Richards et al. Journal of Molecular Biology 326: 1475-1488 (2003))

TNFα-binding FN3 domain:
MGVSDVPRDLEVVAATPTSLLISWRPTSNPPRYYRITYGETGGNSPVQEF

TVPPWASTATISGLKPGVDYTITVYAVTAQTGHHLHDKPISINYRT
(Xu et al. Chemistry & Biology 9: 933-942 (2002))

VEGFR-binding FN3 domain:
MGVSDVPRDLEVVAATPTSLLISWRHPHFPTRYYRITYGETGGNSPVQEF

TVPLQPPTATISGLKPGVDYTITVYAVTDGRNGRLLSIPISINYRT
(Getmanova et al. Chemistry & Biology 13: 549-556 (2006))

Gastrin-releasing peptide:
GNHWAVGHLM

In some embodiments, the target binding domain or peptide on a given heptamer is the same and in some embodiments there can be two or more different target binding domains or peptides on a given heptamer. In some embodiments, the multimerization domain of each of the seven monomers that make up a heptamer of this invention is the same.

It is also understood that the peptides and polypeptides of this invention may also contain conservative substitutions where a naturally occurring amino acid is replaced by one having similar properties and which does not alter the function of the polypeptide or peptide. Such conservative substitutions are well known in the art. Thus, it is understood that, where desired, modifications and changes may be made in the nucleic acid and/or amino acid sequence of the peptides and polypeptides of the present invention and still obtain a peptide or polypeptide having like or otherwise desirable characteristics. Such changes may occur in natural isolates or may be synthetically introduced using site-specific mutagenesis, the procedures for which, such as mis-match polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

In some embodiments, the target binding domain or peptide can be attached to the monomer at the amino terminus and/or at the carboxyl terminus of the self assembly molecule.

In further embodiments, the self assembly molecule of this invention can further comprise a histidine tag (e.g., 6×HIS).

In additional embodiments, the molecule of this invention can comprise a diagnostic molecule, a therapeutic molecule, an imaging molecule or any combination thereof. Such a molecule can, in some embodiments, comprise an N- and/or C-terminal cysteine for site-specific conjugation with other molecules, such as a diagnostic molecule, a therapeutic molecule, an imaging molecule, nanoparticles or any combination thereof.

The present invention further provides the self assembly molecule of this invention in heptameric form and also provides the self assembly molecule of this invention in heptameric form in the absence of any cysteine residues (e.g., no cysteine residues are present to form disulfide bonds to maintain the oligomeric state of the heptamer and thus no cysteine residues are present in the heptamer with the exception of optionally incorporating an N- and/or C-terminal cysteine for site-specific conjugation with other molecules as described herein, wherein the N- and/or C-terminal cysteine does not maintain the oligomeric state of the heptamer).

In further embodiments, the present invention provides a heptamer comprising seven self assembly molecules of this invention, wherein in some embodiment, such a heptamer can lack any cysteine residues that maintain the oligomeric state.

The heptameric targeting ligands bind to cell surface receptors much more tightly than the monomeric ligand due to the multivalent effect. If the target-binding site is at or close to the natural ligand binding site, such interaction will disrupt the interaction between the natural ligand and its receptor. Thus, the heptameric targeting ligands bind to cell surface molecules with high affinity and specificity and are useful as therapeutic agents, imaging and/or diagnostic agents and/or as agents to deliver therapeutic agents to target cells.

In some embodiments, the heptamer of this invention can have a binding strength (affinity) for a target molecule that is increased about 10 fold, 20 fold, 30 fold, 40 fold, 50 fold, 60 fold, 70 fold, 80 fold, 90 fold, 100 fold, 200 fold, 500 fold, 1000 fold, 2000 fold, 3000 fold, 4000 fold, 5000 fold or 10,000 fold as compared with a monomer control (e.g., a self assembly molecule comprising a monomer as described herein). In some embodiments, the affinity for the target molecule is increased from about 100 fold to about 10,000 fold relative to a monomer control.

Further provided herein is a method of producing a heptamer having a binding strength (affinity) for a target molecule that is increased about 10 fold, 20 fold, 30 fold, 40 fold, 50 fold, 60 fold, 70 fold, 80 fold, 90 fold, 100 fold, 200 fold, 500 fold, 1000 fold, 2000 fold, 3000 fold, 4000 fold, 5000 fold or 10,000 fold as compared with a monomer control, comprising combining a plurality of the self assembly molecules of this invention in an environment and/or under conditions whereby the molecules self assemble into heptamers and optionally isolating the heptamers from the environment, thereby producing the heptamer. A heptamer produced by the method of this invention is also provided herein.

In additional embodiments, the present invention provides a method of producing a heptamer comprising a siRNA molecule, a shRNA molecule and/or a miRNA molecule, comprising: a) combining a plurality of the self assembly molecules of claim 1 with the siRNA molecule, shRNA molecule and/or miRNA molecule, wherein the siRNA molecule, shRNA molecule and/or miRNA molecule comprises an $(rU)_n$-containing sequence or U-rich sequence at the 5' or 3' end of the siRNA molecule, shRNA molecule and/or miRNA molecule, wherein n is from about 4 to about 20, under conditions whereby the molecules self assemble into a heptamer comprising said siRNA molecule, shRNA molecule and/or miRNA molecule; and b) optionally isolating the heptamers, thereby producing the heptamer comprising the siRNA molecule, shRNA molecule and/or miRNA molecule. Also provided herein is a heptamer comprising an $(rU)_n$-containing siRNA, shRNA and/or miRNA molecule(s) of this invention, for example, as produced by this method. The siRNA, shRNA and miRNA molecules of this invention can be specific for any nucleic acid molecule or gene of interest and the use of siRNA, shRNA and miRNA molecules in diagnostics and therapeutics are well known in the art.

The present invention further a method of producing a heptamer comprising an $oligo(dT)_n$-containing or dT-rich duplex or hairpin DNA molecule and an intercalating moiety-containing molecule, comprising: a) combining a plurality of the self assembly molecules of this invention with an oligo $(dT)_n$-containing or dT-rich DNA molecule, wherein n is from about 4 to about 20, and wherein said DNA molecule comprises an intercalating moiety-containing molecule at the 5' or 3' end of said DNA molecule under conditions whereby the molecules self assemble into heptamers; and b) optionally isolating the heptamers, thereby producing the heptamer comprising the oligo(dT)-containing or dT-rich duplex or hairpin DNA molecule and an intercalating moiety-containing molecule.

Also provided herein is a heptamer comprising an oligo $(dT)_n$-containing or dT-rich duplex or hairpin DNA molecule and an intercalating moiety-containing molecule of this invention, for example, as produced by this method. Nonlimiting examples of an intercalating moiety-containing molecule of this invention include a DNA intercalating agent, daunorubicin, mitoxantrone, doxorubicin, pirarubicin, epirubicin and any combination thereof.

Additionally provided herein is method of treating cancer in a subject in need thereof, comprising administering to the subject an effective amount of a heptamer of this invention comprising an $oligo(dT)_n$-containing or dT-rich duplex or hairpin DNA molecule and an intercalating moiety-containing molecule of this invention, wherein the target binding domain or peptide is specific for a target molecule on a cancer cell in the subject and the heptamer binds the target molecule on cancer cells in the subject, thereby treating cancer in the subject.

Further provided herein is a method of treating cancer in a subject in need thereof, comprising administering to the subject an effective amount of a heptamer of this invention comprising an siRNA, shRNA and/or miRNA molecule of this invention, wherein the target binding domain or peptide is specific for a target molecule on a cancer cell in the subject and the heptamer binds the target molecule on cancer cells in the subject, thereby treating cancer in the subject.

The present invention further provides a method of treating an infectious disease (e.g., human immunodeficiency virus (HIV) infection, hepatitis C virus (HCV) infection, hepatitis B virus (HBV) infection as nonlimiting examples), comprising administering to a subject in need thereof an effective amount of a heptamer of this invention, wherein the target binding domain or peptide is specific for a target molecule on a cell infected by a pathogen and/or a target molecule on a pathogen, thereby treating the infectious disease in the subject.

As used herein, the terms "U-rich" or "dT-rich" describe a nucleic acid molecule comprising, consisting essentially of or consisting of single-stranded RNA or DNA, respectively, comprising, consisting essentially of or consisting of about 4 to about 25 nucleotides in which about 4 to about 18 nucleotides are rU or dT at the 5' and/or 3' end of the nucleic acid molecule.

The present invention also provides an isolated nucleic acid molecule encoding the self assembly molecules of the heptamer of this invention, a vector comprising the nucleic acid molecule of this invention, a cell (e.g., an isolated cell and/or transformed cell) comprising the nucleic acid molecule of this invention and a cell (e.g., an isolated cell and/or transformed cell) comprising the vector of this invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence, which is naturally occurring or may include alternative codons, which encode the same amino acid as that which is found in the naturally occurring sequence. Furthermore, nucleic acids may include codons, which represent conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a peptide and/or polypeptide of this invention.

The present invention further provides a vector comprising a nucleic acid encoding a peptide and/or polypeptide of this invention. The vector can be any expression vector (e.g., prokaryotic or eukaryotic) which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise, for example, viral nucleic acid including, but not limited to, vaccinia virus, adenovirus, retrovirus, alphavirus and/or adeno-associated virus nucleic acid. The nucleic acid or vector of this invention can also be in a liposome or a delivery vehicle, which can be taken up by a cell via receptor-mediated or other type of endocytosis.

Also provided herein is a composition comprising the heptamer of this invention, the nucleic acid molecule of this invention, the vector of this invention and/or the cell of this invention, as individual components or in any combination, in a pharmaceutically acceptable carrier. By "pharmaceutically acceptable carrier" is meant a carrier that is compatible with other ingredients in the pharmaceutical composition and that is not harmful or deleterious to the subject. The carrier can be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

The compositions of this invention can be used, for example, in the production of a medicament for the use in treatment of a disease and/or disorder as described herein.

The compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, intraocular or intravenous), topical (i.e., both skin and mucosal surfaces, including airway surfaces) and transdermal administration, although the most suitable route and dosage intervals in any given case will depend, as is well known in the art, on such factors as the species, age, gender and overall condition of the subject, the nature and severity of the condition being treated and/or on the nature of the particular composition (i.e., dosage, formulation, mode of administration) that is being administered. In some embodiments, the composition of this invention can be administered to a subject as an eye drop solution and/or via injection into the eye.

Administration of the nucleic acids of this invention can be achieved by any one of numerous, well-known approaches, for example, but not limited to, direct transfer of the nucleic acids, in a plasmid or viral vector, or via transfer in cells or in combination with carriers such as cationic liposomes. Such methods are well known in the art and readily adaptable for use in the methods described herein.

A subject of this invention can be any animal that is susceptible to any of the disorders (e.g., cancer, diabetes, asthma, etc.) and can be treated and/or diagnosed and/or detected according to the methods described herein. Nonlimiting examples of a subject of this invention include a mammal, a reptile, an avian or an amphibian (e.g., mouse, bird, dog, cat, cow, horse, fish). In certain embodiments of this invention, the subject is a mammalian subject and in particular embodiments, the subject is a human. A subject "in need thereof" is a subject who is susceptible to having, is at increased risk of having, has been diagnosed as having, or is suspected of having a disorder (e.g., cancer, diabetes, asthma) of this invention "Effective amount" or "treatment effective amount" as used herein refers to an amount of a protein, fragment, nucleic acid molecule, vector and/or composition of this invention that is sufficient to produce a desired effect, which can be a therapeutic effect and/or an improvement. Alternatively stated, a "treatment effective" or "effective" amount is an amount that will provide some alleviation, mitigation, decrease or stabilization in at least one clinical symptom/sign in the subject. An "effective amount" of a compound of this invention also refers to a nontoxic but sufficient amount to provide a desired therapeutic effect. Those skilled in the art will appreciate that the therapeutic effects need not be complete or curative, as long as some benefit is provided to the subject. The effective amount or treatment effective amount will vary with the age, general condition of the subject, the severity of the condition being treated, the particular compound, agent, substance or composition administered, the duration of the treatment, the nature of any concurrent treatment, the pharmaceutically acceptable carrier used if any, and like factors within the knowledge and expertise of those skilled in the art. As appropriate, an "effective amount" or "treatment effective amount" in any individual case can be determined by one of ordinary skill in the art by reference to the pertinent texts and literature and/or by using routine pharmacological procedures. (Remington, *The Science And Practice of Pharmacy* (20th ed. 2000)).

The formulation of therapeutic compounds and compositions of the invention and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the subject. Persons of ordinary skill can easily determine optimum dosages, dosing methodologies and repetition rates. Optimum dosages may vary depending on the relative potency of individual oligonucleotides or other antagonists, and can generally be estimated based on $EC_{50}$s found to be effective in in vitro and in vivo animal models.

A nonlimiting example of a dosage range for administration of a heptameric targeting ligand protein of this invention to a subject includes about 10 mg/kg to about 1000 mg/kg (e.g., about 1.0 mg/kg, about 5 mg/kg, about 10 mg/kg, about 20 mg/kg, about 50 mg/kg, about 75 mg/kg, about 100 mg/kg, about 200 mg/kg, about 300 mg/kg, about 500 mg/kg, about 700 mg/kg, about 1000 mg/kg, about 2000 mg kg, etc.). The protein may be given once or more daily, every other day, every three days, weekly, monthly or yearly, including over the lifetime of the subject A nonlimiting example of a dosage range for administration of a nucleic acid molecule encoding a self assembly molecule comprising a monomer comprising a multimerization domain and a target binding peptide or domain of this invention includes about 50 μg to about 10 mg per dose (e.g., about 10 μg, about 20 mg, about 50 μg, about 100 about 200 μg, about 500 μg, about 700 μg, about 1 mg, about 2 mg, about 5 mg, about 10 mg, about 15 mg, about 20 mg per dose, etc.). The nucleic acid may be given once or more daily, every other day, every three days, weekly, monthly or yearly, including over the lifetime of the subject "Treat" or "treating" as used herein refers to any type of action or implementation that imparts a benefit to a subject that is diagnosed with, at risk of having, suspected to have and/or likely to have a disease or disorder that can be responsive in a positive way to a compound or composition of this invention. A benefit can include an improvement in the condition of the subject (e.g., in one or more symptoms), delay and/or reversal in the progression of the condition, prevention or delay of the onset of the disease or disorder, etc.

In further embodiments, the present invention provides various methods employing the heptamers of this invention. Thus, in one embodiment, the present invention provides a method of treating cancer in a subject in need thereof, comprising administering to the subject an effective amount of the heptamer of this invention and/or the nucleic acid molecule of this invention and/or the vector of this invention and/or the cell of this invention, wherein the target binding domain or peptide is specific for a target molecule on a cancer cell in the subject and the heptamer binds the target molecule on cancer cells in the subject, thereby treating the cancer in the subject. Nonlimiting examples of dosage ranges for administration of a heptameric targeting ligand protein of this invention to a subject include 10 mg/kg to 1000 mg/kg. The protein may be given once or more daily, every three days, weekly, monthly or yearly, including over the lifetime of the subject.

Nonlimiting examples of dosage ranges for administration of a nucleic acid molecule encoding the heptameric targeting ligand protein of this invention include 50 ug to 10 mg per dose. The nucleic acid may be given once or more daily, every three days, weekly, monthly or yearly, including over the lifetime of the subject.

In some embodiments, the targeting domain or peptide of the heptamer can comprise, consist essentially of or consist of, an epidermal growth factor receptor (EGFR)-binding peptide, Z domain or FN3 domain, a HER2-binding peptide, Z domain or FN3 domain, a PSMA-binding peptide, Z domain or FN3 domain, an $\alpha_v\beta_3$-binding peptide, Z domain or FN3 domain.

In some embodiments of the methods of this invention, the heptamer can further comprise a cytotoxic moiety that kills the cancer cell subsequent to binding of the heptamer to cancer cells in the subject. In various embodiments, the cytotoxic moiety can be but is not limited to a small molecule, isotope, drug-containing nanoparticle, protein toxin, nucleic acid-based therapeutic agents (e.g., siRNA, miRNA, antisense, anti-gene oligonucleotide, etc.), or any combination thereof. Nonlimiting examples of cytotoxic small molecules include auristatin E, maytansinoids, SN-38, calicheamicin, taxoids, epothilones, vinblastine, breflate, depsipeptide, and jasplakinolide or their derivatives as are known in the art. Nonlimiting examples of radioisotopes include copper-67, yttrium-90, and indium-111. Nonlimiting examples of cytotoxic protein toxins include ricin, diphtheria toxin, colicin Ia, exotoxin A, abrin, and gelonin. Nonlimiting examples of nanoparticles include gold nanoparticles, magnetite nanoparticles, PLGA-based nanoparticles, and liposome nanoparticles. Nonlimiting examples of nucleic acid-based agents include siRNA, miRNA, antisense, anti-gene oligonucleotides, etc., as are well known in the art.

The present invention further provides a method of detecting and/or localizing cancer cells in a subject, comprising administering to the subject an effective amount of the heptamer of this invention (e.g., a heptamer comprising an RNA or DNA molecule as described herein) and/or the nucleic acid molecule of this invention and/or the vector of this invention and/or the cell of this invention, wherein the target binding domain or peptide is specific for a target molecule on a cancer cell in the subject and the heptamer further comprises an imaging molecule and/or detectable molecule, whereby the heptamer binds the target molecule on cancer cells in the subject and the imaging molecule is visualized and/or the detectable molecule is detected at its binding location on cancer cells in the subject, thereby detecting and/or localizing cancer cells in the subject. As noted herein, in such a method of detecting and/or localizing cancer cells in the subject, the heptamer (e.g., a heptamer comprising an RNA or DNA molecule as described herein) can also be simultaneously acting as a therapeutic agent to treat the cancer in the subject.

In further embodiments, the present invention provides a method of diagnosing cancer in a subject, comprising administering to the subject an effective amount of the heptamer of this invention (e.g., a heptamer comprising an RNA or DNA molecule as described herein) and/or the nucleic acid molecule of this invention and/or the vector of this invention and/or the cell of this invention, wherein the target binding domains or peptide is specific for a target molecule on a cancer cell in the subject and the heptamer further comprises an imaging molecule and/or detectable molecule, whereby the heptamer binds the target molecule on cancer cells in the subject and the imaging molecule is visualized and/or the detectable molecule is detected on cancer cells in the subject, thereby diagnosing cancer in the subject.

In the methods described herein, the imaging molecule can be but is not limited to an MRI contrast agent, a radioisotope for PET and nuclear medicine (e.g., $^{64}$Cu-ATSM, $^{18}$F-FDG, fluoride, FLT, FMISO, gallium, technetium-99m, etc.), a near-IR fluorescence molecule, a nanoparticle-containing imaging agent or any combination thereof.

In the embodiments of the invention employing imaging, any suitable imaging modality can be used to view and/or image the imaging molecule in the body of a subject. Examples of imaging modalities/systems include, but are not limited to, MRI Scanners, Ultrasound systems, X-ray systems including Computed Tomography (CT) Scanners, Combined Positron Emission Tomography and Computed Tomography (PET/CT) Scanners, Multispectral fluorescence camera systems, external and intraoperative fiber optic camera or detection systems, and implantable or catheter based medical sensors or detectors and the like as are well known in the art.

Nonlimiting examples of a cancer antigen (i.e., an antigen specifically associated with cancer cells that can be targeted with the heptameric targeting ligand of this invention) include, HER2/neu and BRCA1 antigens for breast cancer, MART-1/MelanA, gp100, tyrosinase, TRP-1, TRP-2, NY-ESO-1, CDK-4, β-catenin, MUM-1, Caspase-8, KIAA0205, HPVE7, SART-1, PRAME, and p15 antigens, members of the MAGE family, the BAGE family (such as BAGE-1), the DAGE/PRAME family (such as DAGE-1), the GAGE family, the RAGE family (such as RAGE-1), the SMAGE family, NAG, TAG-72, CA125, mutated proto-oncogenes such as p21ras, mutated tumor suppressor genes such as p53, tumor associated viral antigens (e.g., HPV16 E7), the SSX family, HOM-MEL-55, NY-COL-2, HOM-HD-397, HOM-RCC-1.14, HOM-HD-21, HOM-NSCLC-11, HOM-MEL-2.4, HOM-TES-11, RCC-3.1.3, NY-ESO-1, and the SCP family. Members of the MAGE family include, but are not limited to, MAGE-1, MAGE-2, MAGE-3, MAGE-4 and MAGE-11. Members of the GAGE family include, but are not limited to, GAGE-1, GAGE-6. See, e.g., review by Van den Eynde and van der Bruggen (1997) in *Curr. Opin. Immunol.* 9: 684-693, Sahin et al. (1997) in *Curr. Opin. Immunol.* 9: 709-716, and Shawler et al. (1997), the entire contents of which are incorporated by reference herein for their teachings of cancer antigens.

The cancer antigen/target molecule can also be, but is not limited to, human epithelial cell mucin (Muc-1; a 20 amino acid core repeat for Muc-1 glycoprotein, present on breast cancer cells and pancreatic cancer cells), MUC-2, MUC-3, MUC-18, the Ha-ras oncogene product, carcino-embryonic antigen (CEA), the raf oncogene product, CA-125, GD2, GD3, GM2, TF, sTn, gp75, EBV-LMP 1 & 2, HPV-F4, 6, 7, prostatic serum antigen (PSA), prostate-specific membrane antigen (PSMA), alpha-fetoprotein (AFP), CO17-1A, GA733, gp72, p53, the ras oncogene product, β-HCG, gp43, HSP-70, p17 mel, HSP-70, gp43, HMW, HOJ-1, melanoma gangliosides, TAG-72, mutated proto-oncogenes such as p21ras, mutated tumor suppressor genes such as p53, estrogen receptor, milk fat globulin, telomerases, nuclear matrix proteins, prostatic acid phosphatase, protein MZ2-E, polymorphic epithelial mucin (PEM), folate-binding-protein LK26, truncated epidermal growth factor receptor (EGFR), Thomsen-Friedenreich (T) antigen, GM-2 and GD-2 gangliosides, polymorphic epithelial mucin, folate-binding protein LK26, human chorionic gonadotropin (HCG), pancreatic oncofetal antigen, cancer antigens 15-3, 19-9, 549, 195, squamous cell carcinoma antigen (SCCA), ovarian cancer antigen (OCA), pancreas cancer associated antigen (PaA), mutant K-ras proteins, mutant p53, and chimeric protein $p210_{BCR-ABL}$ and tumor associated viral antigens (e.g., HPV16 E7).

The cancer antigen/target molecule of this invention can also be an antibody produced by a B cell tumor (e.g., B cell lymphoma; B cell leukemia; myeloma; hairy cell leukemia), a fragment of such an antibody, which contains an epitope of the idiotype of the antibody, a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR. In one embodiment, the cancer antigen of this invention can be a single chain antibody (scFv), comprising linked $V_H$, and $V_L$ domains, which retains the conformation and specific binding activity of the native idiotype of the antibody.

The present invention is in no way limited to the cancer antigens listed herein. Other cancer antigens be identified, isolated and cloned by methods known in the art such as those disclosed in U.S. Pat. No. 4,514,506, the entire contents of which are incorporated by reference herein.

Nonlimiting examples of a cancer of this invention include (in any combination) B cell lymphoma, T cell lymphoma, myeloma, leukemia, hematopoietic neoplasias, thymoma, lymphoma, sarcoma, lung cancer, non-Hodgkins lymphoma, Hodgkins lymphoma, uterine cancer, adenocarcinoma, breast cancer, pancreatic cancer, colon cancer, colorectal cancer, anal cancer, lung cancer, renal cancer, bladder cancer, liver cancer, prostate cancer, ovarian cancer, skin cancer, primary or metastatic melanoma, squamous cell carcinoma, basal cell carcinoma; brain cancer, angiosarcoma, hemangiosarcoma, head and neck carcinoma, thyroid carcinoma, soft tissue sarcoma, bone cancer, bone sarcoma, testicular cancer, uterine cancer, cervical cancer, gastrointestinal cancer, stomach cancer, esophageal cancer, and any other cancer now known or later identified (see, e.g., Rosenberg (1996) *Ann. Rev. Med.* 47:481-491, the entire contents of which are incorporated by reference herein).

In some embodiments of the methods of this invention, the target molecule can be an extracellular domain of a cell surface receptor (such as epidermal growth factor receptor family members (EGFR, HER2, HER3, HER4, etc.), c-MET, VEGFR, insulin receptor, insulin-like growth factor receptor, prostate specific membrane antigen, mesothelin, hepsin, an integrin, mucin (e.g., MUC16, etc.), a cell surface cluster of differentiation (CD) molecule, (e.g., CD20, CD22, CD30, CD33, CD44, CD56, etc.), and any combination thereof.

The present invention also provides a kit comprising a heptamer of this invention and/or a nucleic acid molecule of this invention and/or a vector of this invention and/or a cell of this invention and instructions for their use in the treatment of cancer in a subject and/or detection and/or localization of cancer cells and/or other diseased cells in a subject and/or diagnosis of cancer and/or other disorders (e.g., diabetes, asthma) in a subject.

EXAMPLES

Example 1

Multivalency of targeting ligands provides significantly increased binding strength to the target protein. Oligomerization of target-binding molecules has been used for the development of multivalent molecules. The present invention is directed to the development of a class of novel heptameric targeting ligands by fusing a target-binding domain with the multimerization domain of Archaeal RNA binding protein Sm1. All the fusion molecules were highly expressed in *E.* coli and the heptameric targeting ligands were formed through a highly efficient self-assembly process. The resulting heptameric structure was highly stable and resistant to protease-mediated digestion and heat- or SDS-induced denaturation. The target-binding specificity of each heptamer is well maintained as the corresponding monomeric targeting ligand. All of the heptamers showed significantly enhanced binding strength to their target receptor protein by more than 1000-fold. The non-toxicity of each heptameric molecule was demonstrated by cellular studies. This system allows for the conversion of many target-binding protein domains or short peptides into their heptameric forms with avidity and high stability that could have significant applications in biochemical and biomedical fields.

Cell Culture

All cell lines including EGFR-positive A431, EGFR-negative Jurkat, HER2-positive SKOV3, HER2-negative MCF7, PSMA-positive LNCaP and PSMA-negative PC3 cancer cell lines were obtained from the UNC Tissue Culture Facility. All cell lines were maintained by serial passage at 37° C. in an appropriate medium containing 10% fetal bovine serum.

Plasmid Construction

Codon optimized DNA sequences that code Archaea Sm1, $Z^{EGFR}$ and $Z^{HER2}$, respectively, were synthesized by GenScript (Piscataway, N.J.). The design for each monomeric and heptameric targeting ligand is shown in FIG. 1. After PCR amplification, the gene products were purified and digested with Nco I and Xho I. The resulting digested fragments were cloned into the corresponding sites (Nco I and Xho I) of pET28b (Novagen). The cloned plasmids were confirmed by sequencing.

Protein Expression and Purification

Each expression vector was transformed into E. coli BL21 (DE3) Rosseta cells. The positive clones were selected on LB plate containing kanamycin (50 µg/ml) and chloramphenicol (34 µg/ml). The single colony was picked and grown in 5 ml LB overnight at 37° C. The overnight grown cells were added into 500 ml LB containing kanamycin and chloramphenicol. The cells were grown at 37° C. until O.D. 600 reached 0.5 to 1.0. 0.5 mM IPTG was added and expression was induced at 22° C. for 12 hours. After induction, the cells were spun down at 3000 g for 10 min at 4° C., and the pellet was stored at −20° C. prior to purification. To purify each monomeric or heptameric molecule, the cell pellet was resuspended in buffer A (25 mM HEPES pH7.4 and 300 mM NaCl) and sonicated for 1 min each time for a total of 5 times. After breaking the cells, the soluble fraction was recovered by centrifugation at 12,000 g for 10 min at 4° C. The resulting soluble fraction was loaded onto a TALON metal affinity column (Clontech, Mountainview, Calif.) pre-equilibrated with buffer A. About 20 column volumes of buffer A were used for initial washing followed by extensive washing with buffer B (buffer A and 20 mM imidazole). The protein of interest was eluted with buffer C (buffer A and 200 mM imidazole) in 1 column volume. The quality of the purified proteins was examined by SDS-PAGE.

Analytical Ultracentrifugation

Highly purified monomeric or heptameric molecules were prepared in a buffer containing 25 mM HEPES pH7.4 and 150 mM NaCl. The solution was centrifuged at 10,000 rpm for 24 hours at 20° C. The absorbance at 280 nm was recorded every 2 hours during centrifugation. Each resulting absorbance was fit into a self association model to calculate the molecular weight.

FITC Labeling of Monomeric and Heptameric Targeting Ligands

Each monomeric and heptameric molecule was labeled with fluorescein isothiocyanate (FITC) (ACROS organics) in a 50 mM borate buffer (pH 8.5). Briefly, one milligram of each protein was reacted with 25 molar excess of FITC and incubated at room temperature for two hours. The resulting mixture was quenched by the addition of 100 mM Tris-HCl (pH 8.8) at room temperature for one hour. Unreacted free FITC molecule was removed by passing through a NAP-10 column (GE Healthcare). Extensive dialysis was performed overnight using 5 k dialysis membrane (GE Healthcare) to further remove the residual FITC.

Cell Surface Binding Analysis

About $2 \times 10^4$ cells were seeded on coverslides and allowed to grow in an appropriate medium for 16 hours. The resulting coverslides were washed with PBS twice, followed by incubation with different concentrations of FITC-labeled monomeric or heptameric targeting ligand for 30 min at room temperature. The coverslides were washed with PBS three times and visualized with a Zeiss LSM 510 confocal microscope.

BIAcore Analysis

BIAcore 2000 (BIAcore AB, Uppsala, Sweden) was used for surface plasmon resonance (SPR) analysis. Purified extracellular domain of recombinant human EGFR ECD-Fc, HER2 ECD-Fc, and PSMA were diluted in 10 mM sodium acetate pH 5.0 and immobilized on a CM5 sensor chip (GE healthcare) by amine coupling according to the manufacturer's instruction (about 2,500 resonance unit). Various concentrations of monomeric and heptameric targeting ligands were injected onto the flow cell in an HBS-P buffer (10 mM HEPES pH7.4, 150 mM NaCl, and 0.005% surfactant P20) at a flow rate of 20 µl/min or 30 µl/min. The dissociation constants ($K_d$) were calculated using BIAevaluation software (BIAcore) by fitting data on one to one Langmuir binding model.

Circular Dichroism (CD) Spectroscopy

Highly purified monomeric and heptameric proteins were prepared in 10 mM phosphate buffer (pH7.5) and used for CD scanning with an AVIV model 202-01 spectropolarimeter. To determine thermal stability, spectra were recorded by gradually increasing temperature from 25° C. to 94° C.

Protease Resistance

About 5 to 10 µg of proteins were incubated with thermolysin (10 ng of thermolysin per 1 µg of protein). The protease digestions were performed in an HBS buffer (10 mM HEPES pH7.4 and 150 mM NaCl) at 25° C., 37° C., 42° C., and 60° C., respectively, for 20 min. After incubation, the resulting mixture was applied to SDS-PAGE to examine protein degradation.

Co-Localization Studies

A431 and SKOV3 cells were seeded onto coverslides and grown for 16 hours at 37° C., and incubated with 10 nM or 100 nM of FITC-labeled heptameric $Z^{EGFR}$ and $Z^{HER2}$ for 2 hours at 37° C. After removing unbound heptamers by washing, the cells were fixed with 2% paraformaldehyde in PBS for 15 min at room temperature. After fixation, cells were washed with PBS three times. For immunostaining, blocking solution (PBS with 5% BSA and 0.3% Triton X-100) was added for 1 hour at 4° C. Anti-EEA1 rabbit monoclonal antibody (Cell signaling Technology, Danvers, Mass.) was incubated (1:200) with the cells overnight at 4° C. The resulting cells were rinsed with PBS three times. After incubation with secondary antibody Alexa Fluor 555 conjugated anti Rabbit IgG (Cell signaling technology, Danvers, Mass.) for 1 hour at 4° C., the corresponding cells were rinsed with PBS three times followed by adding antifade reagent to examine the cells with confocal laser microscopy.

MTS Assay

A CellTiter96 Aqueous Non-Radioactive Cell Proliferation Assay kit from Promega (Madison, Wis.) was used for MTS assay. Approximately $10^4$ cells were seeded on each well in a 96-well plate and grown for 16 hours at 37° C. Each heptameric molecule was incubated with the cells for 24 hours and Cis-platinum (II) diamine dichloride (cisplatin, CDDP) (Sigma-Aldrich Chemical Co) was used as positive control. 20 µl of MTS/PMS solution was added into each well followed by incubation for 4 hours at 37° C. The absorbance at 490 nm was recorded using an ELISA plate reader.

Design of Self-Assembled Heptameric Targeting Ligands

The general strategy used to develop the heptameric targeting ligands is to fuse a target-binding short peptide or small protein domain through a hinge linker with the approximately 70 residue (e.g., about 50-80 residue) highly stable AF-Sm1 domain that can efficiently self-assemble into a parallel heptameric complex (FIG. 1). In the previous self-association approach for the generation of trimeric and pentameric complexes[8,10,15], additional cysteine residues were introduced to stabilize the oligomeric structure through the formation of inter-molecular disulfide bonds. However, undesired disulfide bonds could be formed that result in incorrect folding, aggregation, and loss of target-binding properties'. In this heptameric complex, no cysteine residue is present in the whole construct, ruling out the possibility of forming disulfide-induced aggregation or misfolding. To test whether functional heptameric targeting ligand can be readily generated using this strategy, an EGFR- or HER2-binding Z domain that does not contain any cysteine residue[16,17] was used to facilitate the self-assembly process. In addition, studies were carried out to examine whether heptameric target-binding homing peptides can be generated using the same strategy (FIG. 1B). In this case, the AF-Sm1 heptamerization domain was fused with a 12 amino-acid short peptide WQPDTAHHWATL whose dimeric form has been demonstrated to bind to PSMA[18]. To compare the monomeric and the corresponding heptameric forms, the monomeric targeting ligand was constructed without the heptameric domain. In the case of the monomeric PSMA-binding peptide, a truncated, nonfunctional Sm1 domain was used since the 12-residue peptide is not suitable for expression in E. coli. A truncated heptameric domain was designed by removing C-terminal 23 residues that are important for intermolecular interaction based on the crystal structure[14].

Figure 2:
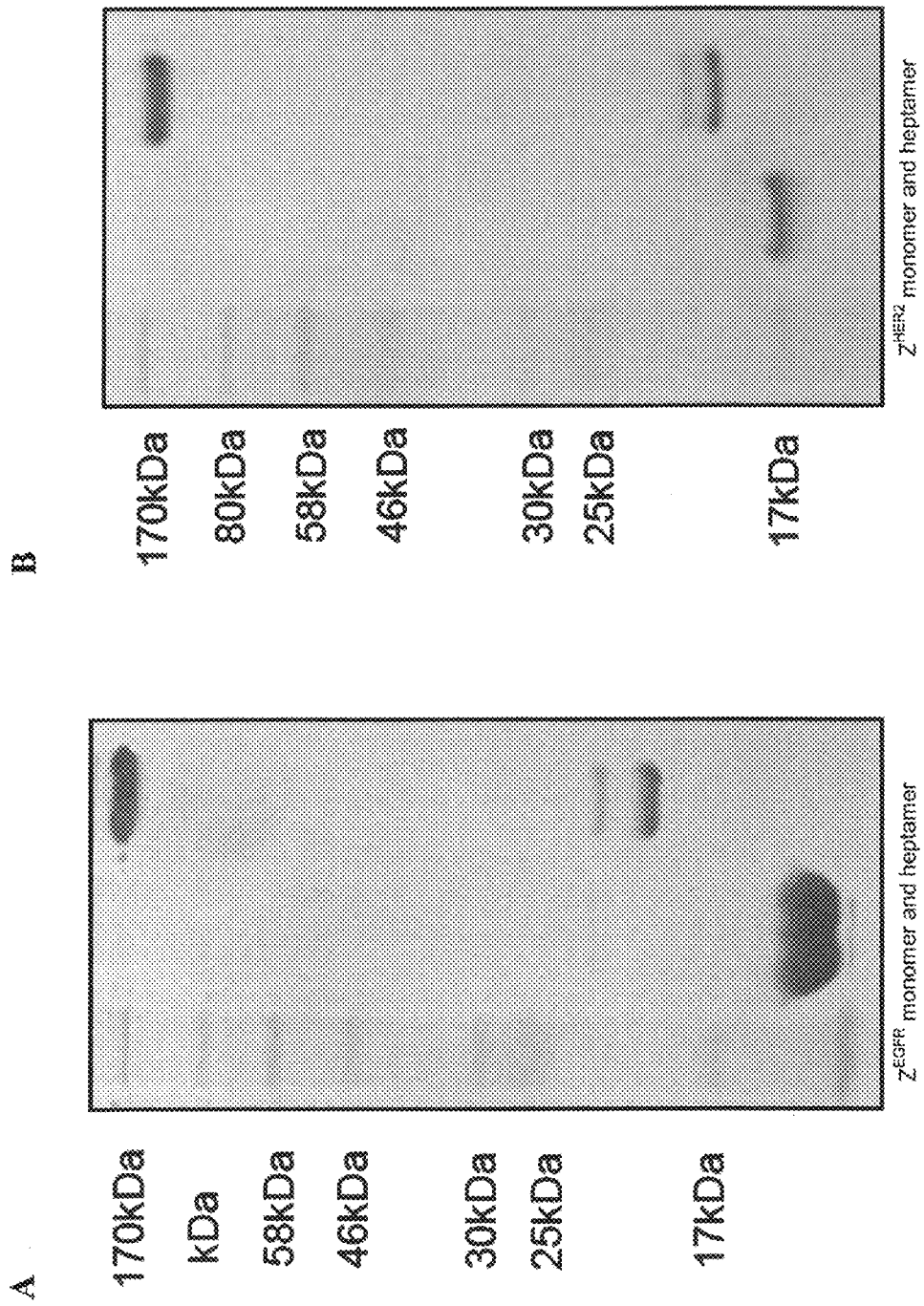
FIGS. 2A-C. Purification of monomeric and heptameric molecules. 10% SDS-PAGE was run for checking purity of each of the monomer and heptameric molecules after purification of each protein was performed with metal affinity column chromatography.
Figure 2C:
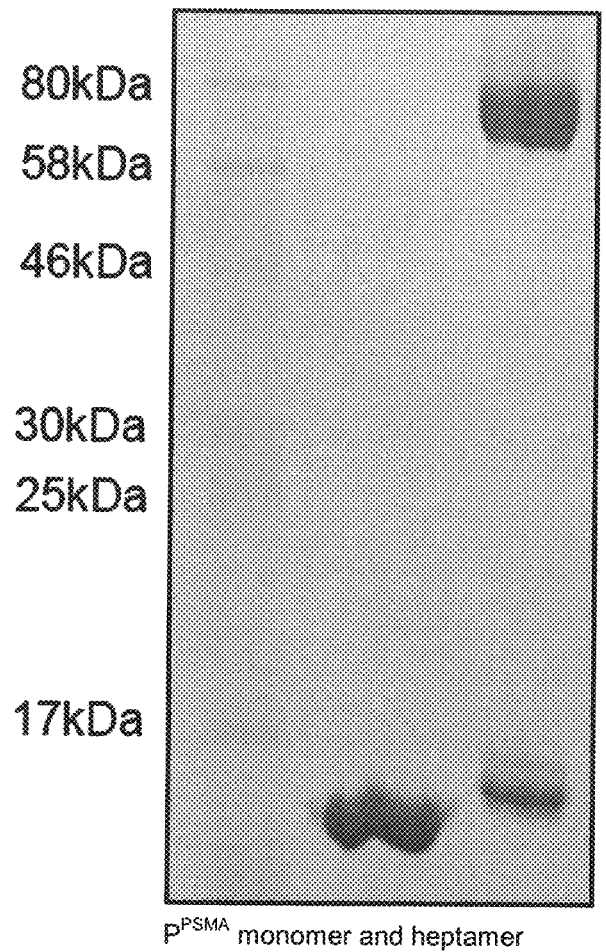

Purification of Monomeric and Heptameric Molecules and Molecular Weight Determination of the Heptameric Molecules All of the monomeric and heptameric molecules were purified to near homogeneity based on SDS-PAGE using metal affinity column chromatography (FIG. 2). It is evident that all of heptameric molecules are very stable in the presence of SDS and show unusual heat resistance. Both the monomeric and heptameric bands are present in the SDS-PAGE, suggesting that the purified heptamer co-existed with its monomer in non-denaturing condition.

Figure 3A:
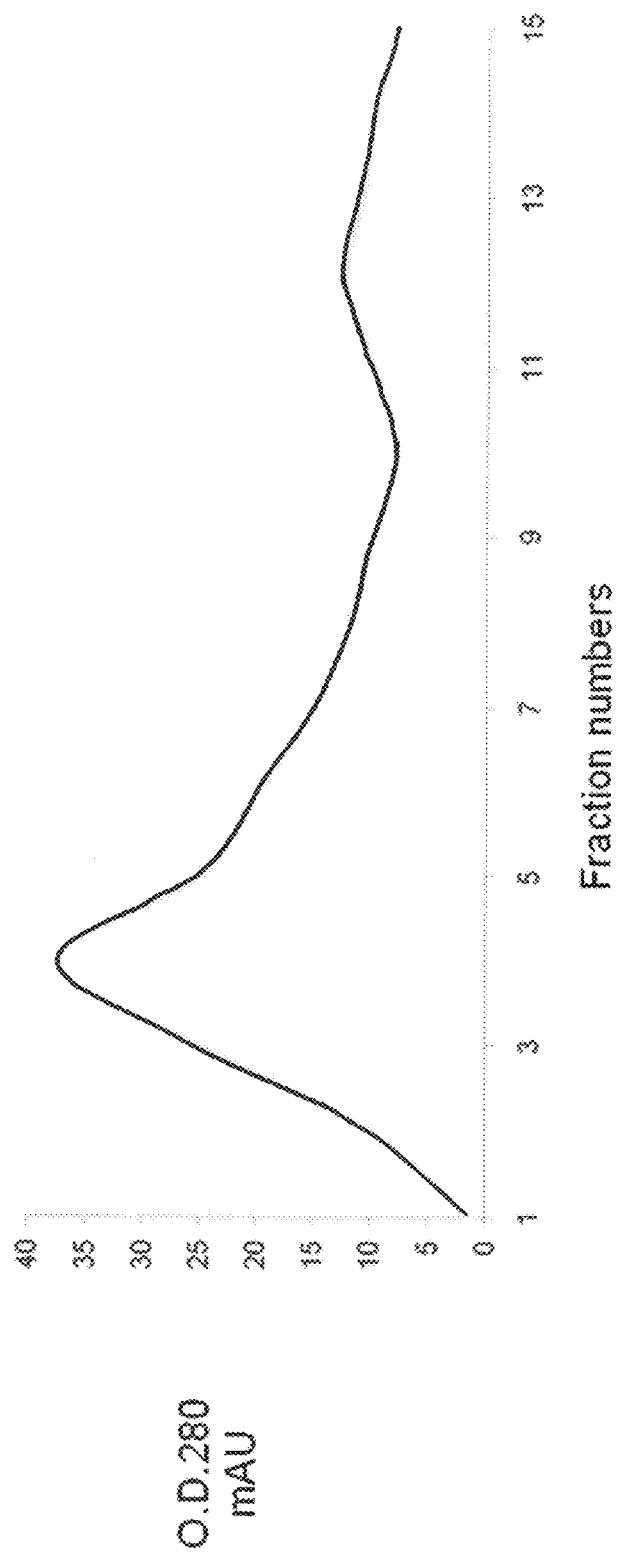
FIGS. 3A-C. Elution profile and SDS-PAGE of size exclusion chromatography. Affinity purified heptameric molecules were loaded on a Superdex-75 column and purified with a flow rate at 0.4 mL/min. Each fraction collected was about 400 ul, and 10 ul of each fraction was run on 10% SDS-PAGE.
Figure 3:
Figure 3:
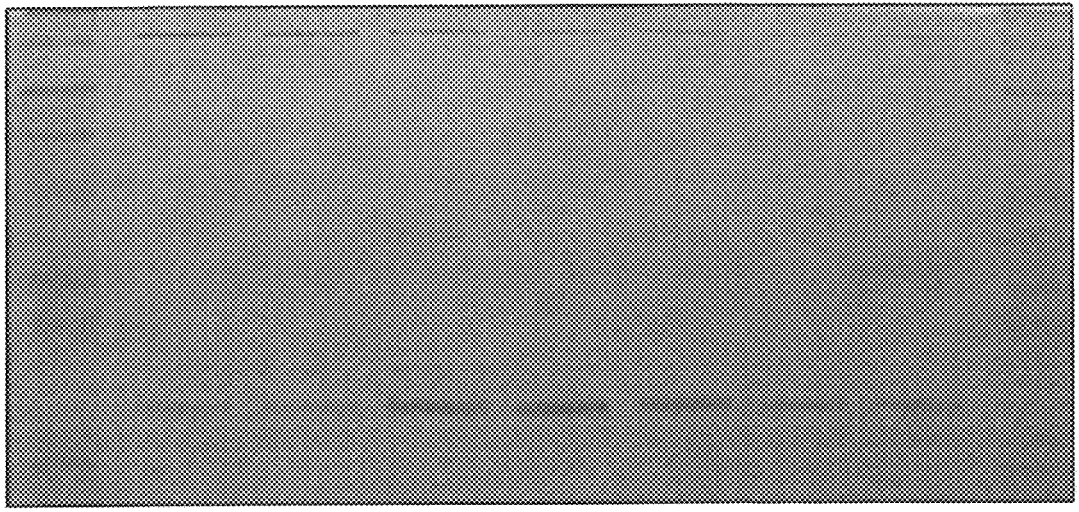
Figure 4:
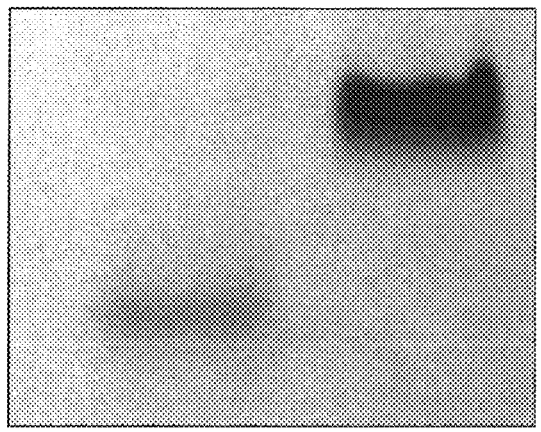
FIGS. 4A-C. Tris native gel of each monomer and heptameric molecules. Purified monomer and heptameric molecules, (A) $Z^{EGFR}$ monomer and heptamer; B) $Z^{HER2}$ monomer and heptamer; and C) $P^{PSMA}$ monomer and heptamer, were run on an 8% tris native gel. Heptameric molecules were purified using FPLC with a Superdex 75 column.
Figure 4:
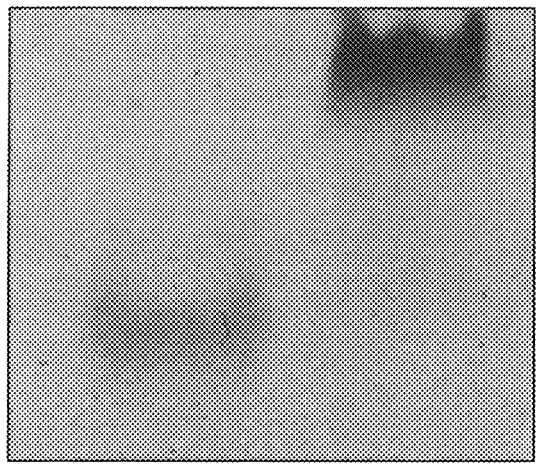
Figure 4:
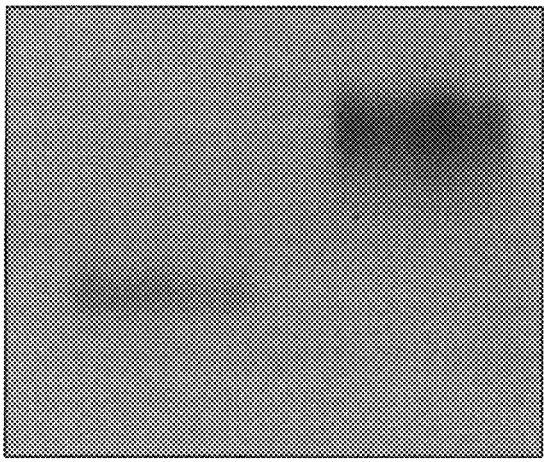
Figure 5:
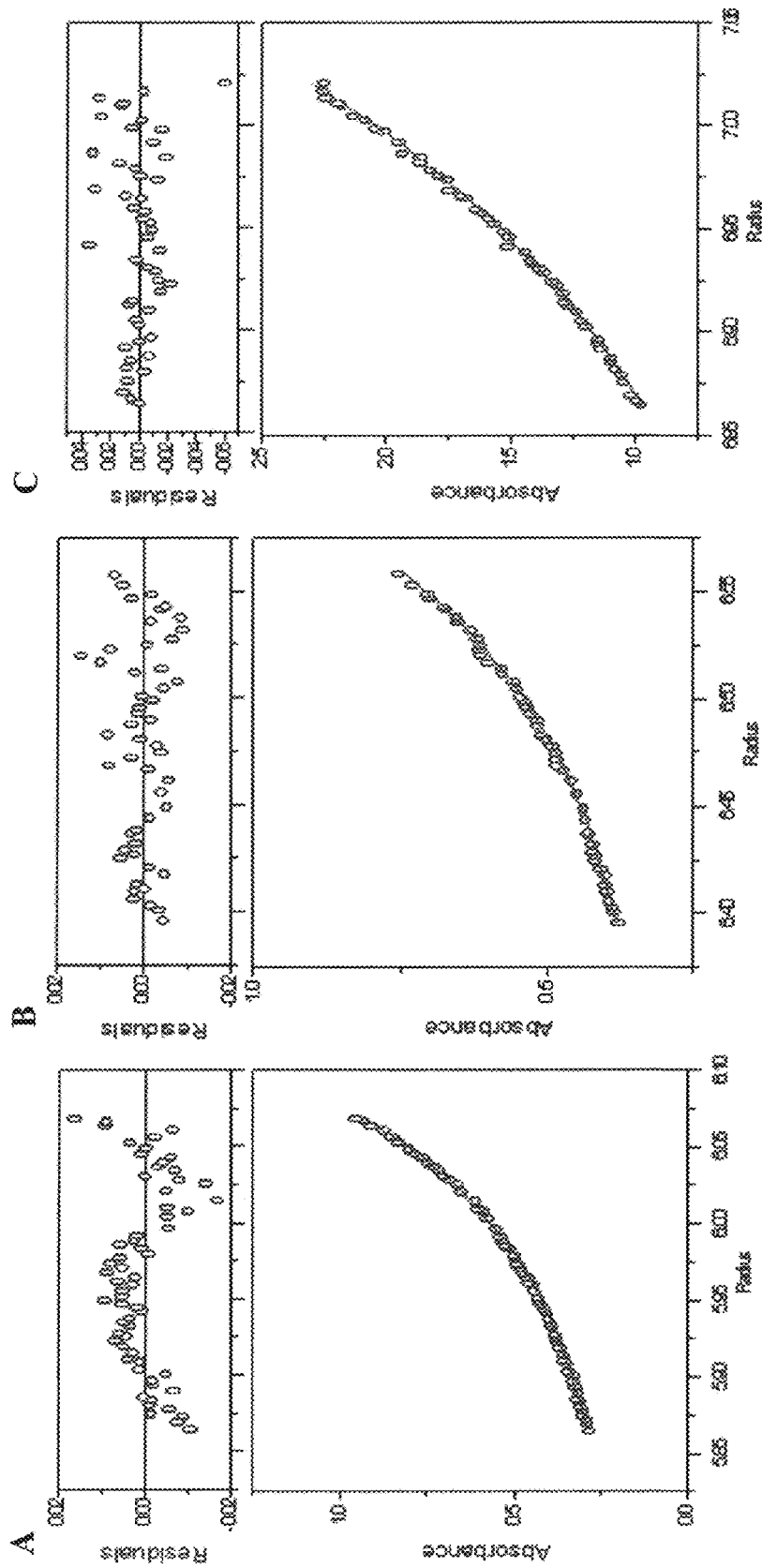
FIGS. 5A-C. Analytical ultracentrifugation. Purified A) $Z^{EGFR}$, B) $Z^{HER2}$, and C) $P^{PSMA}$ heptameric proteins were centrifuged at 10,000 rpm for 20 hours. Absorbances at 280 nm were recorded every two hours.

To remove the monomeric form, the heptameric molecule was further purified with size exclusion chromatography using Superdex-75. Heptameric $Z^{EGFR}$ showed three major peaks in the elution profile. As shown in FIG. 3, the early elution fractions contained the pure heptamer while the later elution fractions contained a mixture of monomeric and heptameric forms. Due to the strong denaturing nature of SDS-PAGE, it is likely that some less stable heptamers are converted back to the monomeric form. To address this problem, the early elution fractions, in which the vast majority of the proteins are in the heptameric form, were examined by using non-denaturing native gels. As shown in FIG. 4, the heptameric molecule was present without any other bands. PSMA heptamer fraction from metal affinity purification only existed as heptamer in native gel. This result indicates that the heptameric molecules can be readily purified by using size exclusion chromatography. To confirm the heptameric states, analytical ultracentrifugation was used to determine the molecular weights of these heptameric molecules. As illustrated in FIG. 5, the three putative heptameric targeting ligands have molecular weights at 134 kDa, 132 kDa, and 69 kDa, respectively, indicating that they are indeed present as heptameric forms.

In Vitro Binding and Determination of the Binding Affinity

To examine the binding strength of the heptameric targeting ligands, surface plasmon resonance (BIAcore) was used to determine the target-binding parameters of each of the monomeric and heptameric molecules. Here, the extracellular domains of EGFR, HER2, and PSMA that are immobilized on the surface of CM5 biosensor chips were used. The binding constants $K_d$ of monomeric $Z^{EGFR}$ and $Z^{HER2}$ (2.6 nM) (Table 1) are similar to that reported in the literature (~5 nM)[17]. Significantly enhanced binding strength (~29 pM and 2 pM) was shown when heptameric $Z^{EGFR}$ or $Z^{HER2}$ was used. In the latter case, there was more than 1000-fold increase compared to the monomeric form. PSMA heptameric molecules bind marginally to the corresponding receptor while PSMA monomer did not bind to receptor although 100 uM of protein was injected on the flow cell. These results suggest that heptameric targeting ligands are superior to monomeric forms in terms of target binding strength.

Figure 6:
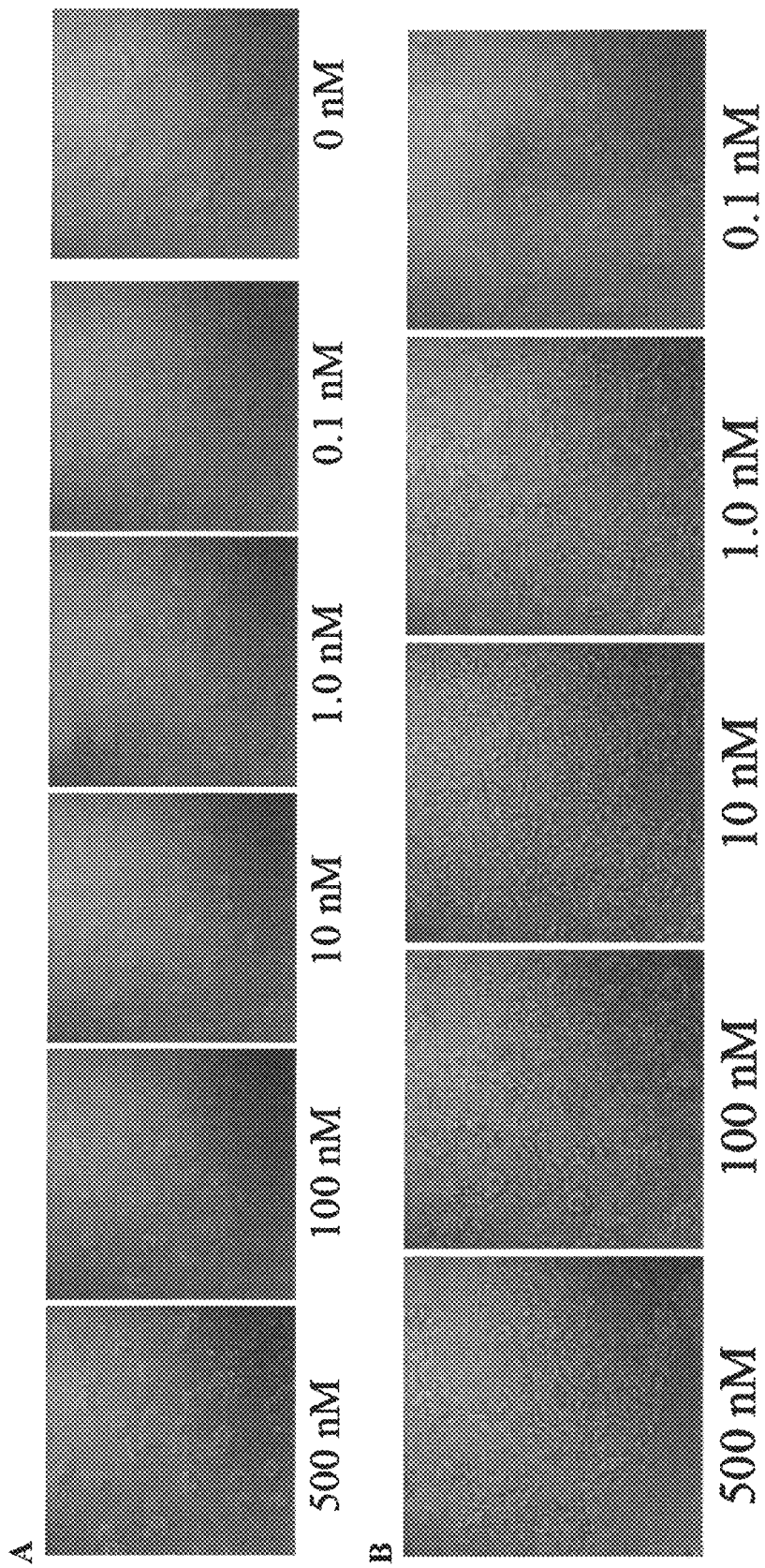
FIGS. 6A-B. Cell surface binding. (A) A431 cells (EGFR positive cells) were grown on coverslides. Different concentrations of FITC labeled $Z^{EGFR}$ monomeric and heptameric molecules were incubated with A431 cells for 30 min at 25° C. (B) LNCaP cells (PSMA positive cells) were grown on coverslides. FITC labeled $P^{PSMA}$ monomeric and heptameric molecules were incubated with LNCaP cells for 30 min at 25° C.

Binding of the Monomeric and Heptameric Targeting Ligands with the Cell Surface Biomarkers To compare the target-binding properties of the monomeric and heptameric targeting ligands, each of the monomeric and heptameric molecules were labeled with FITC and used for the cell binding assay with cancer cells expressing the biomarker of interest. For EGFR-binding $Z^{EGFR}$, A431 cells that overexpress EGFR were used, while EGFR-negative Jurkat cells were used as negative controls. No detectable fluorescence signal was observed for both $Z^{EGFR}$ monomer and heptamer when Jurkat cells were used, even when the concentration of the targeting ligands was as high as 100 nM. However, the signal was evident in both $Z^{EGFR}$ monomer and heptamer when EGFR-expressing A431 cells were used. It appears that the cell-binding of the heptameric $Z^{EGFR}$ is much stronger than the monomeric form. As shown in FIG. 6, the concentration of $Z^{EGFR}$ heptamer required to achieve the same cell-binding signals was at least 1000-fold lower than that of the monomer, and as low as 0.1 nM $Z^{EGFR}$ heptamer was enough to obtain reasonable target-binding. These results indicate that heptameric molecules bind to the cell surface biomarkers much more tightly than the monomeric form, presumably due to the multivalent effect.

Thermal Stability and Protease Resistance

Figure 8:
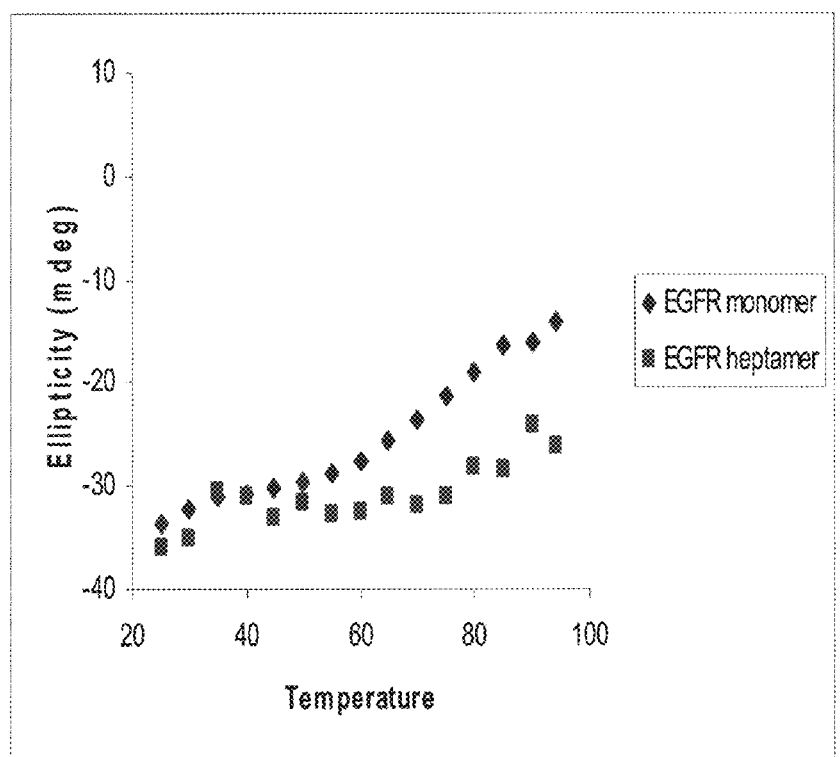
FIGS. 8A-C. Heat induced denaturation curve using circular dichroism. A) $Z^{EGFR}$ monomeric and heptameric molecules, B) $Z^{HER2}$ monomeric and heptameric molecules, and C) $P^{PSMA}$ monomeric and heptameric molecules were prepared in 10 mM phosphate buffer. Temperature was increased from 25° C. to 94° C. Spectra were recorded at various temperatures. The ellipticity at 220 nm was used for the analysis.
Figure 8:
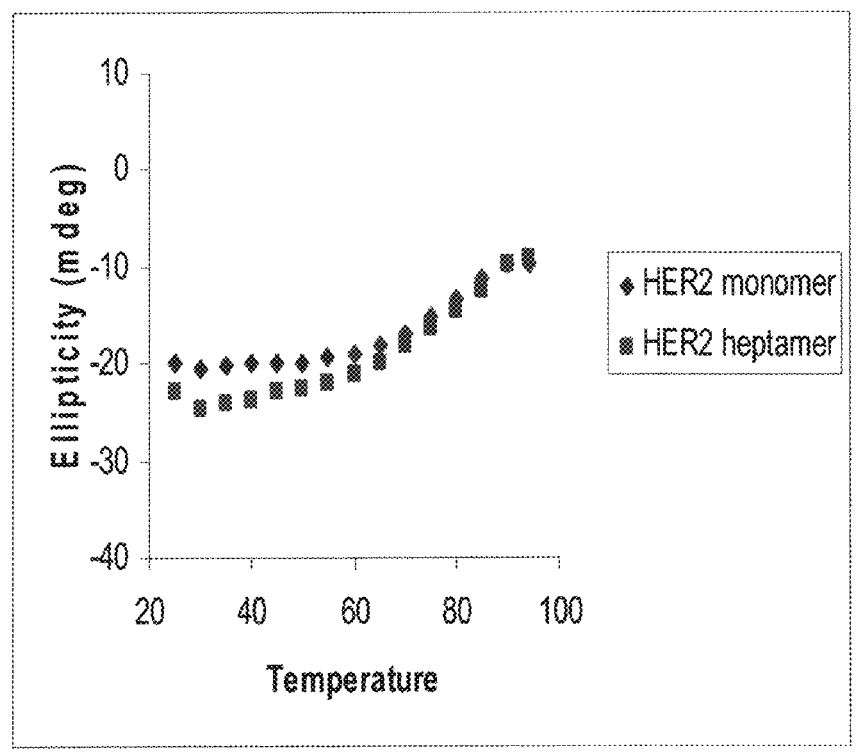
Figure 8C:
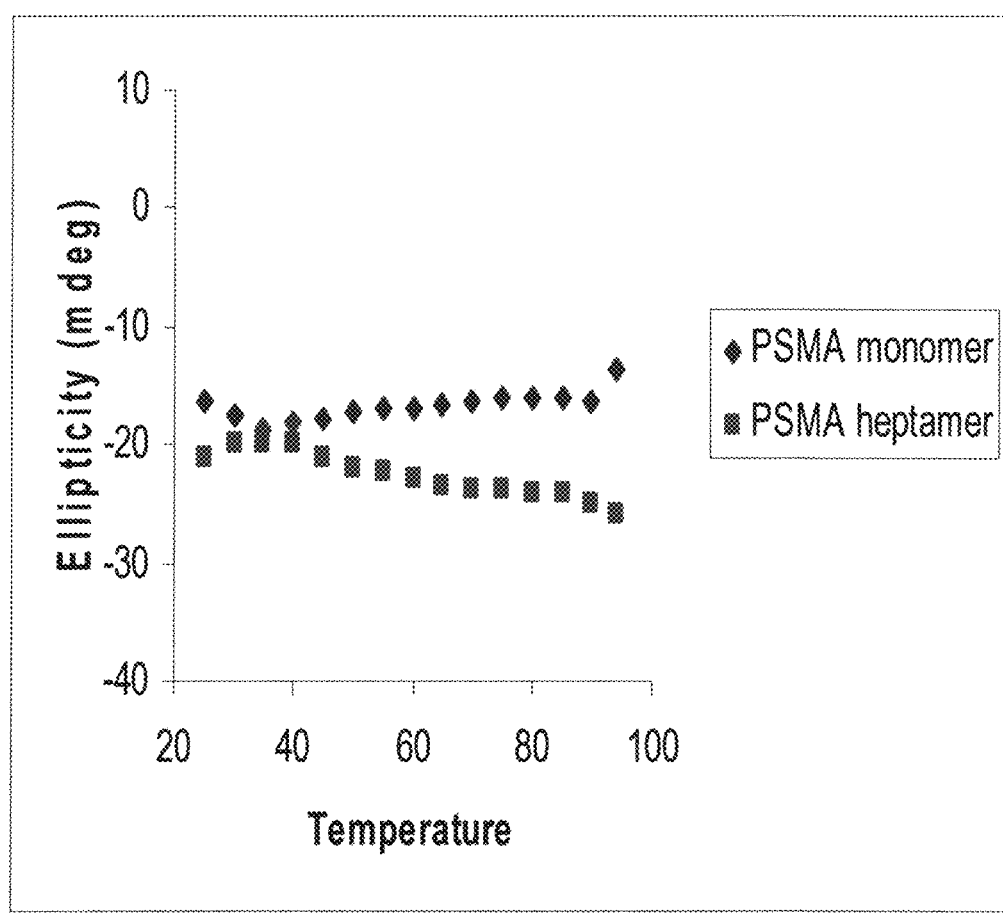

To determine the heat stability of the heptameric targeting ligands, circular dichroism (CD) analysis was performed using highly purified monomeric and heptameric molecules. As shown in FIG. 8, $Z^{EGFR}$ and $Z^{HER2}$ monomeric and heptameric molecules were stable up to 60° C. while PSMA monomer and heptamer is stable up to 90° C. These results indicate that the heptamer scaffold is resistant to heat induced denaturation. The target-binding moiety of the PSMA heptamer contains only 12 amino acids that should not have any ordered structures. Therefore, the observed stability is a good indication of the heptameric scaffold.

Figure 9A:
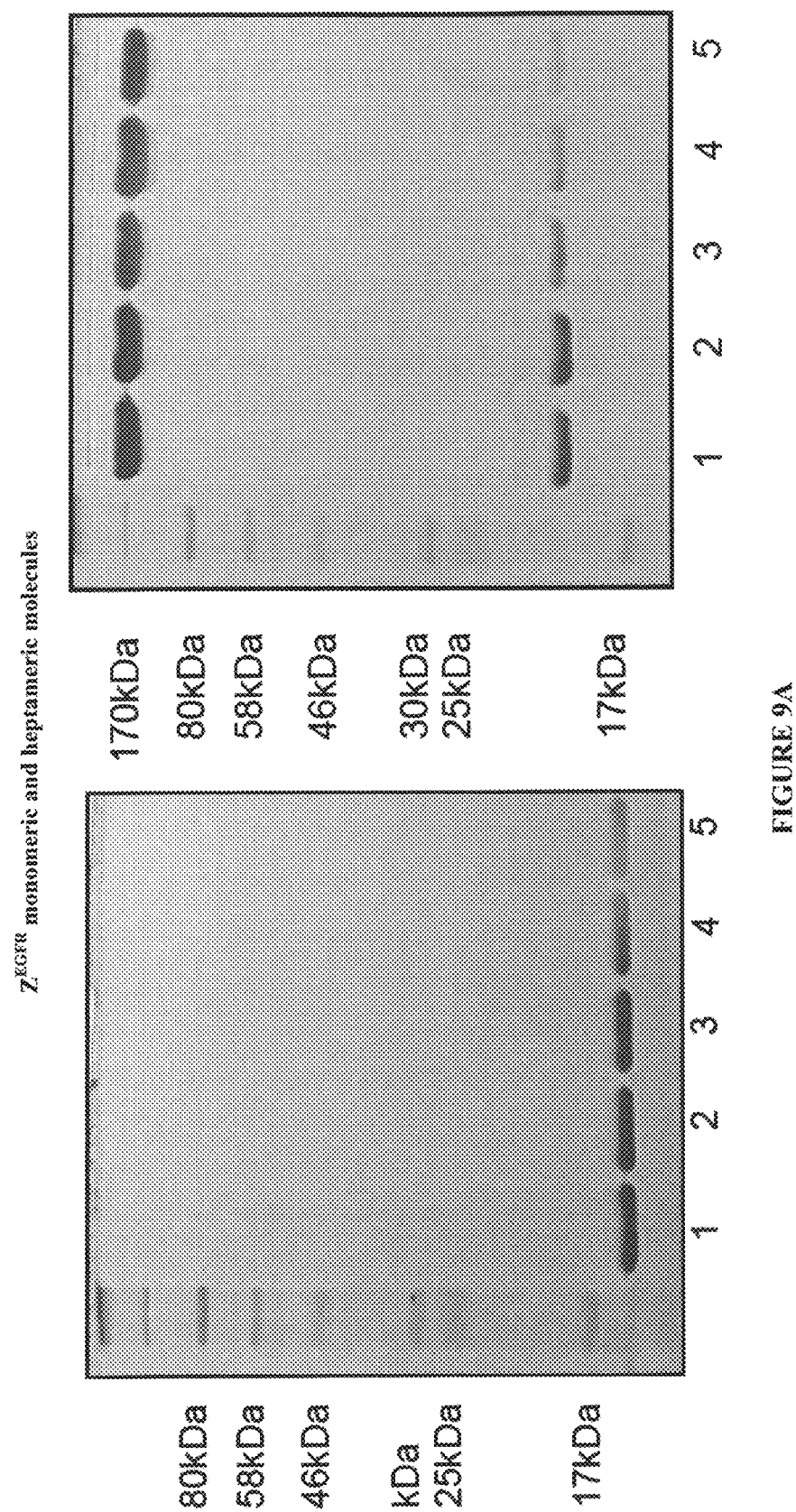
FIGS. 9A-C. Thermolysin resistance. Purified proteins were incubated with thermolysin at different temperatures for 20 min (lane 2: 25° C., lane 3: 37° C., lane 4: 42° C., and lane 5: 60° C.). The same amount of protein was loaded on SDS-PAGE without incubation of thermolysin at lane 1.
Figure 9B:
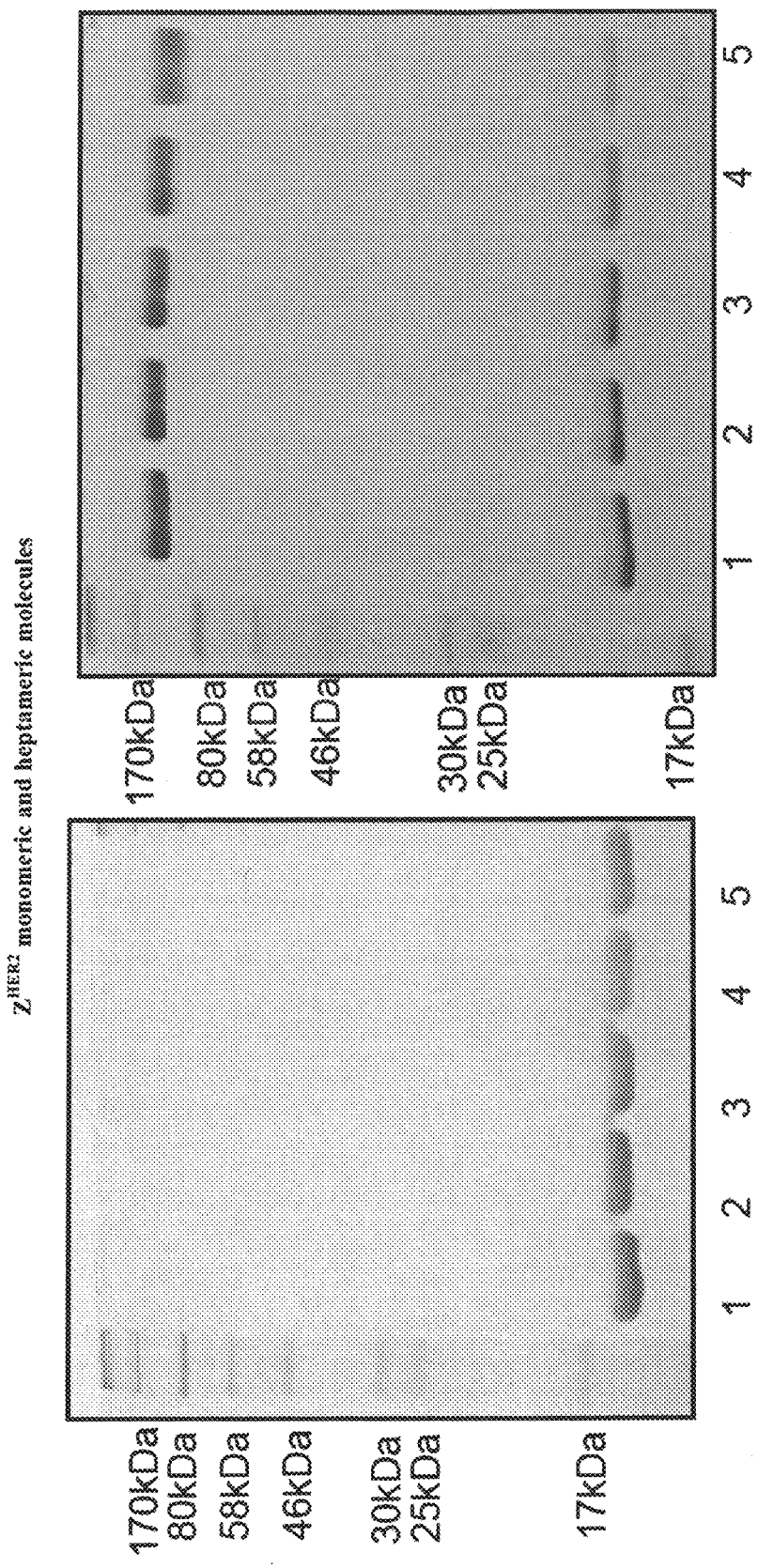
Figure 9C:
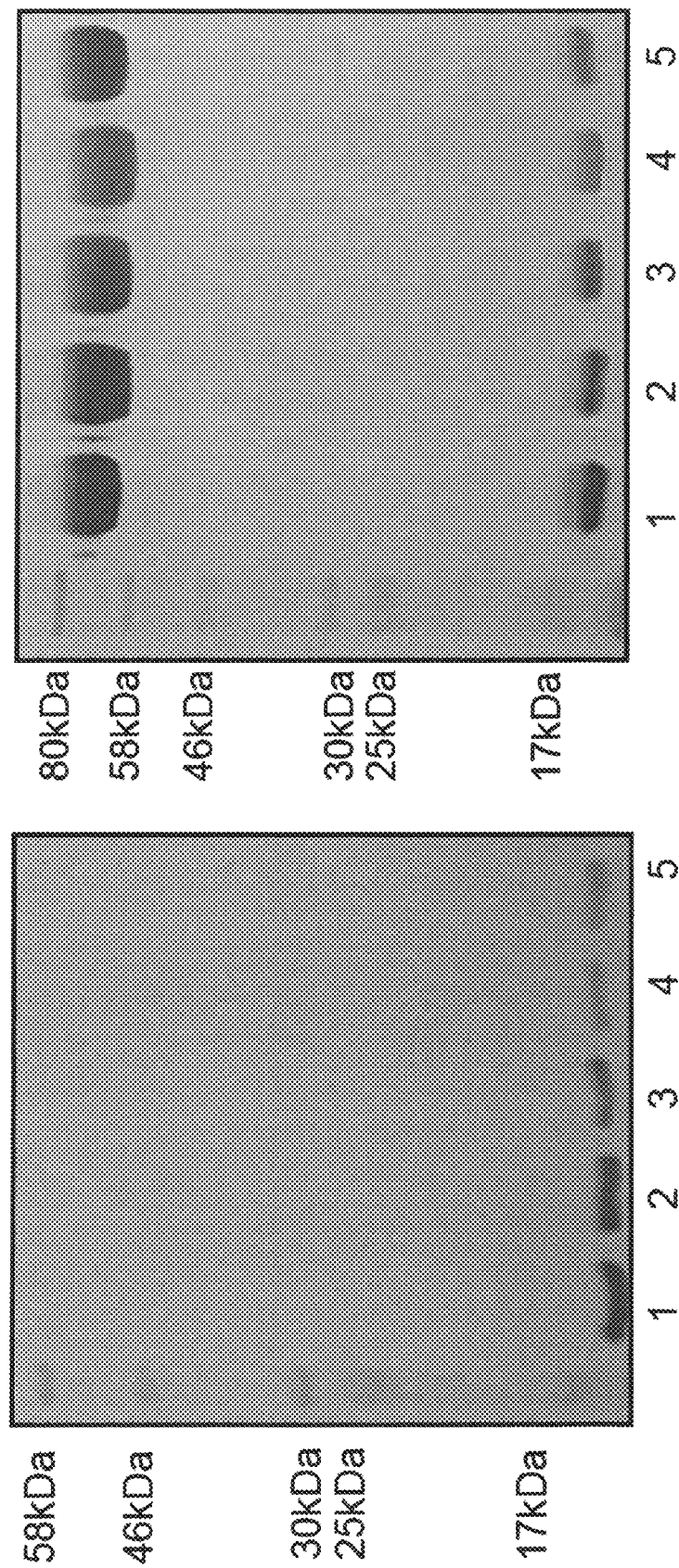

Protein degradation by proteases is one of the major problems that limit the applications. To investigate this property, protease-mediated digestion of the heptameric targeting ligands was performed by using thermostable metallopeptidase thermolysin[19]. Significantly, all of the heptameric molecules were as resistant to thermolysin digestion as that of the corresponding monomers, even when the temperature is as high as 60° C. (FIG. 9), suggesting these heptameric targeting ligands can be used under harsh conditions.

Heptameric $Z^{EGFR}$ is Co-Localized with Early Endosome Antigen 1 (EEA1)

To apply heptameric targeting ligands in the targeted delivery of imaging or therapeutic agents, it is important to know their subcellular localization once they are internalized. It is well known that the binding of EGF to its receptor EGFR promotes the internalization of the receptor through the endocytic pathway[20]. EGF-EGFR is strongly associated with EEA1 that is enriched in endosomes[20]. Recently, it was reported that EGFR-binding $Z^{EGFR}$ was internalized and affected the intracellular signaling pathway by inducing the phosphorylation of Akt and Erk in the A431 cells[21,22]. To investigate the internalization properties of heptameric $Z^{EGFR}$, the fluorescently labeled targeting ligand was incubated with A431 cells at 37° C. to promote its internalization. As illustrated in FIG. 16, heptameric $Z^{EGFR}$ was efficiently internalized and mostly co-localized with EEA1. It appears that the internalization efficiency of heptameric $Z^{HER2}$ is lower compared to that of heptameric $Z^{EGFR}$, although it is also co-localized with EEA1 in endosomes as shown in FIG. 16.

Cellular Toxicity of the Heptameric Targeting Ligands

Figure 10A:
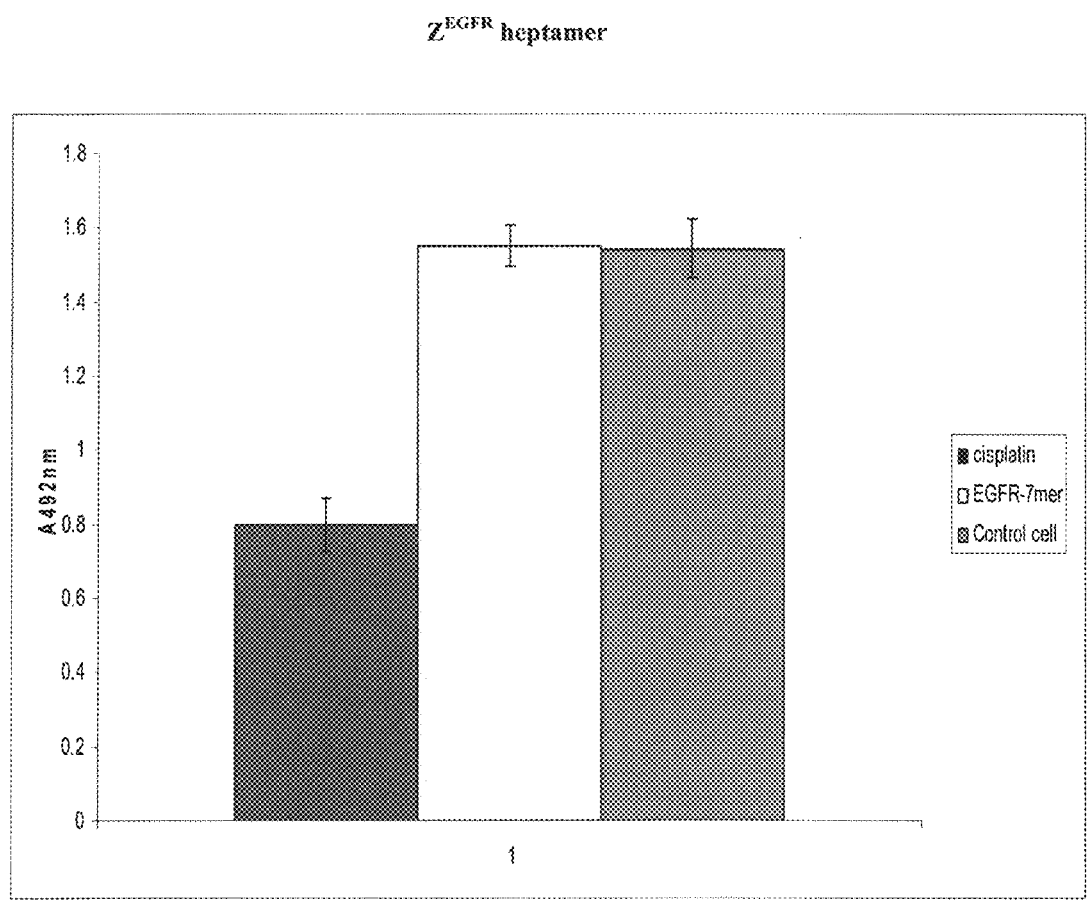
FIGS. 10A-C. Cellular toxicity of heptameric molecules. A) A431 (EGFR), B) SK-OV3 (HER2), and C) LNCaP cells were incubated with 1 uM of each of the heptamer molecules for 24 hours at 37° C. Cisplatin (10 uM) was also incubated with each of the cells as a positive control. Cells without incubation with any proteins or cisplatin were used as a negative control.
Figure 10B:
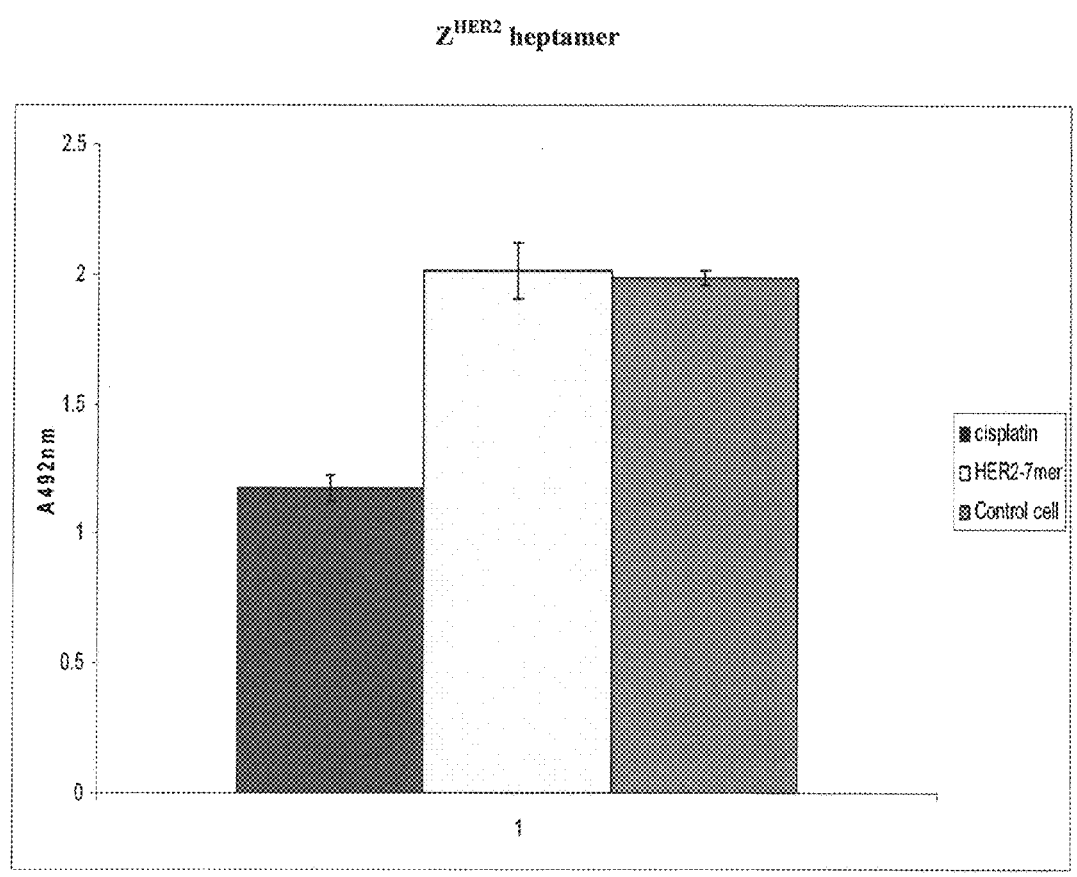
Figure 10C:
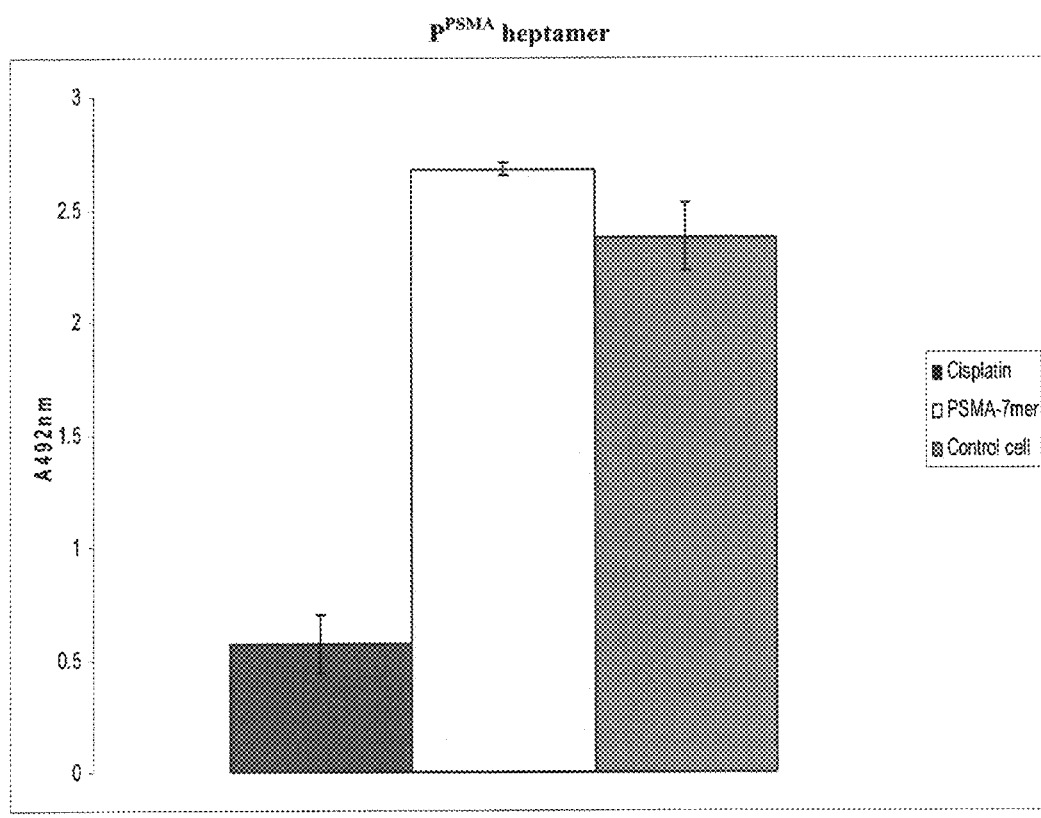

An ideal targeting ligand should be non-toxic itself to normal cells. MTS assays were used to determine the possible cellular toxicity of these heptameric targeting ligands by incubating a high concentration of heptamer (1 µM), while anti-cancer drug cisplatin was used as a positive control. FIG. 10 illustrates that none of the heptamers showed any obvious toxicity. These results indicate that these heptameric targeting ligands themselves are not toxic under the conditions applied.

In this study, three heptameric targeting ligands were designed and developed for cancer biomarkers EGFR, HER2, and PSMA. All of the heptameric targeting ligands can be purified as soluble proteins that do not require refolding[16,17]. The heptameric molecules are very soluble, allowing for the generation of 10 to 20 mg of highly purified proteins from 1 liter of bacterial culture. In terms of stability, all of the heptameric molecules showed resistance to heat induced denaturation and proteolytic degradation. Significantly, the heptameric molecules were efficiently self-assembled, with most existing as a heptameric form under native conditions. Compared to the corresponding monomeric form, the binding strength of the heptameric form was dramatically enhanced (up to 1000 fold). Most of the internalized heptameric molecules were co-localized with the early endosomes. In addition, the heptameric targeting ligands are nontoxic. Unlike the pentameric targeting ligands that rely on disulfide bonds to maintain oligomeric state and therefore exist as a mixture of mono, di, tri, tetra, and pentameric forms, the heptameric targeting ligands described herein do not contain any cysteine residues and exist predominately as the heptameric form without any noticeable intermediate forms. The lack of internal cysteine makes it possible to engineer a C-terminal cysteine that allows for site specific conjugation with other molecules. All these features indicate that such heptameric targeting ligands are useful as carriers for targeted delivery of imaging and/or therapeutic molecules.

REFERENCES FOR EXAMPLE 1

1. Deyev, S. M. & Lebedenko, E. N. (2008). Multivalency: the hallmark of antibodies used for optimization of tumor targeting by design. *Bioessays* 30, 904-918.
2. Pluckthun, A & Pack, P (1997). New protein engineering approaches to multivalent and bispecific antibody fragments. *Immunotechnology* 3, 83-105,
3. Crothers D. M. & Metzger H (1972). The influence of polyvalency on the binding properties of antibodies. *Immunochemistry* 9, 341-357.
4. Trejtnar F & Laznicek, M (2002). Analysis of renal handling of radiopharmaceuticals. *Q J Nuc Med* 46, 181-194.
5. Borsi L., Balza E, Carnemolla, B., Sassi F., Castellani P (2003). Selective targeted delivery of THF alpha to tumor blood vessels. *Blood* 102, 4384-4392.
6. Pack, P., Muller, K., Zahn, R.& Pluckthun, A. (1995). Tetravalent miniantibodies with high avidity assembling in *Escherichia coli*. *J Mol Biol* 246, 28-34.
7. Kubetzko, S., Balic, E., Waibel, R., Zangemeister-Wittke, U & Pluckthun, A. (2006). Pegylation and multimerization of the anti-p185HER-2 single chain Fv fragment D5: effects on tumor targeting. *J Bio Chem* 281, 35186-35201.
8. Kipriyanov S. M., Moldenhauer G., Schuhmacher J., Cochlovius, B., Von der Leith C. W (1999). Bispecific tandem diabody for tumor therapy with improved antigen binding and pharmacokinetics. *J Mol Biol* 293, 41-56.
9. Zhang, J., Tanha, J., Hirama, T., Khieu, N. H., To, R., Tong-Sevinc, Hong., Stone, E., Brisson, J., & Mackenzie, C. R. (2004). Pentamerization of single domain antibodies from phage libraries; a novel strategy for the rapid generation of high avidity antibody reagents. *J Mol Biol* 335, 49-56.
10. Stone E., Hirama, T., Tanha, J., Tong-Sevinc, H., Li, S & Mackenzie, C. R. (2006). The assembly of single domain antibodies into bispecific decavalent molecule. *J Immunol Methods* 318, 88-94.
11. Terskikh, A. V., Le Doussal, J. M., Crameri, R., Fisch, I., & Mach, J. P. (1997). Pentabody: a new type of high avidity binding protein. *Proc Natl Acad Sci USA* 94, 1663-1668.
12. Fattah, O. M., Cloutier, S. M., Kundig, C., Felber, L. M. & Gygi, C. M. (2006). Pentabody-EGF: a novel apoptosis inducer targeting Erb1 receptor overexpressing cancer cells. *Int J Cancer* 119, 2455-2463.
13. Toro, I., Basquin, J., Teo-Dreher, H. & Suck, D. (2002). Archael sm proteins form heptameric and hexameric complexes: crystal structures of the sm1 and sm2 proteins from the hyperthermophile *archaeoglobus fulgidus*. *J Mol Biol*. 320, 129-142.
14. Toro, I., Thore, S., Mayer, C., Basquin, J., Seraphin, B., & Suck, D. (2001). RNA binding an Sm core domain: X-ray structure and functional analysis of an archaeal Sm protein complex. *EMBO J* 20, 2293-2303.
15. Beck, K., Gambee, J. E., Bohan, C. A & Bachinger, H. P (1996). The C-terminal domain of cartilage matrix protein assembles into a triple-stranded alpha-helical coiled-coil structure. *J Mol Biol* 256, 909-923
16. Orlova, A., Magnusson, M., Eriksson, T. L., Nilsson, M., Larsson, B., Hoiden-Guthenberg, I., Widstrom, C., Carlsson, J., Tolmachev, V., Stahl, S., & Nilsson, F. Y. (2006). Tumor imaging using a picomolar affinity HER2 binding affibody molecule. *Cancer Res* 66, 4339-4348.
17. Friedman, M., Orlova, A., Johansson, E., Eriksson, T. L., Holden-Guthenberg, I., Tolmachev, V., Nilsson, F. Y. & Stahl, S. (2008). Directed evolution to low nanomolar affinity of a tumor-targeting epidermal growth factor receptor binding affibody molecule. *J Mol Biol* 376, 1388-1402.
18. Aggarwal, S., Singh, P., Topaloglu, O., Isaacs, J. T., & Denmeade, S. R. (2006). A dimeric peptide that binds selectively to prostate-specific membrane antigen and inhibits its enzymatic activity. *Cancer Res* 66, 9171-9177.
19. Duan, J., Wu, J., Valencia, C. A., & Liu, R. (2007). Fibronectin type III domain based monobody with high avidity. *Biochemistry* 46, 12656-12664.
20. Leonard, D., Hayakawa, A., Lawe, D., Lambright, D., Bellve, K. D., Standley, C., Lifshitz, L. M., Forgarty, K. E., & Corvere, S. (2008). Sorting of EGF and transferring at the plasma membrane and by cargo-specific signaling to EEA1-enriched endosomes. *J Cell Sci* 121, 3445-3458.
21. Nordberg, E., Ekerljung, L., Sahlberg, S. H., Carlsson, J., Lennartsson, J., & Glimelius, B. (2010). Effects of an EGFR-binding affibody molecule on intracellular signaling pathways. *Int J Oncol* 36, 967-972.
22. Gostring, L., Chew, M. T., Orlova, A., Hoiden-Guthenberg, I., Wennborg, A., Carlsson, J., & Frejd, F. Y. (2010). Quantification of internalization of EGFR-binding affibody molecules: Methodological aspects. *Int J Oncol* 36, 757-763.

Example 2

Heptameric Targeting Ligands with High Stability and Avidity

Target binding affinity molecules are of great importance in various biomedical applications. One of the major challenges in developing targeting ligands is to improve their target-binding strength while maintaining their high specificity. Although such properties can be improved through extensive affinity maturation, the process is slow, tedious, and often limited [1]. Currently, there is an urgent need for the facile development of affinity molecules that can bind to the targets of interest with high affinity and specificity. One of the most critical design parameters for satisfactory in vivo targeting is to increase targeting ligand valency, defined as the number of antigen-binding sites [1]. Multivalent targeting for the attainment of high binding affinity has known natural examples, such as the binding between an antibody and its target antigen: an intrinsic characteristic of mammalian antibodies [1]. Multivalent targeting ligands maintain several major advantages over monovalent ligands when targeting cell surface receptors. First, the target-binding strength of the multivalent ligand could be significantly improved [2]. Second, the multimerization process increases the molecular weight of the affinity molecule above that of the glomerular filtration cut-off, thereby reducing in vivo excretion while increasing tumor accumulation characteristics via enhanced permeability and retention (EPR). For example, it has been demonstrated that monovalent binding is often not sufficient for efficacious cancer targeting, and most monovalent targeting ligands, despite nanomolar or picomolar binding affinities, tend to have fast dissociation rates, providing modest retention times on the target antigen in in vivo non-equilibrium environments [1-3].

Due to these advantages, several techniques in multivalency engineering of antibodies have been developed, including domain-swapping, linear fusion, chemical linking, self-assembly, and heterodimerization [1]. Most of these approaches are limited to targeting ligands based on natural antibodies or their fragments. However, a self-assembly approach based on the use of various domains that permit self-multimerization may be a general strategy for the systematic development of novel targeting ligands.

Successful and efficient conversion of a monovalent ligand into a multivalent form is challenging and requires a combination of unique features on both the target binding and the multimerization moieties. Due to the tendency of aggregation, steric hindrance, and fast dissociation, very few self-multimerization domains are suitable for efficient self-assembly [1]. First, the scaffold should be small and soluble enough for high expression in bacteria or mammalian cells. Second, the self-assembly of a monomeric domain into its multimeric form with desired valency should be very efficient with extraordinarily high association constants and low aggregation tendency. The resulting complex should have a well-defined parallel multimeric structure with high stability that allows for the introduction of target-binding moiety and hinge region to achieve desired multivalency without disrupting target binding. This is particularly challenging when the complex is significantly diluted in the bloodstream under in vivo conditions. To circumvent these problems, new multimerization domains require investigation for the development of higher avidity targeting ligands.

Targeting ligands with di-, tri-, tetra-, and pentavalency have been developed, however, those with a valency higher than five have not been reported and it is the focus of this study [4-14]. One protein class featuring heptameric structures is the Sm or Sm-like (Lsm) RNA-binding protein that has been implicated in a variety of RNA processing events in all eukaryotic organisms [15]. Structural analyses indicate that the core domain of Sm protein self-assembles into a heptameric complex with a doughnut-shaped ring structure that accommodates uracil rich RNAs, as shown in human canonical Sm core domain, human Lsm, and other Sm proteins [15]. To generate novel heptameric targeting ligands with high stability and binding affinity, the 70-amino acid multimerization domain from the hyperthermophilic Archaeal Sm protein was used. Recently, the crystal structures of the Sm1 and Sm2 proteins from hyperthermophilic *Archaeoglobus fulgidus* (AF) have been solved [16]. While the AF-Sm2 hexamer is RNA-dependent and only stable at low pH, the AF-Sm1 heptamer is highly stable regardless of pH and the absence of RNA. Significantly, AF-Sm1 forms a seven-membered ring, presumably due to the continuous inter-subunit hydrogen bonding between β-strands 4 and 5. The thickness of the core ring is 32 Å, while the outer and inner diameters are 65 Å and 13 Å, respectively [16].

In the present study, heptameric targeting ligands directed towards cell surface receptors such as EGFR, HER2, and PSMA have been developed by utilizing the heptamerization domain of the AF-Sm1 domain and an EGFR-, HER2-, or PSMA-binding protein domain or peptide as the target binding moiety connected through a flexible hinge peptide. The heptameric targeting ligands were self-assembled during expression in a host cell with high efficiency, retained their binding specificity, showed significantly enhanced target-binding strength, and demonstrated unusually high stability with non-toxic property, implying that this general heptamerization strategy has the potential to be widely applied for the systematic improvement of the target-binding strength of many affinity molecules, particularly those based on small protein domains or short homing peptides.

Cell Culture

EGFR-positive A431, EGFR-negative Jurkat, HER2-positive SK-OV3, HER2-low expressing MCF7, PSMA-positive LNCaP, and PSMA-negative PC3 cells were obtained from the UNC Tissue Culture Facility. All cell lines were maintained by serial passage at 37° C. in 5% $CO_2$ in an appropriate medium supplemented with 10% fetal bovine serum, 100 units/mL of penicillin, and 0.1 mg/mL streptomycin.

Plasmid Construction

The codon-optimized DNA sequences that code for the heptamerization domain of the Archaeal SM1 gene and the EGFR-, HER2-, or PSMA-binding domain or peptide were codon-optimized and custom-synthesized by GenScript (Piscataway, N.J.). The design of each monomeric and heptameric targeting ligand is shown in FIG. 11. The amino acid sequence for each component of the heptameric targeting ligands is listed in Table 2. After PCR amplification, the gene products containing the target binding domain, hinge linker, and heptamerization domain, were digested with Nco I and Xho I. The digested fragments were cloned into the corresponding sites (Nco I and Xho I) of pET28b (Novagen, Darmstadt, Germany). The cloned plasmids were confirmed by sequencing prior to use in protein expression.

Protein Expression and Purification

Each expression vector was transformed into *E. coli* BL21 (DE3) Rosseta cells (Novagen, Darmstadt, Germany). The positive clones were selected on LB plates containing kanamycin (50 μg/mL) and chloramphenicol (34 μg/mL). A single colony was selected and grown in 5 mL of LB medium overnight at 37° C. The resulting culture was added to a flask with 500 mL of LB medium containing kanamycin (50 μg/mL) and chloramphenicol (34 μg/mL). The cells were grown at 37° C. until the optical density (at 600 nm) reached 0.5 to 1.0. IPTG with a final concentration of 1 mM was then added to the cell cultures, followed by incubation at 22° C. for 16 h. After induction, the cells were spun down at 3,000 g for 10 min at 4° C., and the pellet was stored at −20° C. until use. To purify the monomeric and heptameric ligands that assembled in the cell during expression of the cDNA, the cell pellet was resuspended in buffer A (25 mM HEPES pH 7.4 and 300 mM NaCl) and sonicated for 1 min for a total of 5 times. The soluble fraction was recovered by centrifugation at 12,000 g for 10 min at 4° C. The resulting fraction was loaded onto a TALON metal affinity column (Clontech, Mountainview, Calif.) pre-equilibrated with buffer A. Approximately 20 column volumes of buffer A were used for initial washing followed by extensive washing (20 column volumes) with buffer B (buffer A with 20 mM imidazole). The protein of interest was eluted with buffer C (buffer A with 200 mM imidazole). The quality of the purified proteins was examined by SDS-PAGE.

Native Gel Electrophoresis

An 8% discontinuous native gel was prepared without SDS and reducing agents based on the standard Laemmli SDS-PAGE protocol. About 5 μg of highly purified monomer or 20 μg heptamer was loaded to the appropriate lane, and separated on an 8% native gel. Proteins were stained with coomassie brilliant blue R-250.

Analytical Ultracentrifugation

Highly purified monomeric or heptameric ligands were prepared in a buffer containing 25 mM HEPES pH 7.4 and 150 mM NaCl. The solution was centrifuged at 10,000 g for 20 h at 20° C. The absorbance at 280 nm was recorded every 2 h during centrifugation. Each resulting absorbance was fit into a self-association model to calculate the molecular weight.

FITC Labeling of Monomeric and Heptameric Targeting Ligands

Each monomeric and heptameric molecule was labeled with fluorescein isothiocyanate (FITC) (ACROS organics, Geels, Belgium) in 50 mM borate buffer (pH 8.5). Briefly, 1 mg of each protein was reacted with a 25 molar excess of FITC in the reaction buffer and incubated at room temperature for 2 h. The resulting mixture was quenched by the addition of 100 mM Tris-HCl (pH 8.8) at room temperature for 1 h. Un-reacted free FITC molecules were removed by passing the reaction mixture through a NAP-10 column (GE Healthcare, Piscataway, N.J.). Extensive dialysis was performed overnight using a 3 kDa molecular weight cut off dialysis membrane (GE Healthcare, Piscataway, N.J.) to further remove the residual FITC.

Cell Surface Binding Analysis

Approximately $2 \times 10^4$ cells were seeded on coverslips and allowed to grow in the appropriate media for 16 h. The resulting coverslips were washed twice with 1×PBS buffer followed by incubation in different concentrations of FITC labeled monomeric or heptameric targeting ligand for 30 min at room temperature. The coverslips were washed three times with 1×PBS. The resulting samples were visualized by using a Zeiss LSM 510 confocal microscope.

BIAcore Analysis

The BIAcore 2000 (BIAcore AB, Uppsala, Sweden) was used for surface plasmon resonance analysis. 1 μg of purified extracellular domain of recombinant human EGFR ECD-Fc, HER2 ECD-Fc, or PSMA (R&D System, Minneapolis, Minn.), was diluted in a buffer containing 10 mM sodium acetate pH 5.0 and immobilized on a CM5 sensor chip (GE healthcare, Piscataway, N.J.) by amine coupling according to the manufacturer's instruction (about 2,500 resonance units). Various concentrations of monomeric or heptameric ligands were injected onto the flow cell in an HBS-P buffer (10 mM HEPES pH 7.4, 150 mM NaCl, and 0.005% surfactant P20) at a flow rate of 20 μl/min. The dissociation equilibrium constant ($K_D$), the association rate ($K_a$) and the dissociation rate ($K_d$) were calculated using the BIAevaluation software (BIAcore) by fitting the data on a one to one Langmuir binding model.

Circular Dichroism Spectroscopy

Highly purified monomeric or heptameric proteins were prepared in 10 mM phosphate buffer (pH 7.5) and used for circular dichroism (CD) scanning with an AVIV model 202-01 spectropolarimeter. Spectra were recorded from 190 nm to 260 nm at 0.2 nm intervals, a scan speed of 20 nm/min, a bandwidth of 2 nm, and an integration time of 1 s. To determine thermal stability, spectra were recorded by gradually increasing the temperature from 25° C. to 94° C. at 220 nm.

Resistance to Protease-Mediated Degradation

The protease digestion was performed in HBS buffer (10 mM HEPES pH 7.4 and 150 mM NaCl) at 25° C., 37° C., 42° C., and 60° C., respectively, for 20 min. About 5 μg of each protein was incubated with 100 ng of thermolysin. After incubation, the resulting reaction mixtures were separated by SDS-PAGE to monitor the extent of protein degradation.

Co-Localization Studies

A431 and SK-OV3 cells were seeded onto the coverslips and grown for 16 h at 37° C. FITC-labeled 10 nM or 100 nM of heptameric $Z^{EGFR}$ and $Z^{HER2}$ were incubated for 2 h at 37° C. with A431 and SK-OV3 cells grown on coverslips, respectively. After washing away unbound targeting ligands, the cells were fixed with 2% paraformaldehyde in PBS for 15 min at room temperature. Cells were then washed three times with 1×PBS. For immunostaining, blocking solution (PBS with 5% BSA and 0.3% Triton X-100) was added and incubated for 1 h at 4° C. The cells were then incubated with the anti-EEA1 rabbit monoclonal antibody (1:200) (Cell Signaling Technology, Danvers, Mass.) overnight at 4° C. After incubation with secondary antibody (Alexa Fluor 555 conjugated anti-Rabbit IgG (Cell Signaling Technology, Danvers, Mass.) for 1 h at 4° C., the corresponding cells were rinsed three times with 1×PBS followed by the addition of an anti-fade reagent. Cells were examined by using a Zeiss LSM 510 confocal microscope.

Cell Proliferation MTS Assay

A CellTiter96 Aqueous Non-Radioactive Cell Proliferation Assay kit from Promega (Madision, Wis.) was used for the MTS assay. Approximately $1 \times 10^4$ cells were seeded in each well of a 96-well plate and grown for 16 h at 37° C. Each heptameric molecule was incubated with the cells for 24 h. 10 µM Cis-platinum (II) diamine dichloride (Sigma-Aldrich Chemical Co, St Louis, Mo.) was used as a positive control. Approximately 20 µl of MTS/PMS solution was added into each well followed by incubation for 4 h at 37° C. The absorbance at 490 nm was recorded using an ELISA plate reader.

General Design of Heptameric Targeting Ligands

In previous self-association approaches for the generation of trimeric and pentameric complexes, additional cysteine (Cys) residues were introduced to stabilize the oligomeric structure through the formation of inter-molecular disulfide bonds [10,11,14,17]. However, the formation of undesired disulfide bonds is common, resulting in mis-folding, aggregation, and loss of target-binding functions [1]. To circumvent these problems, the 70-amino acid AF-Sm1 heptamerization domain from hyperthermophilic *Archaeoglobus fulgidus* was used, which is highly stable and can efficiently self-assemble into a parallel heptameric complex without relying on any disulfide bond (FIG. 11B).

Figure 11A:
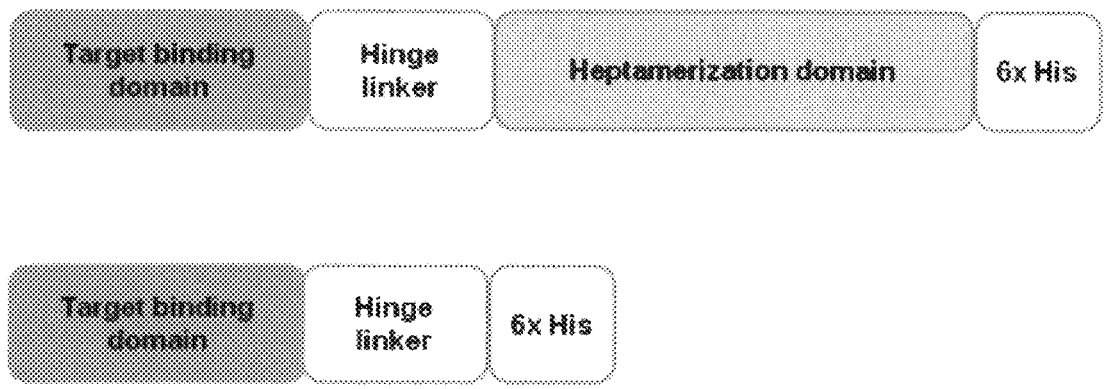
FIG. 11. Schematic diagram of monomeric and heptameric targeting ligands. (A) The cDNA of heptameric ligand consists of coding regions for a target binding domain, a flexible hinge linker, and a heptamerization domain. A 6×His-tag was introduced on the C-terminus of each molecule. The structure of the monomeric targeting ligand is similar to the heptameric ligand with the exception of the absence of the heptamerization domain. (B) Schematic representation of the monomeric and heptameric ligands; Z domain structure was obtained from the Protein Data Bank (PDB) database (PDB ID:2B89) (www.pdb.org).
Figure 11B:
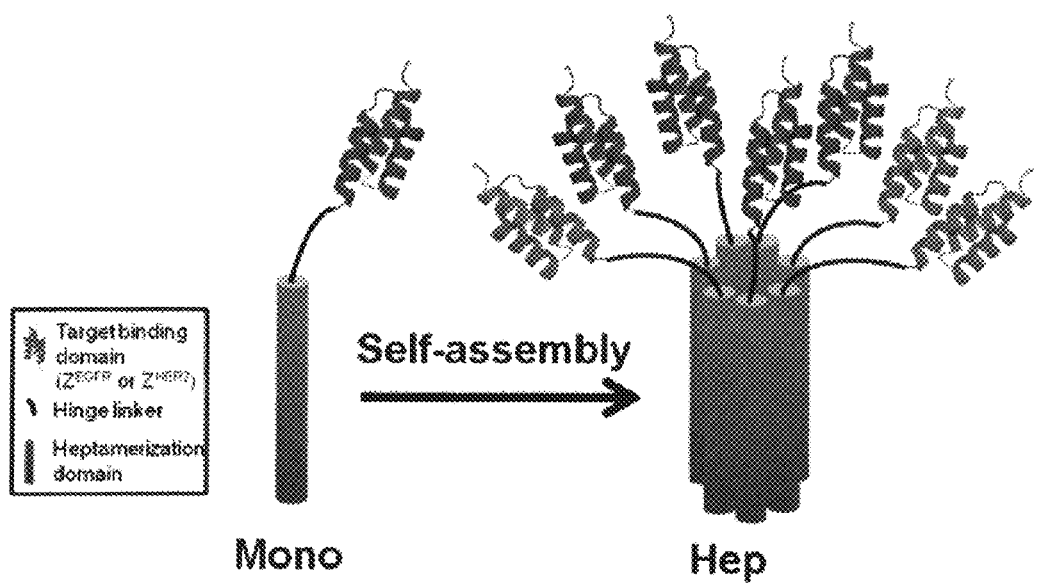

The general strategy used to develop the heptameric targeting ligands is to link a small target-binding protein domain through a hinge linker with the AF-Sm1 heptamerization domain (FIG. 11A). In principle, any target-binding protein domains or short peptides isolated from a highly diversified protein domain or peptide library using various in vitro selections or directed molecular evolutions, including phage display, yeast display, bacterial display, ribosome display, and mRNA display, can be used as the target-binding moiety. To investigate whether functional heptameric targeting ligands can be readily generated using this strategy, an EGFR- or HER2-binding Z domain ($Z^{EGFR}$ or $Z^{HER2}$), or a PSMA-binding short peptide, that does not contain any Cys residue, as reported in the literature, were tested as examples to facilitate the self-assembly process [18,19, 30]. The Z domain is composed of 58-amino acids derived from the immunoglobulin binding Z-domain of *staphylococcal* protein A [18], a small (~7 kDa) protein domain with a three-helix bundle structure (FIG. 11B). It has been reported that the Z domain-based targeting ligands could be selected with high affinity to a given target from a library with high diversity [18,19]. To compare the monomeric and the corresponding heptameric forms, the monomeric targeting ligands were constructed by deleting the heptamerization domain (FIG. 11A). In addition, a His-tag was introduced at the C-terminus of both monomeric and heptameric ligands to facilitate protein purification.

Figure 12:
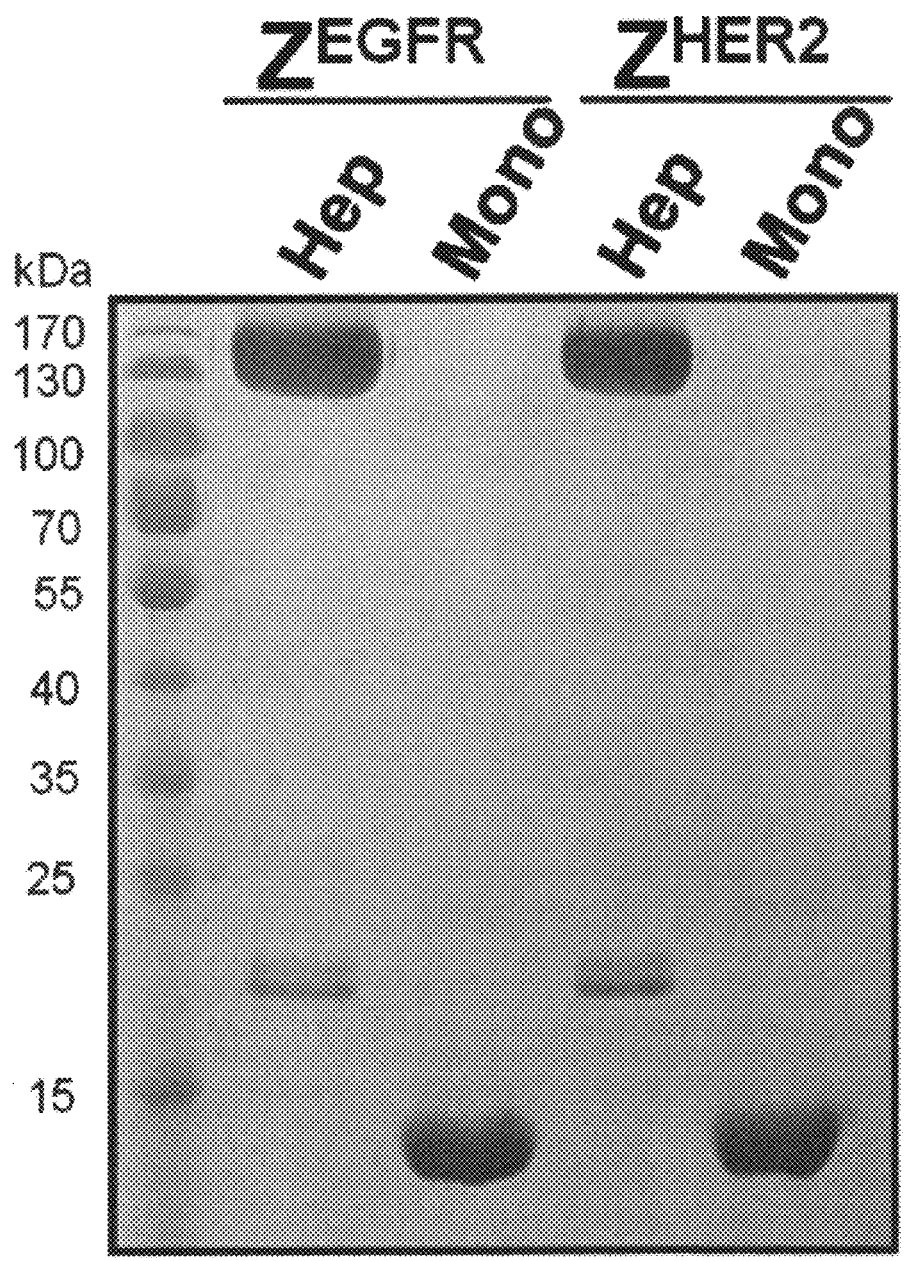
FIG. 12. SDS-PAGE analysis of the purified monomeric and heptameric targeting ligands. The purified heptameric $Z^{EGFR}$, monomeric $Z^{EGFR}$, heptameric $Z^{HER2}$, and monomeric $Z^{HER2}$ ligands were separated on a 10% SDS-PAGE gel. About 5 µg of each protein was applied to each lane.
Figure 13:
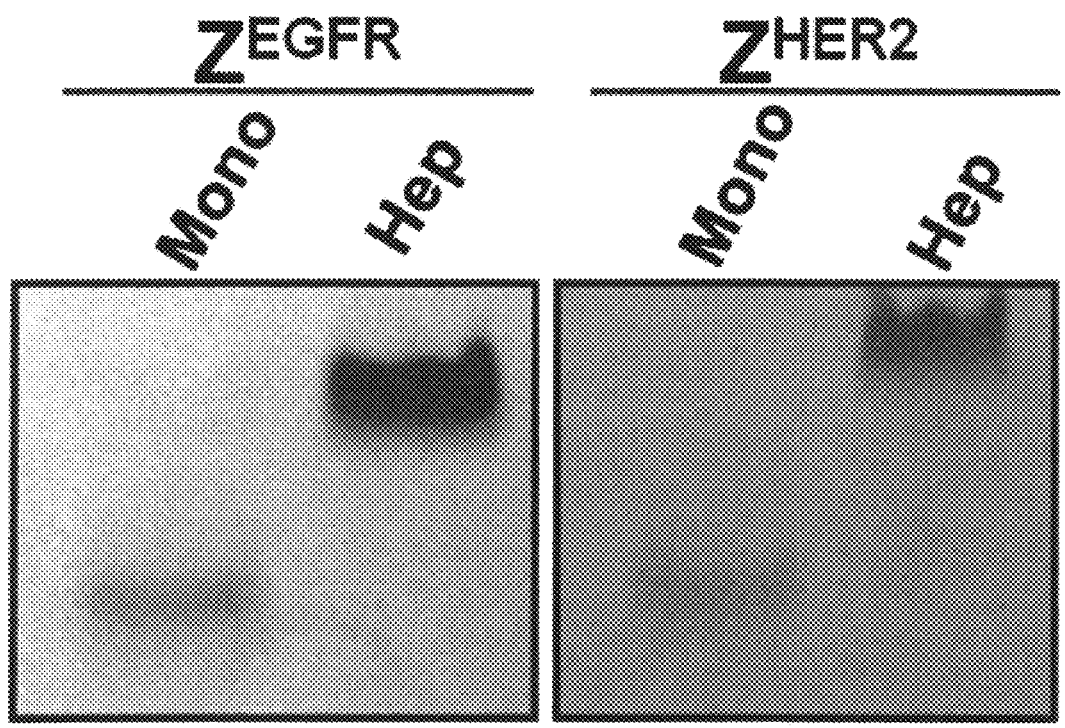
FIG. 13. Native gel separation of monomeric and heptameric targeting ligands. The purified monomeric $Z^{EGFR}$, heptameric $Z^{EGFR}$, monomeric $Z^{HER2}$ and heptameric $Z^{HER2}$ ligands were separated on an 8% native gel. About 5 µg of the purified monomer or 20 µg heptamer was loaded to the appropriate lane.

Expression, Purification and Characterization of Monomeric and Heptameric Targeting Ligands The cDNAs that encode the monomeric and heptameric targeting ligands were cloned into a pET28b expression vector that contains a C-terminal 6×His-tag to facilitate protein purification by $Co^{2+}$-nitrilotriacetic acid (NTA) column. The expression level of the targeting ligands was high with a yield of approximately 20 mg/L and 10 mg/L for the monomeric and heptameric ligands as soluble proteins, respectively. $Co^{2+}$-NTA purified monomeric and heptameric ligands were analyzed by SDS-PAGE (FIG. 12). The predicted molecular weight of the monomeric targeting ligands without the heptamerization domain is about 5.0 kDa for $SP^{PSMA}$, 10.2 kDa for $Z^{EGFR}$ and 10.5 kDa for $Z^{HER2}$, respectively. In the case of heptameric Z ligands, the monomeric form with the AF-Sm1 domain has a molecular weight of 18 kDa, whereas its corresponding heptameric form has a predicted molecular weight of 126 kDa. As shown in FIG. 12, both monomeric $Z^{EGFR}$ and $Z^{HER2}$ could be purified to near homogeneity. When a heptamerization domain was introduced in the construct, the vast majority of the expressed protein was present in a multimeric form with molecular weight of approximately 130 kDa, even though a small portion of the monomeric form (18 kDa) was also detected (FIG. 12). Because the molecular weight of the multimeric form (130 kDa) is very close to that of the putative heptameric form (126 kDa), it strongly suggests that this multimeric form is the putative heptamer. Similar results were obtained when heptameric $SP^{PSMA}$ was used. It appears that the formation of the heptameric form was efficient without applying any special folding procedures, as shown by SDS-PAGE (FIG. 12). The heptameric form is highly stable since it can resist the strong denaturing conditions of SDS present in the loading buffer as well as in the polyacrylamide gel. This result clearly indicates that the self-assembly to a heptameric form is robust and highly efficient. The presence of a small amount of the monomeric form on SDS-PAGE raises question whether the monomeric form co-exists with the heptameric form before SDS-PAGE analysis or it is generated by disassembling the heptameric form back to the monomeric form when denaturing conditions were applied during SDS-PAGE. To address this question, the purified heptameric ligands were further examined by using native gel electrophoresis. As shown in FIG. 13, both purified heptameric $Z^{EGFR}$ and $Z^{HER2}$ targeting ligands were present as a single band under non-denaturing conditions with much lower mobility compared with monomeric ligands, whereas the corresponding 18 kDa monomeric form was not detected. Taken together, the self-assembled multimeric targeting ligands exist predominately as a heptameric form under native conditions.

Although the molecular weight of the heptameric form on SDS-PAGE is around 130 kDa for heptameric Z ligands, it is of interest to measure the exact molecular weight of the putative heptamer. To further confirm the heptameric state, analytical ultracentrifugation was used to determine the molecular weights of both heptameric ligands. As shown in FIGS. 5A-B, the two putative heptameric targeting ligands have a molecular weight of 131±3 kDa for heptameric $Z^{EGFR}$ and 130±2 kDa for heptameric $Z^{HER2}$, respectively. These values are consistent with those shown from SDS-PAGE gels and also match the theoretical molecular weights (~126 kDa) of the heptameric form. Altogether, it was demonstrated that the multimerization domain containing targeting ligand can self-assemble into a heptameric form very efficiently under native conditions while the presence of the monomeric form is minimal.

Figure 14B:
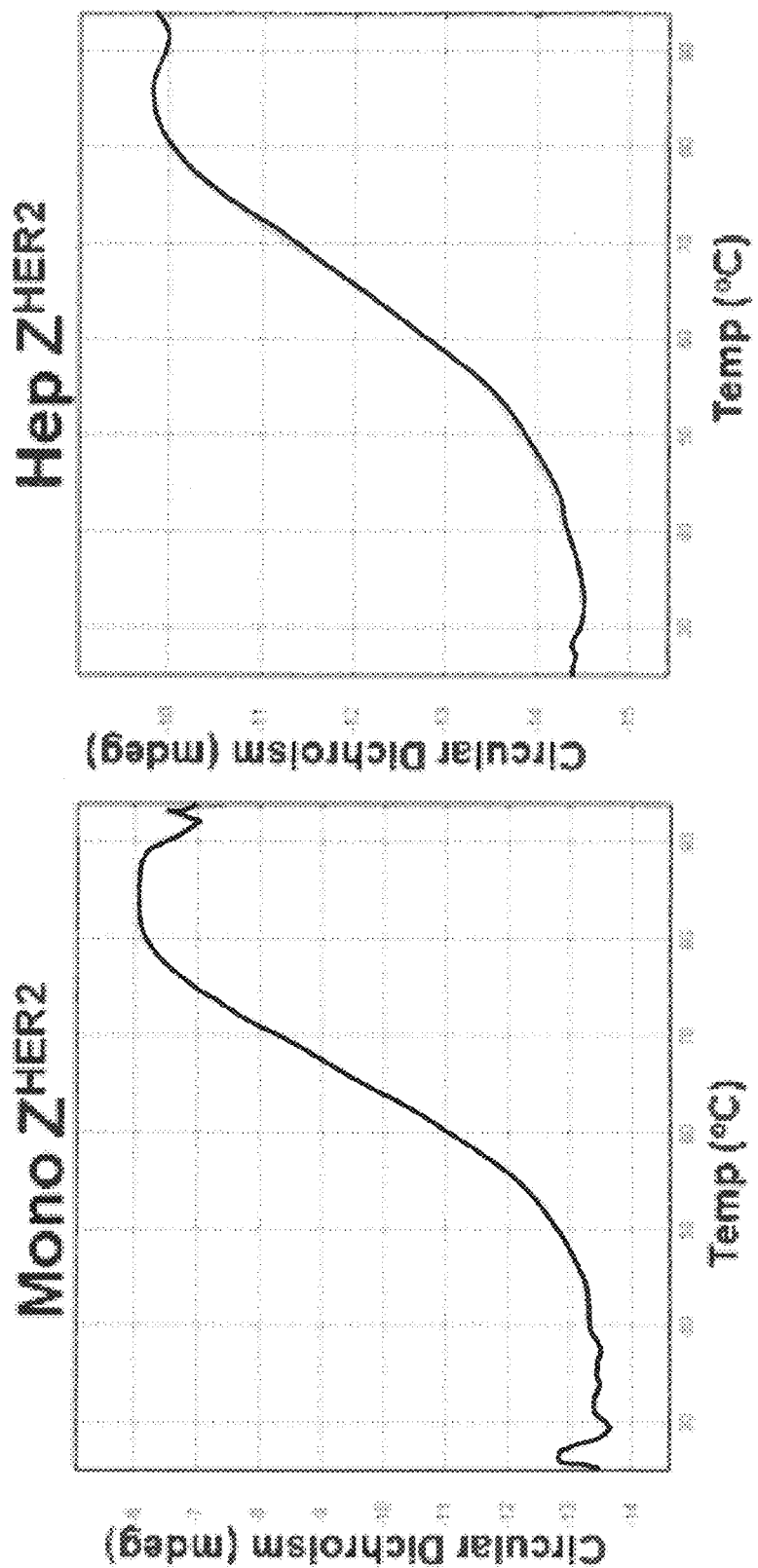
Figure 14C:
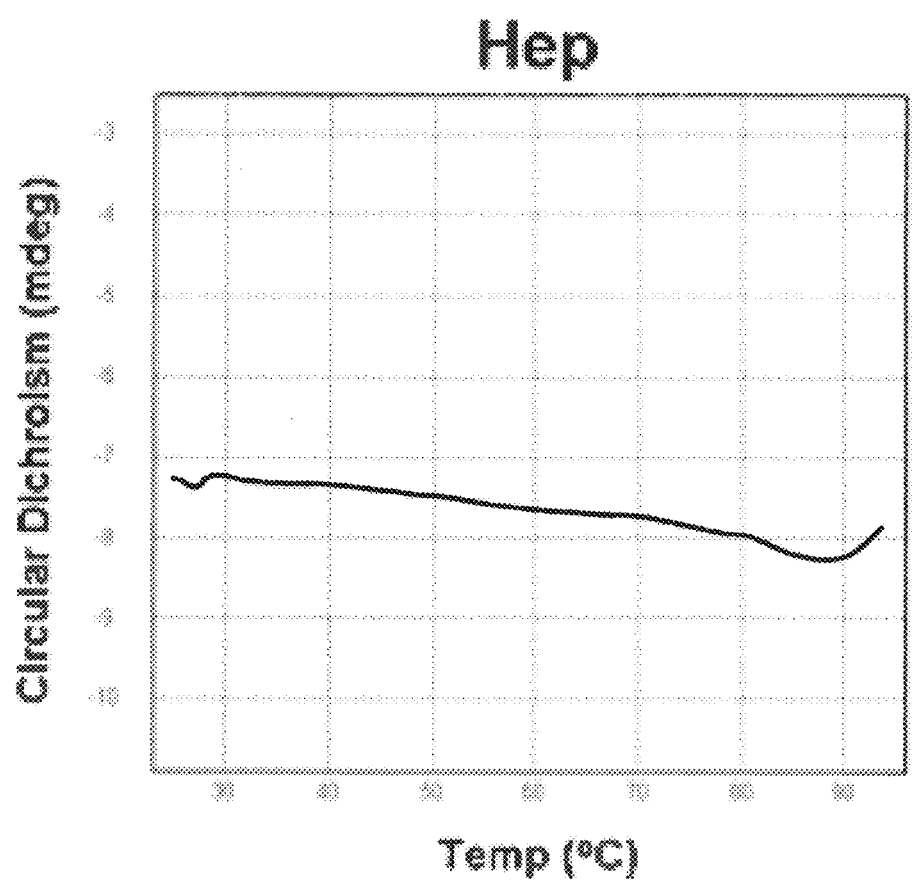
Figure 15A:
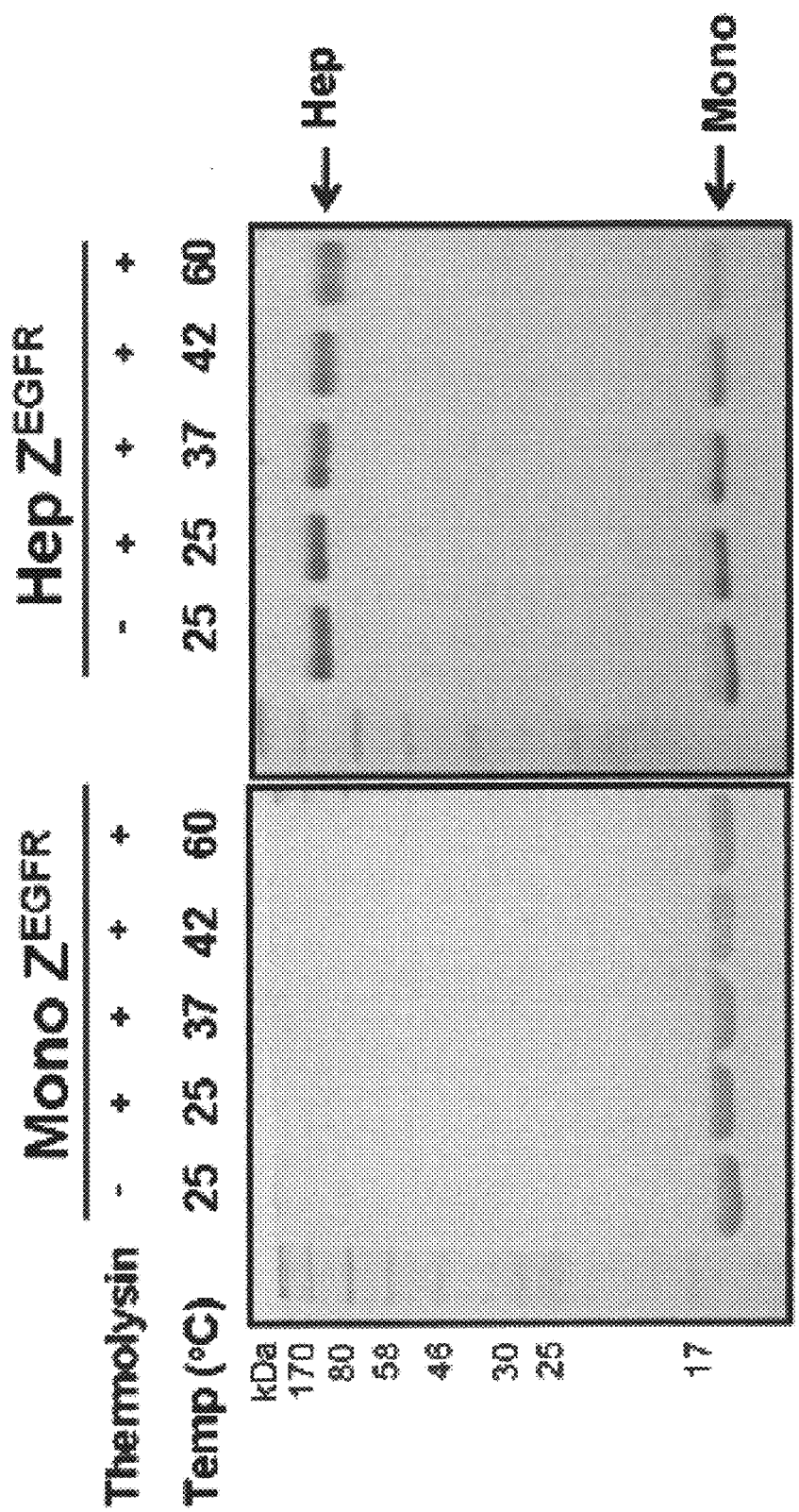
FIGS. 15A-B. Analysis of the protease resistance of the monomer and the heptamer by thermolysin. About 5 µg of (A) monomeric and heptameric $Z^{EGFR}$ and (B) monomeric and heptameric $Z^{HER2}$ targeting ligands were incubated with 100 ng of thermolysin at different temperatures for 20 min. After incubation, reaction was stopped by adding SDS sample buffer and each reaction mixture was separated on a 10% SDS-PAGE to examine protein degradation.
Figure 15D:
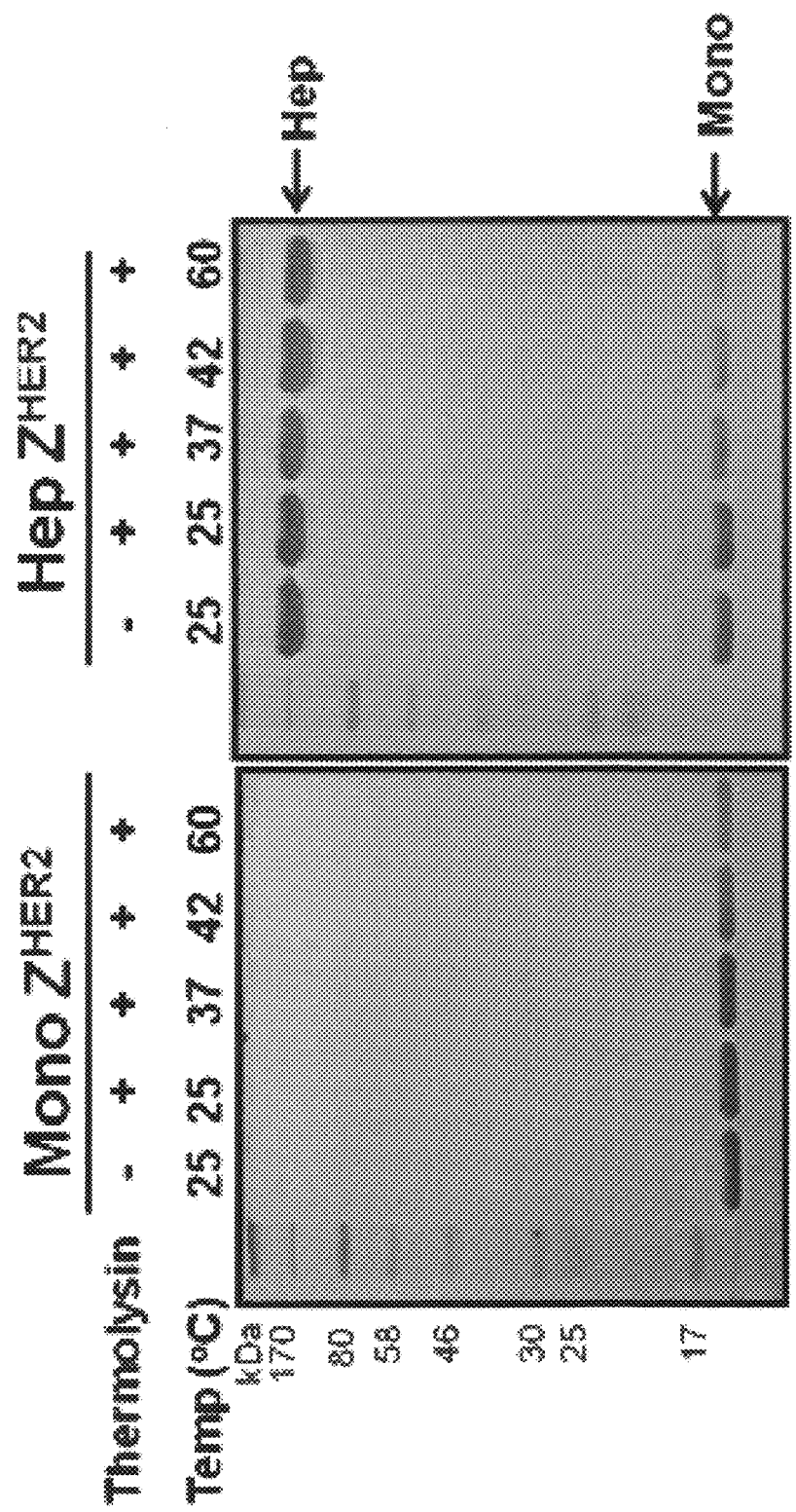

An ideal affinity molecule should have exceptional stability to be readily used in various in vitro and in vivo applications. To determine the thermal stability of these targeting ligands, circular dichroism (CD) analysis was performed using highly purified monomeric and heptameric proteins. Thermal denaturation was monitored at 220 nm. As shown in FIGS. 14A-B, the $T_m$ value of each protein is approximately 65° C. for all ligands, whereas the heptameric complex itself is highly resistant to heat-induced denaturation (FIG. 14C). These results indicate that heptameric Z ligands are as stable as monomeric Z ligands. Degradation of protein-based affinity molecules by various physiological proteases is another barrier that must be overcome for their in vivo applications. To examine the resistance of these targeting ligands to proteases, a protease-mediated digestion assay was performed by subjecting the monomeric or heptameric Z targeting ligands to a thermostable metallopeptidase thermolysin [20]. All of the heptameric forms were resistant to thermolysin digestion even when the temperature was as high as 60° C., whereas monomeric forms are more susceptible to protease at 60° C. (FIGS. 15A-B). This result demonstrates that such heptameric targeting ligands are stable under harsh conditions, implying that they have a higher potential of being resistant to degradation in vivo and used as targeting ligands for in vivo applications.

The Determination of Target Binding Strength

Figure 7:
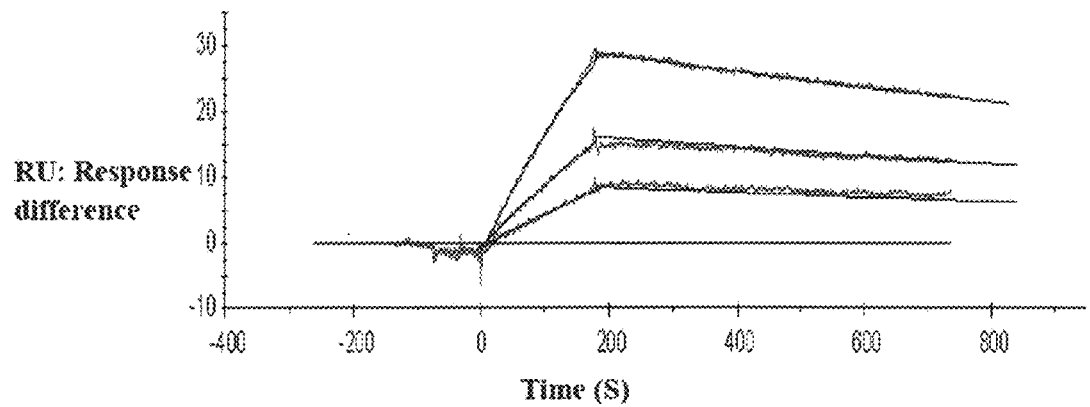
FIGS. 7A-D. Biacore analysis of target binding properties of a) $Z^{EGFR}$ monomeric and heptameric molecules and b) $Z^{HER2}$ monomeric and heptameric molecules. Each receptor was immobilized on a CM5 chip. Different concentrations of proteins were injected on each experiment. Each analysis was performed at room temperature and flow rate of 20 µl/min.
Figure 7:
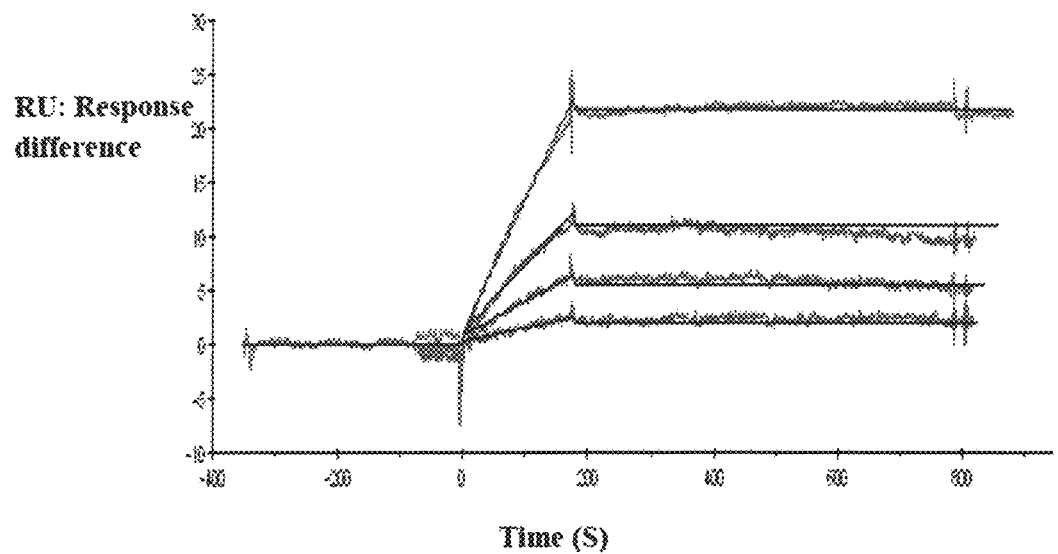
Figure 7:
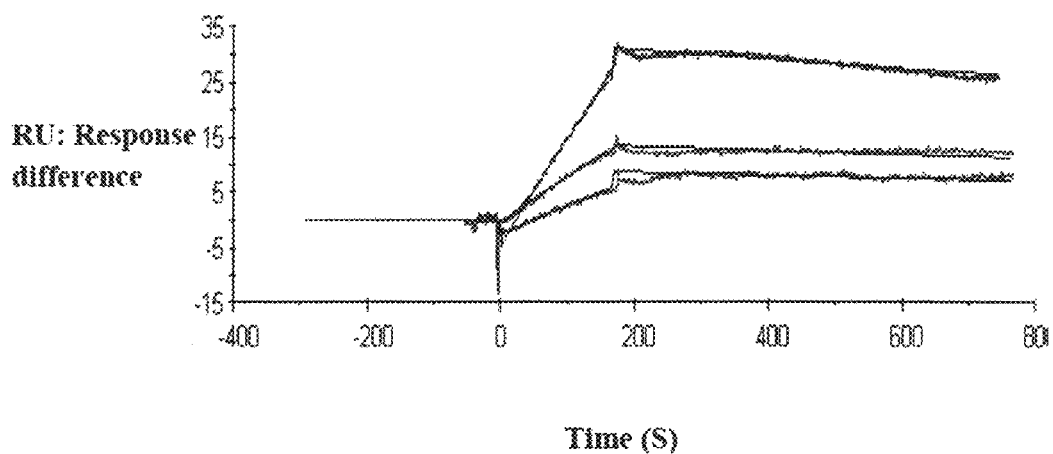
Figure 7:
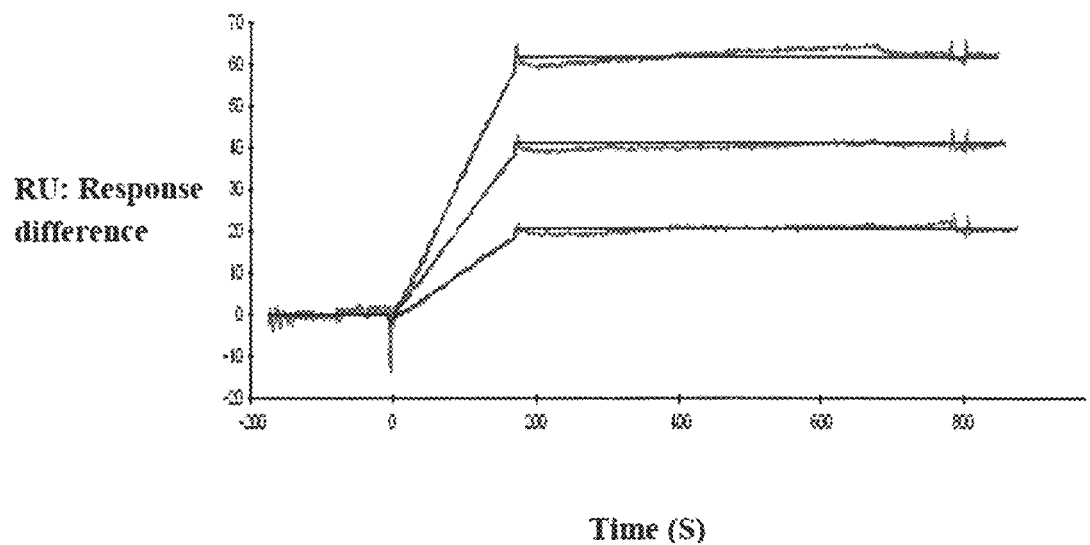

To investigate whether purified heptameric complex maintained the target binding features towards the target of interest, surface plasmon resonance (SPR) was employed to examine the binding strength and specificity of the monomeric and heptameric ligands. Here, the extracellular domains of EGFR or HER2 were immobilized on the surface of CM5 biosensor chip followed by injection of purified monomeric or heptameric ligands. No binding was detected for any of the targeting ligands when an irrelevant protein target was used as a negative control. As expected, it was evident that $Z^{EGFR}$ targeting ligands did not bind to HER2 receptor, and neither $Z^{HER2}$ targeting ligands showed any detectable binding against EGFR. The binding constant $K_D$ of the monomeric $Z^{EGFR}$ ligand (2.6±0.3 nM) by fitting data on one to one Langmuir binding model was similar to that of $Z^{EGFR}$ affibody (5 nM) reported by Stahl and co-workers (Table 1 and FIG. 7A) [19]. The heptameric $Z^{EGFR}$ ligand has greatly enhanced EGFR-binding strength at $K_D$ of 29±20 pM, which is approximately 100 fold higher than that of the monomeric form (Table 1). In the case of the heptameric $Z^{HER2}$ ligand, about 1000 fold increased HER2-binding strength ($K_D$ of 2±0.5 pM) was achieved compared to that of the monomeric $Z^{HER2}$ ligand ($K_D$ of 1.7±0.7 nM) (Table 1 and FIG. 7B). These results clearly indicate that the target binding strengths of heptameric ligands have significantly increased as a result of the multivalency effect.

Heptameric Targeting Ligands are Internalized and Present in the Endosome

Figure 16A:
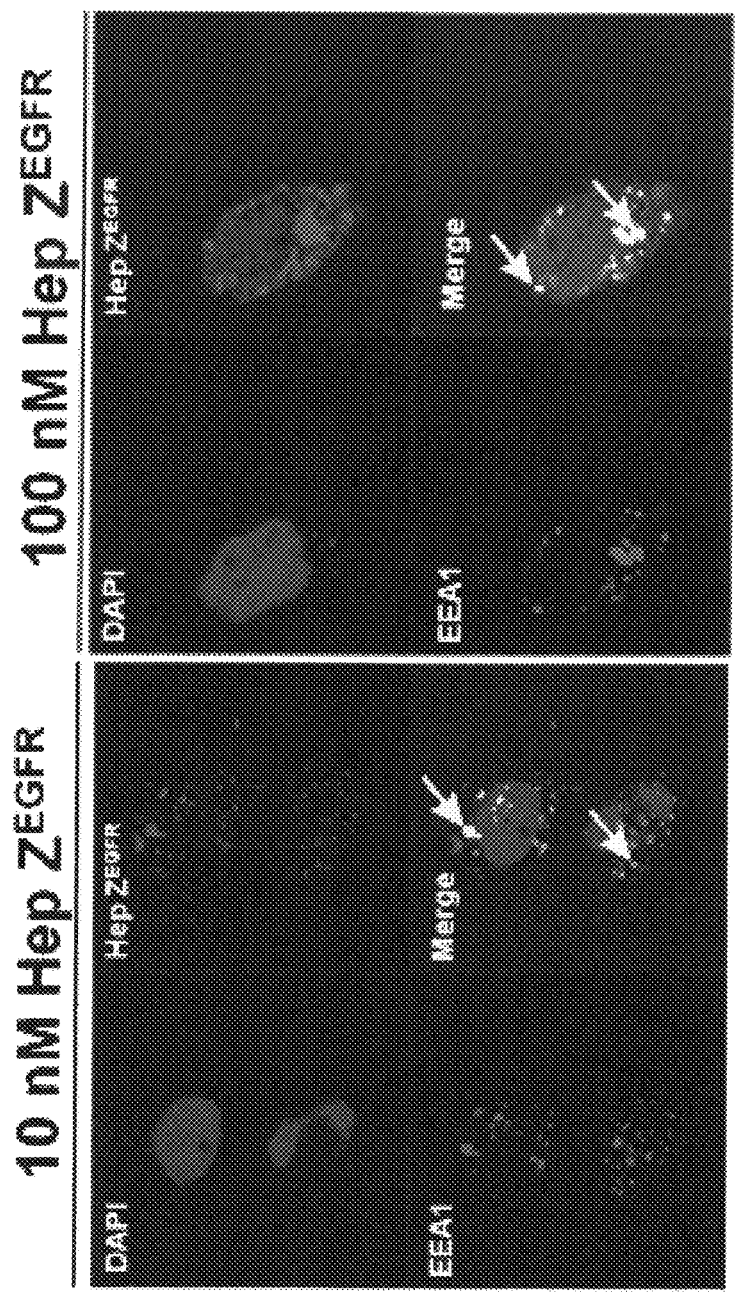
FIGS. 16A-B. Co-localization of EEA1 and heptameric targeting ligands. (A) Two different concentrations of the FITC-labeled heptameric $Z^{EGFR}$ targeting ligands were incubated with A431 cells for 2 h at 37° C. (B) FITC-labeled heptameric $Z^{HER2}$ targeting ligands at two concentrations were incubated with SK-OV3 cells for 2 h at 37° C. EEA1 proteins were detected by Alexa 555-conjugated secondary antibody. Top left panels: cell nuclei stained with DAPI; Top right panels: FITC-labeled heptamer; bottom left panels: EEA1 antibody; bottom right panels: merged image of the three stainings.
Figure 16B:
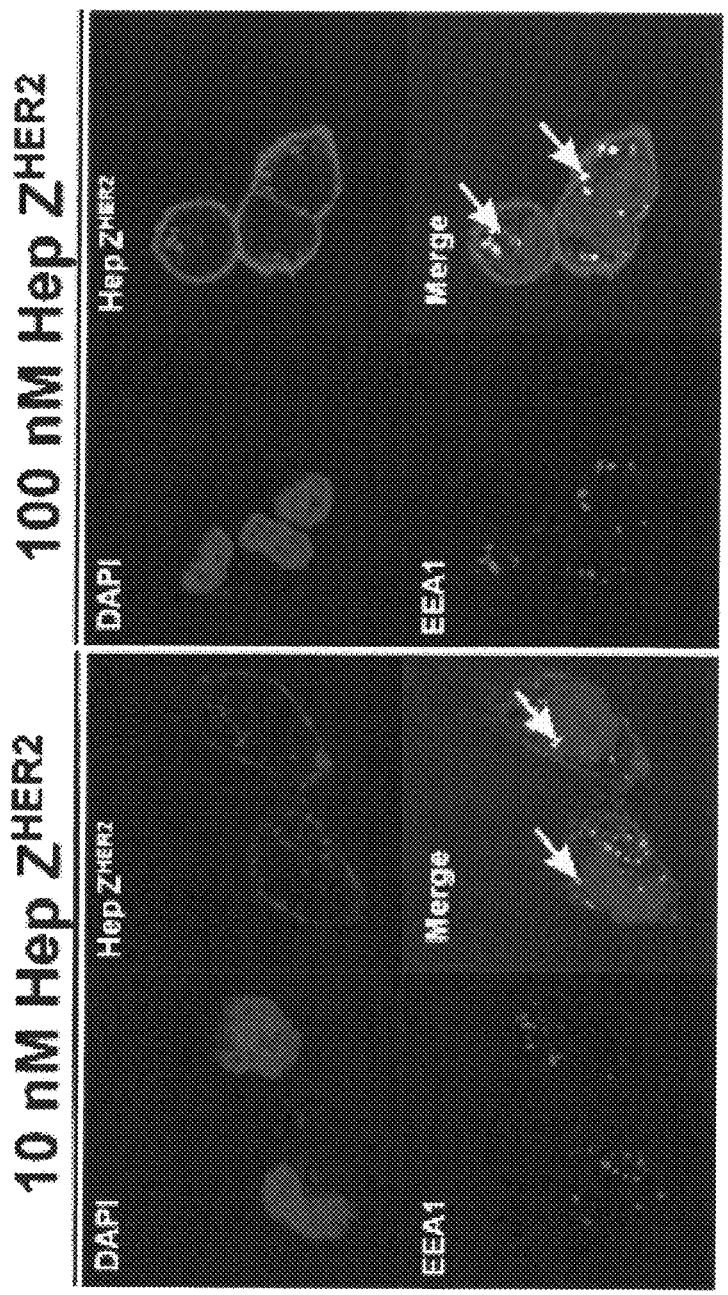

One of the exciting applications of targeting ligands is the delivery of imaging and/or therapeutic agents into specific cell types. Therefore, it is important to study whether targeting ligands can be internalized and to further investigate the sub-cellular localization of the internalized molecules. It is well known that the binding of EGF to EGFR promotes the internalization of the receptor through the endocytic pathway, and the internalized EGFR is strongly associated with an early endosome marker Early Endosome Antigen 1 (EEA1) that is enriched in endosomes [21]. To investigate the internalization and subsequent sub-cellular location of heptameric $Z^{EGFR}$ ligand, the targeting ligand was incubated with A431 cells at 37° C. for 2 h to promote its internalization. As illustrated in FIG. 16A, bright punctuated dots can be observed using confocal microscopy, demonstrating that FITC labeled heptameric $Z^{EGFR}$ (green fluorescence) was internalized and co-localized (white arrows) with the early endosome marker EEA1 (red fluorescence). However, some of the heptameric ligand signal did not overlap with EEA1. It is possible that some of heptameric ligands might escape from endosome or localize within late endosome that cannot be detected through EEA1. Similarly, the sub-cellular localization of heptameric $Z^{HER2}$ ligand was also investigated by incubating FITC labeled heptameric $Z^{HER2}$ ligands with SK-OV3 cells. It appears that heptameric $Z^{HER2}$ ligand also co-localized with EEA1 in endosomes (FIG. 16B), but more heptameric $Z^{HER2}$ ligands are present on cell surface when compared to the heptameric $Z^{EGFR}$ ligand. These findings clearly demonstrated that both heptameric targeting ligands were internalized and co-localized with EEA1 in endosomes.

Cellular Toxicity of the Heptameric Targeting Ligands

The internalization property of the heptameric ligands may be used for the intracellular delivery of a variety of agents such as anti-cancer drugs and imaging agents. However, an ideal targeting ligand must have minimal cellular toxicity. To examine the degree of cellular toxicity of the heptameric ligands, their effect on cell proliferation was assessed by the MTS assay. A high concentration of an appropriate heptameric ligand (1 μM) was incubated with EGFR-positive A431 or HER2-positive SK-OV3 cells. The anti-cancer drug cisplatin that interferes with cancer cell growth by inhibiting DNA metabolism through its binding to DNA was used as a positive control [26]. FIG. 10 illustrates that none of the heptameric ligands showed any detectable cell growth inhibition, while cisplatin at 10 μM inhibited cell proliferation to 50%. These results indicate that the heptameric targeting ligands by themselves are not toxic to cells under the conditions tested.

The role of multivalency in enhancing affinity of a ligand towards its target has been well studied [1]. The ideal targeting ligand with desired multivalency should be composed of multiple target-binding moieties displayed in parallel surrounding a multimeric core with unusually high stability. However, the generation of novel multivalent targeting ligands with desired properties, such as high stability and significantly improved functional affinity, is a difficult task. These studies demonstrate the first successful generation of heptameric targeting ligands using the heptamerization domain from the Archaeal RNA binding protein (FIGS. 11A-B). On the basis of these findings, it appears that the AF-Sm1 domain has several unique advantages to serve as an ideal scaffold for heptamerization of targeting ligands. These features include its cysteine-free amino acid sequence, spontaneous and highly efficient self-assembly process, exceptionally high stability against heat and protease-induced degradation, economical and high expression level in E. coli, and non-existing cellular toxicity.

In addition to a robust heptameric core, it is necessary to have an affinity moiety and a flexible linker to make a functional heptameric targeting ligand possible. This heptamerization system should allow for the use of any target-binding protein domains or short peptides isolated from a highly diversified protein domain or peptide library using various in vitro selections or directed molecular evolutions, including phage display, yeast display, bacterial display, ribosome display, and mRNA display. As examples, a PSMA-binding short peptide, or an EGFR- or a HER2-binding Z domain (~7 kDa) was used as the targeting moiety [18,19]. Unlike display of short peptides with just a few amino acids, display of seven protein domains at the top of a heptameric core without affecting the right geometry is challenging. The AF-Sm1 domain-based heptameric core is very compact and rigid, with the outer and inner diameters of 65 Å and 13 Å, respectively [16]. To facilitate the parallel display of seven AF-Sm1 domains, a flexible hinge linker was introduced between the target binding moiety and the heptamerization domain, which presumably provides greater inter-unit spacing so that each monomeric domain can be properly folded without disrupting the heptameric complex. Since multiple affinity units are presented to the targets on the cell membrane at a very close distance, the free energy of target binding with the heptameric ligand should be much higher than that with the monomeric ligand. Indeed, significantly improved target-binding strength of the heptameric ligands was observed when compared to the respective monomeric ligands.

The heptameric ligands were highly stable as demonstrated by their efficient formation even under harsh denaturing conditions, such as SDS- or heat-induced denaturation. No detectable monomeric ligand was observed under native conditions, suggesting that the small amount of monomeric form observed in the SDS-PAGE gels is likely due to the dissociation of a small proportion of the heptamer under denaturing conditions. Moreover, the high stability of heptameric ligands was demonstrated by CD analysis and protease-mediate degradation. The heptameric ligands were as stable as their monomeric counterparts as the temperature was raised to 94° C. during CD analysis. The minimal degradation by thermolysin, a highly active protease at high temperature, provided further evidence that the heptameric ligands have exceptional high stability. Each heptameric ligand maintains its target-binding specificity without cross reactivity. The in vitro target-binding strength of the heptameric ligands was significantly enhanced (up to 5000 fold) compared to the monomeric ligands. This is presumably due to the greatly reduced dissociation rates in heptameric targeting ligands.

The receptor-bound heptameric ligands were efficiently internalized and further co-localized with the early endosome marker EEA1. This finding indicates that the heptameric system can be utilized as a carrier for intracellular delivery of various anticancer agents. These results demonstrate that the heptameric targeting system described herein has great potential to be widely used for various in vivo applications.

The heptameric system has several unique advantages. First, the heptameric targeting ligand exists predominantly as a heptamer without any detectable intermediate forms. This is very different from the pentameric ligand that is present as a mixture of tri-, tetra-, and pentameric forms that complicate the purification process [20]. Second, the spontaneous and highly efficient self-assembly of the heptameric ligand is totally independent on the disulfide bond(s), but relies on the extensive inter-subunit hydrogen bonding, hydrophobic and electrostatic interactions. In contrast, the pentameric complexes rely on the critical inter-subunit disulfide bonds to maintain their multimeric structure. Third, the cysteine-free nature of the heptameric ligand can greatly facilitate its site-specific conjugation with other biomolecules, such as anticancer agents or nanoparticles, by introduction of the only cysteine at the N- or C-terminus. The facile and economic generation of these high-avidity affinity molecules makes them a valuable complement to the conventional antibody-based targeting ligands for both in vitro and in vivo applications. One additional advantage of the heptameric system is the spontaneous increase of the molecular weight from 18 kDa in monomer to greater than 130 kDa in heptamer, which could presumably extend the in vivo half-life of these ligands by reducing kidney clearance.

These results demonstrate that heptameric targeting ligands with high stability, significantly enhanced avidity, and non-toxicity can be easily generated through a facile and highly efficient self-assembly process. Although the heptameric targeting ligands demonstrated here are for binding with PSMA, EGFR or HER2 receptors as examples, the same approach can be generally applied to the rapid generation of high-avidity affinity molecules based on other target-binding moieties such as short homing peptides, single domain antibody mimics, and natural antibody fragments. It is worth mentioning that the AF-Sm1 domain is a robust RNA-binding complex [15], making it possible to use the heptameric ligands described here for the targeted delivery of nucleic acid drugs by an add-and-mix strategy.

REFERENCES FOR EXAMPLE 2

1. Deyev S M, Lebedenko E N (2008) Multivalency: the hallmark of antibodies used for optimization of tumor targeting by design. *Bioessays,* 30, 904-918.
2. Bird R E, Hardman K D, Jacobson J W, Johnson S, Kaufman B M. (1988) Single-chain antigen binding proteins. *Science,* 242, 423-426.
3. Yokota T, Milenic D E, Whitlow M, Schlom J (1992) Rapid tumor penetration of a single chain Fv and comparison with other immunoglobulin forms. *Cancer Res,* 52, 3402-3408.
4. Pluckthun A, Pack P (1997) New protein engineering approaches to multivalent and bispecific antibody fragments. *Immunotechnology,* 3, 83-105.
5. Crothers D M, Metzger H (1972) The influence of polyvalency on the binding properties of antibodies. *Immunochemistry,* 9, 341-357.
6. Trejtnar F, Laznicek M (2002) Analysis of renal handling of radiopharmaceuticals. *Q J Nuc Med,* 46, 181-194.
7. Borsi L, Balza E, Carnemolla B, Sassi F, Castellani P (2003) Selective targeted delivery of TNF alpha to tumor blood vessels. *Blood,* 102, 4384-4392.
8. Pack P, Muller K, Zahn R, Pluckthun A (1995) Tetravalent miniantibodies with high avidity assembling in *Escherichia coli. J Mol Biol,* 246, 28-34.
9. Kubetzko S, Balic E, Waibel R, Zangemeister-Wittke U, Pluckthun A (2006) Pegylation and multimerization of the anti-p185 HER-2 single chain Fv fragment D5: effects on tumor targeting. *J Bio Chem* 281, 35186-35201.
10. Kipriyanov S M, Moldenhauer G, Schuhmacher J, Cochlovius B, Von der Leith C W (1999) Bispecific tandem diabody for tumor therapy with improved antigen binding and pharmacokinetics. *J Mol Biol* 293, 41-56.
11. Zhang J, Tanha J, Hirama T, Khieu N H, To R, et al. (2004) Pentamerization of single domain antibodies from phage libraries; a novel strategy for the rapid generation of high avidity antibody reagents. *J Mol Biol,* 335, 49-56.
12. Stone E, Hirama T, Tanha J, Tong-Sevinc H, Li S, et al, (2006) The assembly of single domain antibodies into bispecific decavalent molecule. *J Immunol Methods* 318, 88-94.
13. Terskikh A V, Le Doussal J M, Crameri R, Fisch, I, Mach J P (1997) Pentabody: a new type of high avidity binding protein. *Proc Natl Acad Sci USA* 94, 1663-1668.
14. Fattah O M, Cloutier S M, Kundig C, Felber L M, Gygi C M (2006) Pentabody-EGF: a novel apoptosis inducer targeting Erb1 receptor overexpressiong cancer cells. *Int J Cancer* 119, 2455-2463.
15. Toro I, Basquin J, Teo-Dreher H, Suck D (2002) Archaelsm proteins form heptameric and hexameric complexes: crystal structures of the sm1 and sm2 proteins from the hyperthermophile *archaeoglobus fulgidus. J Mol Biol.* 320, 129-142.
16. Toro I, Thore S, Mayer C, Basquin J, Seraphin B, et al. (2001) RNA binding Sm core domain: X-ray structure and functional analysis of an archaeal Sm protein complex. *EMBO J.* 20, 2293-2303.
17. Beck K, Gambee J E, Bohan C A, Bachinger H P (1996) The C-terminal domain of cartilage matrix protein assembles into a triple-stranded alpha-helical coiled-coil structure. *J Mol Biol.* 256, 909-923
18. Orlova A, Magnusson M, Eriksson T L, Nilsson M, Larsson B, et al. (2006) Tumor imaging using a picomolar affinity HER2 binding affibody molecule. *Cancer Res.* 66, 4339-4348.
19. Friedman M, Orlova A, Johansson E, Eriksson T L, Holden-Guthenberg I, et al. (2008) Directed evolution to low nanomolar affinity of a tumor-targeting epidermal growth factor receptor binding affibody molecule. *J Mol Biol.* 376, 1388-1402.

20. Duan J, Wu J, Valencia Calif., Liu R. (2007) Fibronectin type III domain based monobody with high avidity. *Biochemistry*. 46, 12656-12664.
21. Leonard D, Hayakawa A, Lawe D, Lambright D, Bellve K D, et al. (2008) Sorting of EGF and transferring at the plasma membrane and by cargo-specific signaling to EEA1-enriched endosomes. *J Cell Sci*. 121, 3445-3458.
22. Nordberg E, Ekerljung L, Sahlberg S H, Carlsson J, Lennartsson J, et al. (2010) Effects of an EGFR-binding affibody molecule on intracellular signaling pathways. *Int J Oncol*. 36, 967-972.
23. Gostring L, Chew M T, Orlova A, Hoiden-Guthenberg I, Wennborg A, et al. (2010) Quantification of internalization of EGFR-binding affibody molecules: Methodological aspects. *Int J Oncol*. 36, 757-763.
24. Burke P, Schooler K, Wiley H S (2001) Regulation of epidermal growth factor receptor signaling by endocytosis and intracellular trafficking. *Mol. Bio. Cell*, 12, 1897-1910.
25. Govindarajan S, Sivakumar J, Garimidi P, Rangaraj N, Gopal V (2012) Targeting human epidermal growth factor receptor 2 by a cell-penetrating peptide-affibody bioconjugate. *Biomaterials*. 33, 2570-2582.
26. Ishida S, Lee J, Thiele D J, Herskowitz I (2002) Uptake of the anticancer drug cisplatin mediated by the copper transporter Ctrl in yeast and mammals. *Proc Natl Acad Sci*. 99, 14298-14302.
27. Bjorkelund H, Gedda L, Barta P, Malmqvist M, Andersson K (2011) Gefitinib induces epidermal growth factor receptor dimmers which alters the interaction characteristics with $^{125}$I-EGF. *PLOS ONE*, 6, e24739.
28. Lyakhov I, Zielinski R, Kuban M, Kramer-Marek G, Fisher R, et al. (2010) HER2- and EGFR-specific affiprobes: novel recombinant optical probes for cell imaging. *Chem BioChem*. 11, 345-350.
29. Benhabbour S R, Luft J C, Kim D, Jain A, Wadhwa S, et al. (2012) In vitro and in vivo assessment of targeting lipid-based nanoparticles to the epidermal growth factor receptor (EGFR) using a novel heptameric $Z^{EGFR}$ domain, *Journal of Controlled Release*. 158, 63-71.
30. Aggarwal, S., Singh, P., Topaloglu, O., Isaacs, J. T., & Denmeade, S. R. (2006). A dimeric peptide that binds selectively to prostate-specific membrane antigen and inhibits its enzymatic activity. *Cancer Res*. 66, 9171-9177.

Example 3

A 7Ring (Heptamer) that Delivers Therapeutic RNAs and Small Molecule Drugs

Another application of this invention is for facile self-loading of oligonucleotide or small molecule payloads through self-assembly without the need of any chemical conjugation. The introduction of a targeting ligand to si/shRNA-containing particles, either directly or indirectly, faces several major challenges. The technology of this invention uniquely addresses the challenge. The Sm or Sm-like (Lsm) protein that is used for self-assembly is involved in a variety of RNA processing events in all eukaryotic organisms. Its doughnut-shaped ring structure has a unique function to accommodate and specifically bind to uracil rich RNAs. This allows for the self-loading of nucleic acid-based payloads such as $(rU)_{10}$-containing si/shRNAs and micro RNAs (miRNAs) simply by adding-mixing (FIG. 17A).

Figure 17:
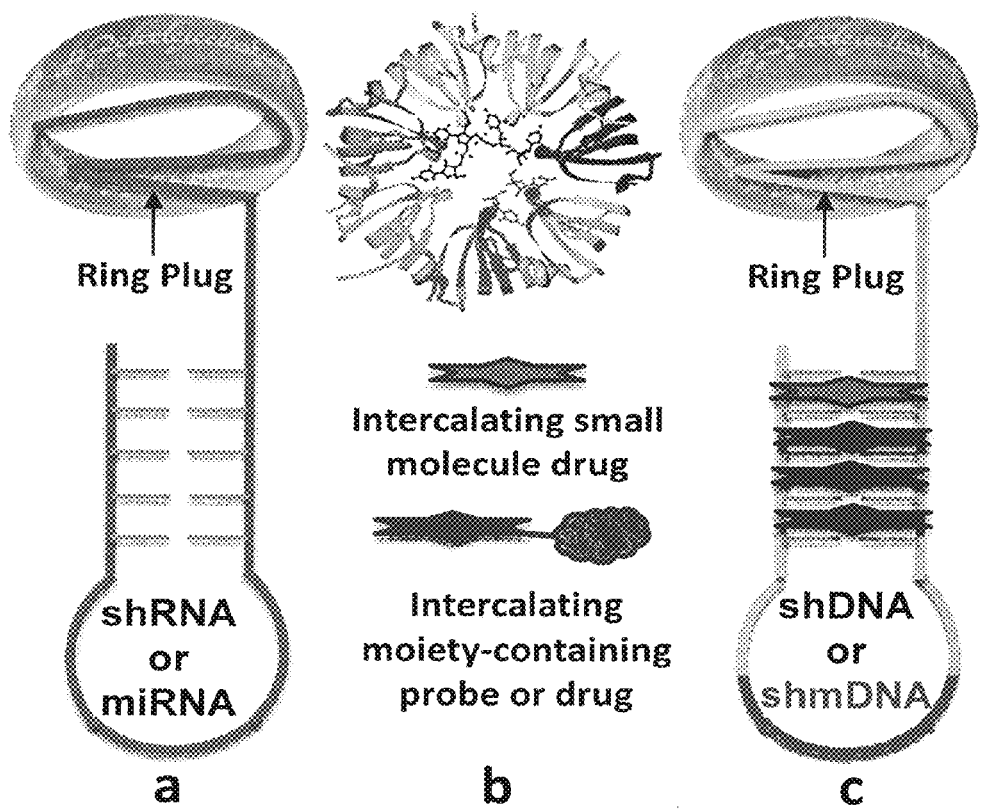
FIGS. 17A-C. Self-assembly of two targeting delivery platforms by adding and mixing. (A) 7Ring-shRNA; (C) 7Ring-shDNA/intercalator. The shRNA or shDNA is extended at 5' or 3' end with an $(rU)_{10}$ or $(dT)_{10}$ sequence that specifically plugs into the 7Ring socket. (B) The binding for 7Ring socket and the plug sequence. Intercalators can be intercalating drugs (e.g., Dox) or theranostic agents or probes containing a dsDNA intercalating moiety.

In addition to the self-loading of oligo(rU)-containing si/shRNAs, the heptamer (7Ring) of this invention can also specifically recognize and tightly bind oligo(dT), making it possible to self-load, e.g., $(dT)_{10}$-containing small hairpin DNAs (shDNAs) (FIG. 17C). The availability of this self-assembly 7Ring/$(dT)_n$-shDNA system allows for the easy incorporation of small molecule intercalating drugs (e.g., doxorubicin) or any intercalating moiety-containing molecule(s) (FIG. 17B), and therefore for targeted delivery of theranostic chemicals and/or molecule probes. Since no chemical conjugation is required and the self-loading process is independent of the sequence of the payloads, any combinations of payloads, including a pool of si/shRNAs or a mixture of intercalating agents, can be delivered in the same mixture, making it possible to integrate the targeting ligand and for the payload to be delivered as one protein-nucleic acid complex, thereby greatly facilitating the analysis of combined effects of different theranostic agents.

Figure 18:
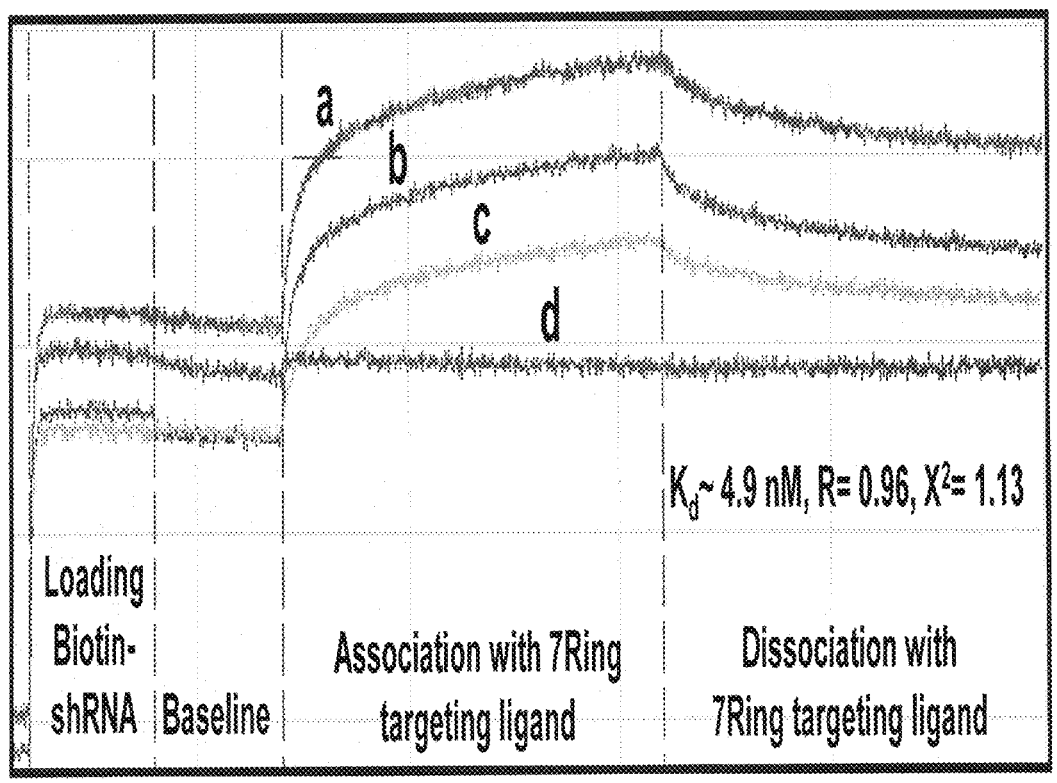
FIG. 18. Binding affinity of $(rU)_{10}$-containing shRNA with 7Ring targeting ligand, measured by using Octet BLI with biotin-shRNA immobilized on streptavidin biosensor.
Figure 19:
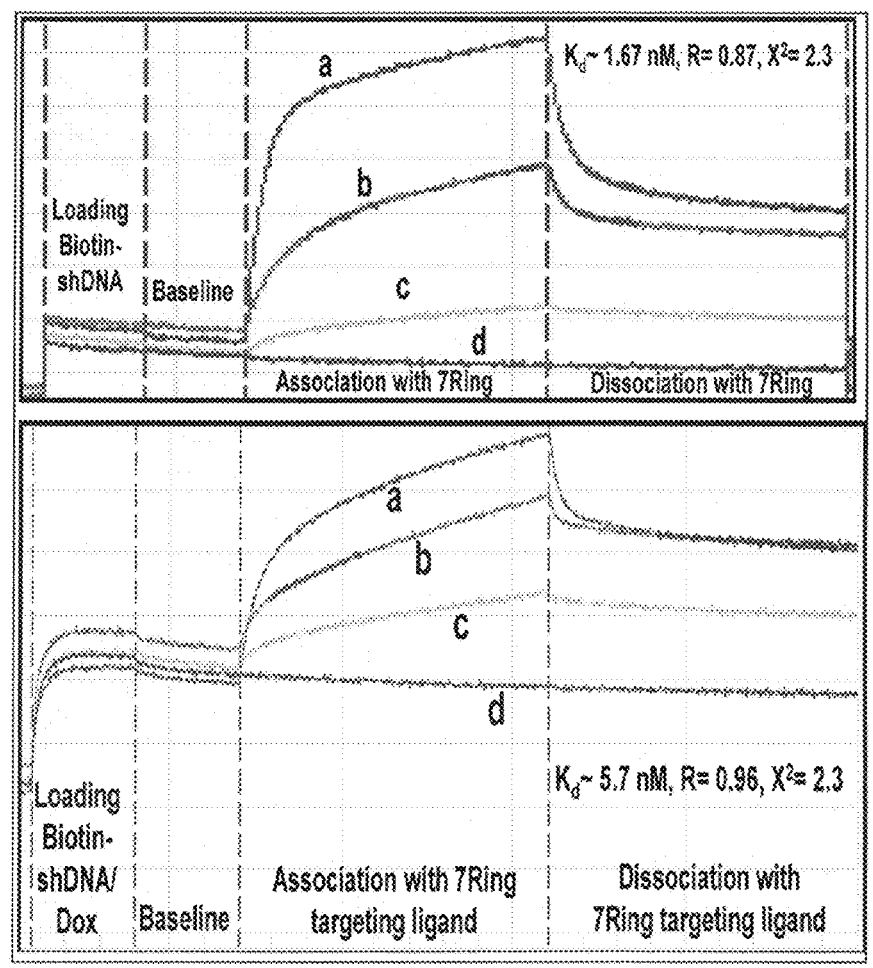
FIG. 19. Binding affinity of $(dT)_{10}$-containing shDNA with 7Ring targeting ligand, measured by using Octet BLI with biotin-shDNA immobilized on streptavidin biosensor (bottom) or without (top) a DNA intercalator (doxorubicin).

Studies were also conducted to determine whether the heptamer of this invention (7Ring platform) has the desired feature of efficiently capturing a $(rU)_{10}$ plug-containing shRNA through a self-assembly process. As shown in FIG. 18, the interaction between the 7Ring targeting ligand and an shRNA$^{Luc}$ with a 3' $(rU)_{10}$ terminal extension is highly specific, with a binding affinity around 5 nM, whereas its interaction with shRNAs with other terminal extension sequences is below detection limit (data not shown). Studies were also done to examine whether the 7Ring platform has the desired feature of efficiently capturing a $(dT)_{10}$ plug-containing shDNA through a self-assembly process. As demonstrated in FIG. 19, the engineered 7Ring ligand can tightly and specifically bind to $(dT)_{10}$-containing shDNA through its 3' terminal $(dT)_{10}$ extension, with an affinity around 1.67 nM. The double-stranded stem on shDNA can serve as a universal carrier for any small molecule drug(s) or probes containing a DNA intercalating moiety. Indeed, when shDNA was loaded with intercalating molecules such as doxorubicin, high binding affinity between 7Ring ligand and $(dT)_{10}$-shDNA/Dox was still very retained (~5.7 nM).

It will be understood by those of skill in the art that numerous and various modifications can be made without departing from the spirit of the present invention. Therefore, it should be clearly understood that the forms of the present invention are illustrative only and are not intended to limit the scope of the present invention.

All publications, patent applications, patents, patent publications, sequences identified by GenBank® database accession numbers and other references cited herein are incorporated by reference in their entireties for the teachings relevant to the sentence and/or paragraph in which the reference is presented.

The invention is defined by the following claims, with equivalents of the claims to be included therein.

TABLE 1

Binding constants of each of the monomeric and heptameric molecules

| | $K_a$(1/Ms) | $K_d$(1/s) | $K_D$(M) |
|---|---|---|---|
| ZEGFR-Monomer | $6.07 \times 10^4$ | $1.59 \times 10^{-4}$ | $2.62 \times 10^{-9}$ |
| ZEGFR-Heptamer | $1.91 \times 10^4$ | $5.67 \times 10^{-7}$ | $2.9 \times 10^{-11}$ |
| ZHER2-Monomer | $1.69 \times 10^5$ | $2.95 \times 10^{-4}$ | $1.75 \times 10^{-9}$ |
| ZHER2-Heptamer | $3.15 \times 10^4$ | $7.15 \times 10^{-8}$ | $2.27 \times 10^{-12}$ |
| PSMA-Heptamer | $5.47 \times 10$ | $1.09 \times 10^{-6}$ | $2 \times 10^{-8}$ |

TABLE 2

Amino acid sequences of each component of the heptameric targeting ligands.

| | Amino acids |
|---|---|
| Z$^{EGFR}$ | MVDNKFNKEM WAAWEEIRNL PNLNGWQMTA FIASLVDDPS QSANLLAEAK KLNDAQAPK |
| Z$^{HER2}$ | MVDNKFNKEM RNAYWEIALL PNLNNQQKRA FIRSLYGDPS QSANLLAEAK KLNDAQAPK |

TABLE 2-continued

Amino acid sequences of each component of the heptameric targeting ligands.

| | Amino acids |
|---|---|
| SP$^{PSMA}$ | MWQPDTAHHWATL |
| Hinge Linker | GPQPQPKPQPK PEPEPQPQGG |
| Heptamerization domain | MPPRPLDVLN RSLKSPVIVR LKGGREFRGT LDGYDIHMNL VLLDAEEIQN GEVVRKVGSV VIRGDTVVFV SPAPGGE |

What is claimed is:

1. A self-assembling molecule in heptameric form, comprising:
   a) a monomer comprising a multimerization domain of Archaeal Sm1 (AF-Sm1) protein or SM-like ribonucleoprotein, comprising an amino acid sequence selected from the group consisting of:
      A) at least about 50 residues of the amino acid sequence of SEQ ID NO:1 (MPPRPLDVLN RSLKSPVIVR LKGGREFRGT LDGYDIHMNL VLLDAEEIQN GEVVRKVGSV VIRGDTVVFV SPAPGGE);
      B) at least about 50 residues of the amino acid sequence of SEQ ID NO:2 (MARPLDVLNK ALKTPVLVRL KGGREFRGTL DGYDIHMNLV LVDAEEIQNG EVVRKLGSVV IRGDTVVFVS PSQ);
      C) at least about 50 residues of the amino acid sequence of SEQ ID NO:3 (MAKRPLDVLN KALQTPVLVR LKGGREFRGI LNGYDIHMNI VLENAEEIQN GEVVRKLGSV VIRGDTVVFV SPSE);
      D) at least about 50 residues of the amino acid sequence of SEQ ID NO:4 (MANRPLDVLN KALQTPVLVR LKGGREFRGI LNGYDIHMNL VLQNAEEIQG GEVIRKLGSV VIRGDTVVFV SPSP);
      E) at least about 50 residues of the amino acid sequence of SEQ ID NO:5 (MGNRPLDILN NALNTAVIVR LKGAREFRGT LQGYDVHMNL VLDEAEEIKE GEIIRKIGSV VVRGDNVVYV SP);
      F) at least about 50 residues of the amino acid sequence of SEQ ID NO:6 (MANRPLDILN NALNTPVIVR LKGAREFRGE LQGYDVHMNL VLDNAEELKD GEIVRKLGSV VIRGDNVVYL SP);
      G) at least about 50 residues of the amino acid sequence of SEQ ID NO:7 (RPLDAL GNSLNSPVII KLKG-DREFRG VLKSFDLHMN LVLNDAEELE DGEV-TRRLGT VLIRGDNIVY ISP); and
      H) at least about 50 residues of the amino acid sequence of SEQ ID NO:8 (RPLDALGN SLNSPVIIKL KGDREFRGVL KSFDLHMNLV LNDAEELEDG EVTRRLGTVL IRGDNIVYIS), and
   b) a target binding domain or peptide attached to the monomer of (a), wherein the target binding domain or peptide is selected from the group consisting of:
      A) an epidermal growth factor receptor (EGFR)-binding Z domain comprising the amino acid sequence: VDNKFNKEMWAAWEEIRNLPNLNG-WQMTAFIASLVDDPSQSANLLAE-AKKLNDAQAPK (SEQ ID NO:20);
      B) a human epidermal growth factor receptor 2 (HER2) binding Z domain comprising the amino acid sequence: VDNKFNKEMRNAYWEIALLPNLN-NQQKRAFIRSLYDDPSQSANLLAE-AKKLNDAQAPK (SEQ ID NO:21);
      C) a prostate specific membrane antigen (PSMA)-binding peptide comprising the amino acid sequence: QKHHNYL (amino acid residues 79-85 of SEQ ID NO: 22);
      D) a PSMA-binding fibronectin type III (FN3) domain comprising the amino acid sequence: MGVSD-VPRDLEVVAATPTSLLISWDA-PAVTVRYYRITYGETGGNSPVQEFTVPGSKSTA TISGLKPGVDYTITVYAVTQKHHNYLPI-SINYRTEIDKPSQ (SEQ ID NO:22);
      E) a gastrin-releasing (GRP78) binding peptide comprising the amino acid sequence: WIFPWIQLGGS (SEQ ID NO:23);
      F) an EGFR-binding peptide comprising the amino acid sequence: YHWYGYTPQNVI (SEQ ID NO:24);
      G) a plectin-1-binding peptide comprising the amino acid sequence: KTLLPTPGGS (SEQ ID NO:25);
      H) a human epidermal growth factor receptor 3 (HER3) binding Z domain comprising the amino acid sequence: VDNKFNKERYSAYYEIWQLPNLN-VRQKAAFIGSLQDDPSQSANLLAE-AKKLNDAQAPK (SEQ ID NO:26);
      I) an $\alpha_v\beta_3$-binding FN3 domain comprising the amino acid sequence: MGVSDVPRDLEV-VAATPTSLLISWDAPAVTVRYYRI-TYGETGGNSPVQEFTVPGSKSTA TISGLK-PGVDYTITVYAVTPRGDWNEGSKPISINYRT (SEQ ID NO:27);
      J) a TNFα-binding FN3 domain comprising the amino acid sequence: MGVSDVPRDLEV-VAATPTSLLISWRPTSNPPRYYRI-TYGETGGNSPVQEFTVPPWASTAT ISGLK-PGVDYTITVYAVTAQTGHHLHDKPISINYRT (SEQ ID NO:28);
      K) a vascular endothelial growth factor receptor (VEGFR)-binding FN3 domain comprising the amino acid sequence: MGVSDVPRDLEV-VAATPTSLLISWRHPHFPTRYYRI-TYGETGGNSPVQEFTVPLQPPTAT ISGLK-PGVDYTITVYAVTDGRNGRLLSIPISINYRT (SEQ ID NO:29);
      L) a gastrin-releasing peptide comprising the amino acid sequence: GNHWAVGHLM (SEQ ID NO:30);
      M) an EGFR-binding Z domain ($Z^{EGFR}$) comprising the amino acid sequence: MVDNKFNKEM WAAWEEIRNL PNLNGWQMTA FIASLVDDPS QSANLLAEAK KLNDAQAPK (SEQ ID NO:31)
      N) a HER2-binding Z domain ($Z^{EGFR}$) comprising the amino acid sequence: MVDNKFNKEM RNAYWE-IALL PNLNNQQKRA FIRSLYGDPS QSAN-LLAEAK KLNDAQAPK (SEQ ID NO:32); and O) a PSMA-binding peptide (SP$^{PSMA}$) comprising the amino acid sequence: MWQPDTAHHWATL (SEQ ID N0:33).

2. The molecule of claim 1, wherein the target binding domain or peptide of (b) is attached via a linker peptide to the monomer of (a).

3. The molecule of claim 2, wherein the linker peptide is selected from the group consisting of:
a) a linker peptide comprising the amino acid sequence of SEQ ID NO:9 (GPQPQPKPQPK);
b) a linker peptide comprising the amino acid sequence of SEQ ID NO:10 (GGGGS)$_n$, wherein n is any number;
c) a linker peptide comprising the amino acid sequence of SEQ ID NO:11 (TPPTPSPSTPPTPSP);
d) a linker peptide comprising the amino acid sequence of SEQ ID NO:12 (EFPKSTPPGSSGGAP);
e) a linker peptide comprising the amino acid sequence of SEQ ID NO:13 (PQPQPQPKPQPKPEPE);
f) a linker peptide comprising the amino acid sequence of SEQ ID NO:14 (GGGS)$_n$, wherein n is any number;
g) a linker peptide comprising the amino acid sequence of SEQ ID NO: 15 (GSGSGS)$_n$, wherein n is any number;
h) a linker peptide comprising of the amino acid sequence of SEQ ID NO:011116 (TPPTPSP)$_n$, wherein n is any number;
i) a linker peptide comprising the amino acid sequence of SEQ ID NO:17 ((PQPQPK)$_n$, wherein n is any number;
j) a linker peptide comprising the amino acid sequence of SEQ ID NO:18 (PQPQPE)$_n$, wherein n is any number;
k) a linker peptide comprising the amino acid sequence of SEQ ID NO:19 (PEPEPQPQGG);
l) a linker peptide comprising the amino acid sequence of SEQ ID NO:34 (GPQPQPKPQPKPEPEPQPQGG); and
m) any combination of (a)-(l) above.

4. The molecule of claim 1, wherein the target binding domain or peptide of (b) is attached to the monomer of (a) at the amino terminus and/or at the carboxy terminus.

5. The molecule of claim 1, further comprising a histidine tag.

6. The molecule of claim 1, further comprising a diagnostic molecule, a therapeutic molecule, an imaging molecule or any combination thereof.

7. The molecule of claim 1, further comprising an amino-terminal and/or a carboxy-terminal cysteine for site-specific conjugation with a diagnostic molecule, a therapeutic molecule, an imaging molecule, a nanoparticle or any combination thereof.

8. The self-assembling molecule of claim 1, in heptameric form in the absence of any cysteine residues that maintain the oligomeric state.

9. A heptamer comprising seven self assembly molecules of claim 1.

10. A heptamer comprising seven self assembly molecules of claim 1, lacking any cysteine residues that maintain the oligomeric state.

11. The heptamer of claim 9, having a binding strength for a target molecule that is increased from about 100 fold to about 10,000 fold, as compared with a monomer control.

12. A method of producing a heptamer having a binding strength for a target molecule that is increased from about 100 fold to about 10,000 fold as compared with a monomer control, comprising:
a) combining a plurality of the self assembly molecules of claim 1 under conditions whereby the molecules self assemble into heptamers; and
b) optionally isolating the heptamers, thereby producing the heptamer.

13. A heptamer produced by the method of claim 12.

14. A method of detecting and/or localizing cancer cells in a subject, comprising administering to the subject an effective amount of the heptamer of claim 9, wherein the targeting domain or peptide is specific for a target molecule on the surface of cancer cells in the subject and the heptamer further comprises an imaging molecule and/or detectable molecule, whereby the heptamer binds the target molecule on the surface of cancer cells in the subject and the imaging molecule is visualized and/or the detectable molecule is detected at its binding location in the subject, thereby detecting and/or localizing cancer cells in the subject.

15. A method of diagnosing cancer in a subject, comprising administering to the subject an effective amount of the heptamer of claim 9, wherein the targeting domain or peptide is specific for a target molecule on the surface of cancer cells in the subject and the heptamer further comprises an imaging molecule and/or detectable molecule, whereby the heptamer binds the target molecule on the surface of cancer cells in the subject and the imaging molecule is visualized and/or the detectable molecule is detected on cancer cells in the subject, thereby diagnosing cancer in the subject.

16. The method of claim 14, wherein the imaging molecule comprises an MRI contrast agent, a radioisotope, $^{64}$Cu-ATSM, $^{18}$F-FDG, fluoride, FLT, FMISO, gallium, technetium-99m, a near-infrared (IR) fluorescence molecule, a nanoparticle-containing imaging agent or any combination thereof.

17. The method of claim 14, wherein the target molecule comprises an extracellular domain of a cell surface receptor selected from the group consisting of an epidermal growth factor receptor family member, EGFR, HER2, HER3, c-MET, VEGFR, insulin receptor, insulin-like growth factor receptor, prostate specific membrane antigen, mesothelin, hepsin, an integrin, mucin, MUC16, a cell surface cluster of differentiation (CD) molecule, CD20, CD22, CD30, CD33, CD44, CD56, and any combination thereof.

18. A kit comprising the heptamer of claim 9.

19. A composition comprising the heptamer of claim 9 in a pharmaceutically acceptable carrier.

20. The self-assembling molecule of claim 1, wherein the monomer of (a) comprises the amino acid sequence MPPRPLDVLN RSLKSPVIVR LKGGREFRGT LDGYDI-HMNL VLLDAEEIQN GEVVRKVGSV VIRGDTVVFV SPAPGGE (SEQ ID NO:1) and the target binding domain or peptide of (b) comprises the amino acid sequence MVDNK-FNKEM WAAWEEIRNL PNLNGWQMTA FIASLVDDPS QSANLLAEAK KLNDAQAPK (SEQ ID NO:31) and the monomer of (a) is attached to the target binding domain of (b) via a linker comprising the amino acid sequence GPQPQP-KPQPK PEPEPQPQGG (SEQ ID NO:34).

21. The self-assembling molecule of claim 1, wherein the monomer of (a) comprises the amino acid sequence MPPRPLDVLN RSLKSPVIVR LKGGREFRGT LDGYDI-HMNL VLLDAEEIQN GEVVRKVGSV VIRGDTVVFV SPAPGGE (SEQ ID NO:1) and the target binding domain or peptide of (b) comprises the amino acid sequence MVDNK-FNKEM RNAYWEIALL PNLNNQQKRA FIRSLYGDPS QSANLLAEAK KLNDAQAPK (SEQ ID NO:32) and the monomer of (a) is attached to the target binding domain of (b) via a linker comprising the amino acid sequence GPQPQP-KPQPK PEPEPQPQGG (SEQ ID NO:34).

22. The self-assembling molecule of claim 1, wherein the monomer of (a) comprises the amino acid sequence MPPRPLDVLN RSLKSPVIVR LKGGREFRGT LDGYDI-HMNL VLLDAEEIQN GEVVRKVGSV VIRGDTVVFV SPAPGGE (SEQ ID NO:1) and the target binding domain or peptide of (b) comprises the amino acid sequence MWQPD-TAHHWATL (SEQ ID NO:33) and the monomer of (a) is attached to the target binding domain of (b) via a linker comprising the amino acid sequence GPQPQPKPQPK PEP-EPQPQGG (SEQ ID NO:34).

* * * * *

SEQUENCE LISTING

<160> NUMBER OF SEQ ID NOS: 35

<210> SEQ ID NO 1
<211> LENGTH: 77
<212> TYPE: PRT
<213> ORGANISM: Archaeoglobus fulgidus

<400> SEQUENCE: 1

Met Pro Pro Arg Pro Leu Asp Val Leu Asn Arg Ser Leu Lys Ser Pro
1               5                   10                  15

Val Ile Val Arg Leu Lys Gly Gly Arg Glu Phe Arg Gly Thr Leu Asp
            20                  25                  30

Gly Tyr Asp Ile His Met Asn Leu Val Leu Leu Asp Ala Glu Glu Ile
        35                  40                  45

Gln Asn Gly Glu Val Val Arg Lys Val Gly Ser Val Val Ile Arg Gly
    50                  55                  60

Asp Thr Val Val Phe Val Ser Pro Ala Pro Gly Gly Glu
65                  70                  75

<210> SEQ ID NO 2
<211> LENGTH: 73
<212> TYPE: PRT
<213> ORGANISM: Ferroglobus placidus

<400> SEQUENCE: 2

Met Ala Arg Pro Leu Asp Val Leu Asn Lys Ala Leu Lys Thr Pro Val
1               5                   10                  15

Leu Val Arg Leu Lys Gly Gly Arg Glu Phe Arg Gly Thr Leu Asp Gly
            20                  25                  30

Tyr Asp Ile His Met Asn Leu Val Leu Val Asp Ala Glu Glu Ile Gln
        35                  40                  45

Asn Gly Glu Val Val Arg Lys Leu Gly Ser Val Val Ile Arg Gly Asp
    50                  55                  60

Thr Val Val Phe Val Ser Pro Ser Gln
65                  70

<210> SEQ ID NO 3
<211> LENGTH: 74
<212> TYPE: PRT
<213> ORGANISM: Archaeoglobus profundus

<400> SEQUENCE: 3

Met Ala Lys Arg Pro Leu Asp Val Leu Asn Lys Ala Leu Gln Thr Pro
1               5                   10                  15

Val Leu Val Arg Leu Lys Gly Gly Arg Glu Phe Arg Gly Ile Leu Asn
            20                  25                  30

Gly Tyr Asp Ile His Met Asn Ile Val Leu Glu Asn Ala Glu Glu Ile
          35                  40                  45

Gln Asn Gly Glu Val Val Arg Lys Leu Gly Ser Val Ile Arg Gly
 50                  55                  60

Asp Thr Val Val Phe Val Ser Pro Ser Glu
65                  70

<210> SEQ ID NO 4
<211> LENGTH: 74
<212> TYPE: PRT
<213> ORGANISM: Archaeoglobus veneficus

<400> SEQUENCE: 4

Met Ala Asn Arg Pro Leu Asp Val Leu Asn Lys Ala Leu Gln Thr Pro
1               5                   10                  15

Val Leu Val Arg Leu Lys Gly Gly Arg Glu Phe Arg Gly Ile Leu Asn
                20                  25                  30

Gly Tyr Asp Ile His Met Asn Leu Val Leu Gln Asn Ala Glu Glu Ile
          35                  40                  45

Gln Gly Gly Glu Val Ile Arg Lys Leu Gly Ser Val Val Ile Arg Gly
 50                  55                  60

Asp Thr Val Val Phe Val Ser Pro Ser Pro
65                  70

<210> SEQ ID NO 5
<211> LENGTH: 72
<212> TYPE: PRT
<213> ORGANISM: Methanohalophilus mahii

<400> SEQUENCE: 5

Met Gly Asn Arg Pro Leu Asp Ile Leu Asn Asn Ala Leu Asn Thr Ala
1               5                   10                  15

Val Ile Val Arg Leu Lys Gly Ala Arg Glu Phe Arg Gly Thr Leu Gln
                20                  25                  30

Gly Tyr Asp Val His Met Asn Leu Val Leu Asp Glu Ala Glu Glu Ile
          35                  40                  45

Lys Glu Gly Glu Ile Ile Arg Lys Ile Gly Ser Val Val Val Arg Gly
 50                  55                  60

Asp Asn Val Val Tyr Val Ser Pro
65                  70

<210> SEQ ID NO 6
<211> LENGTH: 72
<212> TYPE: PRT
<213> ORGANISM: Methanosalsum zhilinae

<400> SEQUENCE: 6

Met Ala Asn Arg Pro Leu Asp Ile Leu Asn Asn Ala Leu Asn Thr Pro
1               5                   10                  15

Val Ile Val Arg Leu Lys Gly Ala Arg Glu Phe Arg Gly Glu Leu Gln
                20                  25                  30

Gly Tyr Asp Val His Met Asn Leu Val Leu Asp Asn Ala Glu Glu Leu
          35                  40                  45

Lys Asp Gly Glu Ile Val Arg Lys Leu Gly Ser Val Val Ile Arg Gly
 50                  55                  60

Asp Asn Val Val Tyr Leu Ser Pro
65                  70

-continued

<210> SEQ ID NO 7
<211> LENGTH: 69
<212> TYPE: PRT
<213> ORGANISM: Methanobacterium thermoautotrophicum

<400> SEQUENCE: 7

```
Arg Pro Leu Asp Ala Leu Gly Asn Ser Leu Asn Ser Pro Val Ile Ile
1               5                   10                  15

Lys Leu Lys Gly Asp Arg Glu Phe Arg Gly Val Leu Lys Ser Phe Asp
            20                  25                  30

Leu His Met Asn Leu Val Leu Asn Asp Ala Glu Glu Leu Glu Asp Gly
        35                  40                  45

Glu Val Thr Arg Arg Leu Gly Thr Val Leu Ile Arg Gly Asp Asn Ile
    50                  55                  60

Val Tyr Ile Ser Pro
65
```

<210> SEQ ID NO 8
<211> LENGTH: 68
<212> TYPE: PRT
<213> ORGANISM: Methanothermobacter thermautotrophicus

<400> SEQUENCE: 8

```
Arg Pro Leu Asp Ala Leu Gly Asn Ser Leu Asn Ser Pro Val Ile Ile
1               5                   10                  15

Lys Leu Lys Gly Asp Arg Glu Phe Arg Gly Val Leu Lys Ser Phe Asp
            20                  25                  30

Leu His Met Asn Leu Val Leu Asn Asp Ala Glu Glu Leu Glu Asp Gly
        35                  40                  45

Glu Val Thr Arg Arg Leu Gly Thr Val Leu Ile Arg Gly Asp Asn Ile
    50                  55                  60

Val Tyr Ile Ser
65
```

<210> SEQ ID NO 9
<211> LENGTH: 11
<212> TYPE: PRT
<213> ORGANISM: Artificial
<220> FEATURE:
<223> OTHER INFORMATION: Linker sequence

<400> SEQUENCE: 9

```
Gly Pro Gln Pro Gln Pro Lys Pro Gln Pro Lys
1               5                   10
```

<210> SEQ ID NO 10
<211> LENGTH: 5
<212> TYPE: PRT
<213> ORGANISM: Artificial
<220> FEATURE:
<223> OTHER INFORMATION: Linker sequence

<400> SEQUENCE: 10

```
Gly Gly Gly Gly Ser
1               5
```

<210> SEQ ID NO 11
<211> LENGTH: 15
<212> TYPE: PRT
<213> ORGANISM: Artificial
<220> FEATURE:
<223> OTHER INFORMATION: Linker sequence

<400> SEQUENCE: 11

Thr Pro Pro Thr Pro Ser Pro Ser Thr Pro Pro Thr Pro Ser Pro
1               5                   10                  15

<210> SEQ ID NO 12
<211> LENGTH: 16
<212> TYPE: PRT
<213> ORGANISM: Artificial
<220> FEATURE:
<223> OTHER INFORMATION: Linker sequence

<400> SEQUENCE: 12

Glu Phe Pro Lys Pro Ser Thr Pro Pro Gly Ser Ser Gly Gly Ala Pro
1               5                   10                  15

<210> SEQ ID NO 13
<211> LENGTH: 16
<212> TYPE: PRT
<213> ORGANISM: Artificial
<220> FEATURE:
<223> OTHER INFORMATION: Linker sequence

<400> SEQUENCE: 13

Pro Gln Pro Gln Pro Gln Pro Lys Pro Gln Pro Lys Pro Glu Pro Glu
1               5                   10                  15

<210> SEQ ID NO 14
<211> LENGTH: 4
<212> TYPE: PRT
<213> ORGANISM: Artificial
<220> FEATURE:
<223> OTHER INFORMATION: Linker sequence

<400> SEQUENCE: 14

Gly Gly Gly Ser
1

<210> SEQ ID NO 15
<211> LENGTH: 6
<212> TYPE: PRT
<213> ORGANISM: Artificial
<220> FEATURE:
<223> OTHER INFORMATION: Linker sequence

<400> SEQUENCE: 15

Gly Ser Gly Ser Gly Ser
1               5

<210> SEQ ID NO 16
<211> LENGTH: 7
<212> TYPE: PRT
<213> ORGANISM: Artificial
<220> FEATURE:
<223> OTHER INFORMATION: Linker sequence

<400> SEQUENCE: 16

Thr Pro Pro Thr Pro Ser Pro
1               5

<210> SEQ ID NO 17
<211> LENGTH: 6
<212> TYPE: PRT
<213> ORGANISM: Artificial
<220> FEATURE:
<223> OTHER INFORMATION: Linker sequence -continued

```
<400> SEQUENCE: 17

Pro Gln Pro Gln Pro Lys
1               5

<210> SEQ ID NO 18
<211> LENGTH: 6
<212> TYPE: PRT
<213> ORGANISM: Artificial
<220> FEATURE:
<223> OTHER INFORMATION: Linker sequence

<400> SEQUENCE: 18

Pro Gln Pro Gln Pro Glu
1               5

<210> SEQ ID NO 19
<211> LENGTH: 10
<212> TYPE: PRT
<213> ORGANISM: Artificial
<220> FEATURE:
<223> OTHER INFORMATION: Linker sequence

<400> SEQUENCE: 19

Pro Glu Pro Glu Pro Gln Pro Gln Gly Gly
1               5                   10

<210> SEQ ID NO 20
<211> LENGTH: 58
<212> TYPE: PRT
<213> ORGANISM: Homo sapiens

<400> SEQUENCE: 20

Val Asp Asn Lys Phe Asn Lys Glu Met Trp Ala Ala Trp Glu Glu Ile
1               5                   10                  15

Arg Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Homo sapiens

<400> SEQUENCE: 21

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 22
<211> LENGTH: 100
<212> TYPE: PRT
<213> ORGANISM: Homo sapiens

<400> SEQUENCE: 22
```

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Gln Lys
65                  70                  75                  80

His His Asn Tyr Leu Pro Ile Ser Ile Asn Tyr Arg Thr Glu Ile Asp
                85                  90                  95

Lys Pro Ser Gln
            100

<210> SEQ ID NO 23
<211> LENGTH: 11
<212> TYPE: PRT
<213> ORGANISM: Homo sapiens

<400> SEQUENCE: 23

Trp Ile Phe Pro Trp Ile Gln Leu Gly Gly Ser
1               5                   10

<210> SEQ ID NO 24
<211> LENGTH: 12
<212> TYPE: PRT
<213> ORGANISM: Homo sapiens

<400> SEQUENCE: 24

Tyr His Trp Tyr Gly Tyr Thr Pro Gln Asn Val Ile
1               5                   10

<210> SEQ ID NO 25
<211> LENGTH: 10
<212> TYPE: PRT
<213> ORGANISM: Homo sapiens

<400> SEQUENCE: 25

Lys Thr Leu Leu Pro Thr Pro Gly Gly Ser
1               5                   10

<210> SEQ ID NO 26
<211> LENGTH: 58
<212> TYPE: PRT
<213> ORGANISM: Homo sapiens

<400> SEQUENCE: 26

Val Asp Asn Lys Phe Asn Lys Glu Arg Tyr Ser Ala Tyr Tyr Glu Ile
1               5                   10                  15

Trp Gln Leu Pro Asn Leu Asn Val Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 27
<211> LENGTH: 96
<212> TYPE: PRT
<213> ORGANISM: Homo sapiens
```

```
<400> SEQUENCE: 27

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
            35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Pro Arg
65                  70                  75                  80

Gly Asp Trp Asn Glu Gly Ser Lys Pro Ile Ser Ile Asn Tyr Arg Thr
                85                  90                  95

<210> SEQ ID NO 28
<211> LENGTH: 96
<212> TYPE: PRT
<213> ORGANISM: Homo sapiens

<400> SEQUENCE: 28

Met Gly Val Ser Asp Val Pro Arg Asp Leu Glu Val Val Ala Ala Thr
1               5                   10                  15

Pro Thr Ser Leu Leu Ile Ser Trp Arg Pro Thr Ser Asn Pro Pro Arg
            20                  25                  30

Tyr Tyr Arg Ile Thr Tyr Gly Glu Thr Gly Gly Asn Ser Pro Val Gln
            35                  40                  45

Glu Phe Thr Val Pro Pro Trp Ala Ser Thr Ala Thr Ile Ser Gly Leu
    50                  55                  60

Lys Pro Gly Val Asp Tyr Thr Ile Thr Val Tyr Ala Val Thr Ala Gln
65                  70                  75                  80

Thr Gly His His Leu His Asp Lys Pro Ile Ser Ile Asn Tyr Arg Thr
                85                  90                  95

<210> SEQ ID NO 29
<211> LENGTH: 96
<212> TYPE: PRT
<213> ORGANISM: Homo sapiens

<400> SEQUENCE: 29

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
            35                  40                  45

Glu Phe Thr Val Pro Leu Gln Pro Pro Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

<210> SEQ ID NO 30
<211> LENGTH: 10
<212> TYPE: PRT
<213> ORGANISM: Homo sapiens
```

-continued

```
<400> SEQUENCE: 30

Gly Asn His Trp Ala Val Gly His Leu Met
1               5                   10

<210> SEQ ID NO 31
<211> LENGTH: 59
<212> TYPE: PRT
<213> ORGANISM: Homo sapiens

<400> SEQUENCE: 31

Met Val Asp Asn Lys Phe Asn Lys Glu Met Trp Ala Ala Trp Glu Glu
1               5                   10                  15

Ile Arg Asn Leu Pro Asn Leu Asn Gly Trp Gln Met Thr Ala Phe Ile
            20                  25                  30

Ala Ser Leu Val Asp Asp Pro Ser Gln Ser Ala Asn Leu Leu Ala Glu
        35                  40                  45

Ala Lys Lys Leu Asn Asp Ala Gln Ala Pro Lys
    50                  55

<210> SEQ ID NO 32
<211> LENGTH: 59
<212> TYPE: PRT
<213> ORGANISM: Homo sapiens

<400> SEQUENCE: 32

Met Val Asp Asn Lys Phe Asn Lys Glu Met Arg Asn Ala Tyr Trp Glu
1               5                   10                  15

Ile Ala Leu Leu Pro Asn Leu Asn Asn Gln Gln Lys Arg Ala Phe Ile
            20                  25                  30

Arg Ser Leu Tyr Gly Asp Pro Ser Gln Ser Ala Asn Leu Leu Ala Glu
        35                  40                  45

Ala Lys Lys Leu Asn Asp Ala Gln Ala Pro Lys
    50                  55

<210> SEQ ID NO 33
<211> LENGTH: 13
<212> TYPE: PRT
<213> ORGANISM: Homo sapiens

<400> SEQUENCE: 33

Met Trp Gln Pro Asp Thr Ala His His Trp Ala Thr Leu
1               5                   10

<210> SEQ ID NO 34
<211> LENGTH: 21
<212> TYPE: PRT
<213> ORGANISM: Artificial
<220> FEATURE:
<223> OTHER INFORMATION: Hinge linker sequence

<400> SEQUENCE: 34

Gly Pro Gln Pro Gln Pro Lys Pro Gln Pro Lys Pro Glu Pro Glu Pro
1               5                   10                  15

Gln Pro Gln Gly Gly
            20

<210> SEQ ID NO 35
<211> LENGTH: 52
<212> TYPE: PRT
<213> ORGANISM: Archaeoglobus fulgidus

<400> SEQUENCE: 35
```

-continued

```
Met Pro Pro Arg Pro Leu Asp Val Leu Asn Arg Ser Leu Lys Ser Pro
1               5                   10                  15

Val Ile Val Arg Leu Lys Gly Gly Arg Glu Phe Arg Gly Thr Leu Asp
                20                  25                  30

Gly Tyr Asp Ile His Met Asn Leu Val Leu Leu Asp Ala Glu Glu Ile
            35                  40                  45

Gln Asn Gly Glu
    50
```